United States Patent
McCaffey et al.

(10) Patent No.: US 7,358,231 B1
(45) Date of Patent: Apr. 15, 2008

(54) PANCREATIC CANCER SECRETED TARGETS AND USES THEREOF

(75) Inventors: Ian McCaffey, Moorpark, MD (US); Kim Alving, Rockville, MD (US); Bruno Domon, Giblenstrasse (CH); Steven Ruben, Brookeville, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 11/606,949

(22) Filed: Dec. 1, 2006

Related U.S. Application Data

(60) Provisional application No. 60/781,305, filed on Mar. 13, 2006, provisional application No. 60/741,041, filed on Dec. 1, 2005.

(51) Int. Cl.
*A61K 31/00* (2006.01)
*C07K 1/00* (2006.01)

(52) U.S. Cl. .......................................... 514/12; 530/350

(58) Field of Classification Search ................... 514/12; 530/350
See application file for complete search history.

(56) References Cited

FOREIGN PATENT DOCUMENTS

WO        053776    *   9/2000

* cited by examiner

*Primary Examiner*—Maryam Monshipouri
(74) *Attorney, Agent, or Firm*—Victor K. Lee; Justin D. Karjala

(57) ABSTRACT

The present invention provides a method for diagnosing and detecting diseases associated with pancreas. The present invention provides one or more proteins or fragments thereof, peptides or nucleic acid molecules differentially expressed in pancreatic diseases (PCAST) and antibodies binds to PCAST. The present invention provides that PCAST is used as targets for screening agents that modulates the PCAST activities. Further the present invention provides methods for treating diseases associated with pancreas.

15 Claims, No Drawings

PANCREATIC CANCER SECRETED TARGETS AND USES THEREOF

This application claims priority to Provisional Applications 60/741,041 filed Dec. 1, 2005 and 60/781,305, filed Mar. 13, 2006, respectively.

FIELD OF THE INVENTION

This invention relates to the fields of molecular biology and oncology. Specifically, the invention provides a molecular marker and a therapeutic agent for use in the diagnosis and treatment of cancers.

BACKGROUND OF THE INVENTION

Cancer currently constitutes the second most common cause of death in the United States. Carcinomas of the pancreas are the eighth most prevalent form of cancer and fourth among the most common causes of cancer deaths in this country.

The prognosis for pancreatic carcinoma is, at present, very poor, it displays the lowest five-year survival rate among all cancers. Such prognosis results primarily from delayed diagnosis, due in part to the fact that the early symptoms are shared with other more common abdominal ailments. Despite the advances in diagnostic imaging methods like ultrasonography (US), endoscopic ultrasonography (EUS), dualphase spiral computer tomography (CT), magnetic resonance imaging (MRT), endoscopic retrograde cholangiopancreatography (ERCP) and transcutaneous or EUS-guided fine-needle aspiration (FNA), distinguishing pancreatic carcinoma from benign pancreatic diseases, especially chronic pancreatitis, is difficult because of the similarities in radiological and imaging features and the lack of specific clinical symptoms for pancreatic carcinoma.

Substantial efforts have been directed to developing tools useful for early diagnosis of pancreatic carcinomas. Nonetheless, a definitive diagnosis is often dependent on exploratory surgery which is inevitably performed after the disease has advanced past the point when early treatment may be effected.

One promising method for early diagnosis of various forms of cancer is the identification of specific biochemical moieties, termed targets expressed differentially in the cancerous cells. Antibodies which will specifically recognize and bind to the targets in the cancerous cells potentially provide powerful tools for the diagnosis and treatment of the particular malignancy.

Secreted Proteins

Many human proteins serve as pharmaceutically active compounds. Several classes of human proteins that serve as such active compounds include hormones, cytokines, cell growth factors, and cell differentiation factors. Most proteins that can be used as a pharmaceutically active compound fall within the family of secreted proteins. It is, therefore, important in developing new pharmaceutical compounds to identify secreted proteins that can be tested for activity in a variety of animal models. The present invention advances the state of the art by providing many novel human secreted proteins.

Secreted proteins are generally produced within cells at rough endoplasmic reticulum, are then exported to the golgi complex, and then move to secretory vesicles or granules, where they are secreted to the exterior of the cell via exocytosis.

Secreted proteins are particularly useful as diagnostic markers. Many secreted proteins are found, and can easily be measured, in serum. For example, a 'signal sequence trap' technique can often be utilized because many secreted proteins, such as certain secretory breast cancer proteins, contain a molecular signal sequence for cellular export. Additionally, antibodies against particular secreted serum proteins can serve as potential diagnostic agents, such as for diagnosing cancer.

Secreted proteins play a critical role in a wide array of important biological processes in humans and have numerous utilities; several illustrative examples are discussed herein. For example, fibroblast secreted proteins participate in extracellular matrix formation. Extracellular matrix affects growth factor action, cell adhesion, and cell growth. Structural and quantitative characteristics of fibroblast secreted proteins are modified during the course of cellular aging and such aging related modifications may lead to increased inhibition of cell adhesion, inhibited cell stimulation by growth factors, and inhibited cell proliferative ability (Eleftheriou et al., *Mutat Res* 1991 Mar.-Nov; 256(2-6): 127-38).

The secreted form of amyloid beta/A4 protein precursor (APP) functions as a growth and/or differentiation factor. The secreted form of APP can stimulate neurite extension of cultured neuroblastoma cells, presumably through binding to a cell surface receptor and thereby triggering intracellular transduction mechanisms. (Roch et al., *Ann N Y Acad Sci* 1993 Sep. 24; 695:149-57). Secreted APPs modulate neuronal excitability, counteract effects of glutamate on growth cone behaviors, and increase synaptic complexity. The prominent effects of secreted APPs on synaptogenesis and neuronal survival suggest that secreted APPs play a major role in the process of natural cell death and, furthermore, may play a role in the development of a wide variety of neurological disorders, such as stroke, epilepsy, and Alzheimer's disease (Mattson et al., *Perspect Dev Neurobiol* 1998; 5(4):337-52).

Breast cancer cells secrete a 52K estrogen-regulated protein (see Rochefort et al., *Ann N Y Acad Sci* 1986; 464:190-201). This secreted protein is therefore useful in breast cancer diagnosis.

Two secreted proteins released by platelets, platelet factor 4 (PF4) and beta-thromboglobulin (betaTG), are accurate indicators of platelet involvement in hemostasis and thrombosis and assays that measure these secreted proteins are useful for studying the pathogenesis and course of thromboembolic disorders (Kaplan, *Adv Exp Med Biol* 1978; 102:105-19).

Vascular endothelial growth factor (VEGF) is another example of a naturally secreted protein. VEGF binds to cell-surface heparan sulfates, is generated by hypoxic endothelial cells, reduces apoptosis, and binds to high-affinity receptors that are up-regulated by hypoxia (Asahara et al., *Semin Interv Cardiol* 1996 September; 1(3):225-32). Many critical components of the immune system are secreted proteins, such as antibodies, and many important functions of the immune system are dependent upon the action of secreted proteins. For example, Saxon et al., *Biochem Soc Trans* 1997 May; 25(2):383-7, discusses secreted IgE proteins. For a further review of secreted proteins, see Nilsen-Hamilton et al., *Cell Biol Int Rep* 1982 September; 6(9): 815-36.

Secreted proteins, particularly members of the pancreatic cancer associated secreted proteins, are a major target for drug action and development. Accordingly, it is valuable to the field of pharmaceutical development to identify and characterize previously unknown members of this subfamily of secreted proteins. The present invention advances the state of the art by providing previously unidentified human secreted proteins that have homology to members of the secreted protein.

SUMMARY OF THE INVENTION

The present invention is based on the identification of secreted proteins that are differentially expressed in pancreatic cancer. A malignant cell often differs from a normal cell by a differential expression of one or more proteins. These differentially expressed proteins, and the fragments thereof, are important markers for the diagnosis of pancreatic disease such as cancer. The differentially expressed proteins of the present invention and the nucleic acids encoding said proteins and the fragments of said proteins are referred to herein as pancreatic cancer associated secreted target, PCAST proteins or PCAST nucleic acids or PCAST peptides, respectively.

The present invention provides peptides and proteins differentially expressed in pancreatic diseases (hereinafter PCAST). Based on the site of protein localization, e.g., blood or other body fluids, and protein characterization, e.g. hormone, enzyme, specific uses of these PCASTs are provided. Some of the PCASTs of the present invention serve as targets for one or more classes of theraputic agents, while others may be suitable for antibody theraputics.

Accordingly, the present invention provides a method for diagnosing or detecting pancreatic disease in a subject comprising: determining the level of one or more PCAST proteins, or any fragment(s) thereof, in a test sample from said subject, wherein said PCAST protein comprises a sequence selected from a group consisting of SEQ ID NOS:1-23; wherein a differential level of said PCAST protein(s) or fragment(s) in said sample relative to the level of said protein(s) or fragment(s) in a test sample from a healthy subject, or the level established for a healthy subject, is indicative of pancreatic disease.

The present invention also provides a method for detecting pancreatic cancer in a subject comprising: determining the level of one or more PCAST peptide(s) comprising a peptide sequence selected from a group consisting of SEQ ID NOS:40-51 in a test sample from said subject, wherein a differential level of said PCAST peptide(s) in said sample to the level of said PCAST peptide(s) in a test sample from a healthy subject, or the level of said PCAST peptide(s) established for a healthy subject, is indicative of pancreatic disease.

The present invention further provides a method for detecting pancreatic disease in a subject comprising: determining the level of one or more PCAST nucleic acid(s), or any fragment(s) thereof, in a test sample from said subject, wherein said PCAST nucleic acid(s) encode a PCAST protein sequence selected from a group consisting of SEQ ID NOS:1-23; wherein a differential level of said PCAST nucleic acids or fragment(s) in said sample relative to the level of said protein(s) or fragment(s) in a test sample from a healthy subject, or the level established for a healthy subject, is indicative of pancreatic disease.

The invention also provides methods for detecting the PCAST peptides, genes or mRNAs in a test sample for use in diagnosing the presence, absence or progression of a disease. The test sample includes but is not limited to a biological sample such as tissue, blood, serum or biological fluid.

The present invention further provides a purified antibody that binds specifically to a protein molecule, or any fragment thereof, selected from a group consisting of SEQ ID NOS: 1-23.

The present invention further provides a composition comprising an antibody that binds to a protein selected from a group consisting of SEQ ID NOS:1-23, and an acceptable carrier.

The present invention further provides a method for treating pancreatic disease, comprising administering to a patient in need of said treatment a therapeutically effective amount of one or more antibody(ies) of this invention.

The present invention further provides a method for treating pancreatic disease comprising (i) identifying a subject having pancreatic disease and (ii) administering to a said patient a therapeutically effective amount of one or more antibody(ies) of this invention.

The present invention further provides a method to screen for agents that modulate PCAST protein activity, comprising the steps of (i) contacting a test agent with a PCAST protein and (ii) assaying for PCAST protein activity, wherein a change in said activity in the presence of said agent relative to PCAST protein activity in the absence of said agent indicates said agent modulates said PCAST protein activity.

The present invention further provides a method to screen for agents that bind to PCAST protein, comprising the steps of (i) contacting a test agent with a PCAST protein and (ii) measuring the level of binding of agent to said PCAST protein.

The invention also provides diagnostic methods for human disease, in particular for pancreatic diseases or cancers, its metastatic stage, and therapeutic potential.

The present invention further provides diagnostic method for epithelial-cell related cancers. In particular pancreas, lung, colon, prostate, ovarian, breast, bladder renal, hepatocellular, pharyngeal, and gastric cancers.

The invention also provides a method for monitoring the disease progression and the treatment progress.

The invention further provide a method of diagnosis by an array, wherein the array is immobilized with two or more PCAST proteins, peptides or nucleic acid molecules. The proteins, peptides or nucleic acid molecules include but are not limited to the SEQ ID NOS:1-23.

The invention also provides monoclonal or polyclonal antibodies and composition thereof reactive with antigentic portion of PCAST protein, peptides or fragments thereof in a form for use in pancreatic diseases diagnosis.

The invention further provides an immunogenic antibody for treating pancreatic disease or diseases associated with pancreatic diseases.

The present invention provides a method for screening agents that modulate PCAST activity, comprising the steps of (a) contacting a sample comprising PCAST with an agent; and (b) assaying for PCAST activity, wherein a change in said PCAST activity in the presence of said agent relative to PCAST activity in the absence of said compound indicates said agent modulates PCAST. The agents include but are not limited to protein, peptide, antibody, nucleic acid such as antisense RNA, RNAi fragments, small molecules.

The present invention further provides a method for treating pancreatic diseases, comprising: administering to a patient one or more agents in a therapeutically effective amount to treat pancreatic diseases.

The present invention provides a method for treating pancreatic diseases, comprising: identifying a subject having pancreatic diseases; and administering to a patient to one or more antibodies in a therapeutically effective amount to treat pancreatic diseases.

The present invention further provides therapeutic potential for epithelial-cell related cancers. In particular pancreas, lung, colon, prostate, ovarian, breast, bladder renal, hepatocellular, pharyngeal and gastric cancers.

DESCRIPTION OF THE FILES CONTAINED ON THE CD-R NAMED CL001658CDR

The CD-R named CL001658CDR contains the following two text (ASCII) files:

1) File SEQLIST_1658 txt provides the Sequence Listing. The Sequence Listing provides the protein sequences (SEQ ID NOS:1-23); transcript sequences (SEQ ID NOS:24-39) and peptide sequences (SEQ ID NOS:40-51) as shown in Table 1. File SEQLIST_1658.txt is 132 KB in size.

2) File TABLE1_1658.txt provides Table 1, which is 10 KB in size.

The material contained on the CD-R labeled CL001658CDR is hereby incorporated by reference pursuant to 37 CFR 1.77(b)(4).

DESCRIPTION OF TABLE 1

Table 1 (provided on the CD-R) discloses the PCAST proteins, transcripts, and peptides (each protein, transcript, and peptide is represented by a SEQ ID NO, and the corresponding sequence is provided in the Sequence Listing; the range of numbers in parentheses following each peptide SEQ ID NO represent the amino acid residues of the location of the peptide within its corresponding protein), the pancreatic cancer cell lines or tissues, and the expression ratio ("ratio") compared to the control sample.

The expression ratio is based on measuring the level of the peptides. Numerical representation of overexpression is indicated by more than two, whereas numerical representation of underexpression is indicated by less than 0.5. Overexpressed singleton indicates that the peptide peak in a diseased sample was detected and there was no peak detected in control samples. Under-expressed singleton indicates that the peptide peak was detected in the control sample and there was no peak in the diseased sample.

The protein/gene/transcript information provided for each target includes any or all of the information selected from:
  a protein SEQ ID NO
  a Celera internal identification number for the protein (hCP and/or UID)
  a public protein accession number (Genbank, e.g., RefSeq NP number, Swiss-prot, or Derwent) for the protein
  a protein name recognized in the art
  a Celera internal identification number for the gene (hCG and/or UID)
  an art-recognized gene symbol
  Celera genomic axis position (indicating start nucleotide position-stop nucleotide position)
  the chromosome number of the chromosome on which the gene is located
  an OMIM (Online Mendelian Inheritance in Man; Johns Hopkins University/NCBI) public reference number for obtaining further information regarding the medical significance of each gene, and alternative gene/protein name(s) and/or symbol(s) in the OMIM entry
  a transcript SEQ ID NO
  a Celera internal identification number for the transcript (hCT and/or UID)
  a public transcript accession number (Genbank, e.g., RefSeq NM number, or Derwent)

DETAILED DESCRIPTION OF THE PREFERRED EMBODIMENTS

General Description

While the broadest definition of this invention is set forth in the Summary of the Invention, certain nucleic acids, peptides or proteins are preferred. For example a preferred method for detecting pancreatic disease by determining the level of one or more PCAST protein(s) or any fragment(s) thereof is wherein the level of PCAST protein(s) are determined by contacting one or more antibody(ies) that specifically bind to the antigenic regions of the PCAST protein(s). Further preferred is a method wherein the level of two or more proteins are determined, more preferred wherein the level of four or more proteins are determined and most preferred wherein the level of eight or more proteins are determined.

A preferred method for detecting pancreatic disease by determining the level of one or more PCAST peptide(s) is wherein the level of PCAST peptides(s) are determined by contacting one or more antibody(ies) that specifically bind to the antigenic regions of the PCAST peptide(s). Further preferred is a method wherein the level of five or more peptides are determined, more preferred wherein the level of ten or more peptides are determined and most preferred wherein the level of fifteen or more peptides are determined.

A preferred method for detecting pancreatic disease by determining the level of one or more PCAST nucleic acid(s) is wherein the level of said PCAST nucleic acid(s) is determined by contacting one or more probes that specifically hybridize to said nucleic acid(s). Further preferred is a method wherein the level of two or more nucleic acids are determined, more preferred wherein the level of four or more nucleic acids are determined and most preferred wherein the level of eight or more nucleic acids are determined.

The methods for detecting pancreatic disease provided by the present invention may be used for diagnosing the presence of disease in a patent, monitoring the presence of pancreatic disease in patients undergoing treatment and testing for the reoccurrence of pancreatic disease in patients that were successfully treated for pancreatic disease; preferably wherein the pancreatic disease is pancreatic cancer. The test sample may be, but is not limited to, a biological sample such as tissue, blood, serum or biological fluid.

The present invention is based on the discovery of protein (s) and peptide(s) that are differentially expressed in pancreatic disease samples for example cancer sample versus normal pancreatic samples. These proteins and peptide, and the encoding nucleic acid molecules are associated with pancreatic diseases, hereinafter the PCAST protein, peptide or nucleic acids.

The discovery of disease specific target proteins is base on discoveries made using proteomics techniques. The method uses on MALDI-TOF TOF LC/MS analyses platform to generate protein expression profiles from pancreatic diseases tissues or cell lines in an effort to discover and identify novel molecules associated with the disease.

Based on these discoveries, the present invention provides proteins, peptides, nucleic acids that are differential in pancreatic diseases, as well as antibodies binds to the proteins or peptides. The present invention also provides methods for detection, monitoring, diagnosis, prognosis, preventive and treatment of pancreatic diseases. The present invention provides a detection reagent, markers for pancreatic diseases at various stages, comprises PCAST sequences isolated from human pancreatic diseases tissue, sera, cell lines, blood or biological fluids.

The present invention provides a method for treating pancreatic diseases targeting at PCAST. The treatment includes administration of a therapeutically effective amount of composition comprise, but not limit to, an antibody, an immunogentic peptide which induces T cell response, a small molecule, a protein or a nucleic acid molecule. The composition further comprises an agonist or antagonist to PCAST. A "Panceratic disease" includes pancreatic cancer, pancreatic tumor (exocrine or endocrine), pancreatic cysts, acute pancreatitis, chronic pancreatitis, diabetes (type I and II) as well as pancreatic trauma, preferably pancreatic cancer.

The present invention may further provide a diagnostic or therapeutic potential for epithelial-cell related cancers, which include but are not limited to pancreas, lung, colon, prostate, ovarian, breast, bladder renal, hepatocellular, pharyngeal and gastric cancers.

The present invention further provides the target for screening an agent for PCAST, wherein the agent is compounds of small molecules, proteins, peptides, nucleic acids, antibodies or other agonists or antagonists.

PCAST Peptide/Proteins and Peptides

The present invention provides isolated PCAST peptide and protein molecules that consisting of, consisting essentially of, or comprising the amino acid sequences of the PCAST peptides and proteins disclosed in the Table 1, as well as all obvious variants of these peptides that are within the art to make and use. Some of these variants are described in detail below.

In one embodiment PCAST peptides include, but are not limited to, the amino acid sequence of SEQ ID NOS:40-51 and variants thereof. A PCAST protein includes, but is not limited to, the amino acid sequence of SEQ ID NOS:1-23 and variants thereof. PCAST proteins may be differentially expressed in pancreatic cell line, blood, tissue, serum or body fluids.

The peptide or protein or fragment thereof, to which the invention pertains, however, are not to be construed as encompassing peptide, protein or fragment that may be disclosed publicly prior to the present invention.

The PCAST proteins and peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule are discussed below).

As used herein, a "peptide" is defined as amino acid sequences between 5-20 amino acids derived from PCAST proteins such as SEQ ID NOS:1-23 or variants thereof. The peptide differentially expressed in either pancreatic diseases cell line, blood, tissue, serum or body fluids. In one embodiment peptides include, but are not limited to, the amino acid sequence of SEQ ID NOS:40-51, or variants thereof.

As used herein, a "protein" is full-length protein differentially expressed in pancreatic diseases cell line, tissue, blood, serum or body fluids. A protein includes, but are not limited to, the amino acid sequence of SEQ ID NOS:1-23.

A peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule are discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the PCAST peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated PCAST proteins and peptides can be purified from cells that naturally express it, purified from cells that have been altered to express it (recombinant), or synthesized using known protein synthesis methods. Sambrook et al., Molecular Cloning: A Laboratory Manual.3rd. ed., Cold Spring Harbor Laboratory Press, Cold Spring Harbor, N.Y., (2001). Experimental data as provided in Table 1 indicates expression in human pancreatic cell lines. For example, a nucleic acid molecule encoding the PCAST protein or peptide is cloned into an expression vector, the expression vector introduced into a host cell and the protein expressed in the host cell. The protein or peptide can then be isolated from the cells by an appropriate purification scheme using standard protein purification techniques. Many of these techniques are described in detail below.

A PCAST peptide or protein can be attached to heterologous sequences to form chimeric or fusion proteins. Such Schimeric and fusion proteins comprise a peptide operatively linked to a heterologous protein having an amino acid sequence not substantially homologous to the peptide. "Operatively linked" indicates that the peptide and the heterologous protein are fused in-frame. The heterologous protein can be fused to the N-terminus or C-terminus of the peptide.

In some uses, the fusion protein does not affect the activity of the peptide or protein per se. For example, the fusion protein can include, but is not limited to, fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant PCAST proteins or peptides. In certain host cells (e.g., mammalian host cells), expression and/or secretion of a protein can be increased by using a heterologous signal sequence.

A chimeric or fusion PCAST protein or peptide can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A PCAST-encoding nucleic acid can be cloned into such an expression vector such that the fusion moiety is linked in-frame to the PCAST protein or peptide.

As mentioned above, the PCAST peptide or the PCAST protein has obvious variants of the amino acid sequence, such as naturally occurring mature forms of the PCAST, allelic/sequence variants of the PCAST, non-naturally occurring recombinantly derived variants of the PCASTs, and orthologs and paralogs of the PCAST proteins or peptides. Such variants can readily be generated using art-known techniques in the fields of recombinant nucleic acid technology and protein biochemistry.

It is understood, however, that PCAST and variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the PCAST peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48):444-453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., Nucleic Acids Res. 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215:403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the PCAST peptides of the present invention as well as being encoded by the same genetic locus as the PCAST peptide provided herein (see Table 1).

Allelic variants of a PCAST peptide can readily be identified as being a human protein having a high degree (significant) of sequence homology/identity to at least a portion of the PCAST peptide as well as being encoded by the same genetic locus as the PCAST peptide provided herein. As used herein, two proteins (or a region of the proteins) have significant homology when the amino acid sequences are typically at least about 70-80%, 80-90%, and more typically at least about 90-95% or more homologous. A significantly homologous amino acid sequence, according to the present invention, will be encoded by a nucleic acid sequence that will hybridize to a PCAST peptide encoding nucleic acid molecule under stringent conditions as more fully described below.

Paralogs of a PCAST peptide can readily be identified as having some degree of significant sequence homology/identity to at least a portion of the PCAST peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a PCAST peptide encoding nucleic acid molecule under moderate to stringent conditions as more fully described below.

Orthologs of a PCAST peptide can readily be identified as having some degree of significant sequence homology/identity to at least a portion of the PCAST peptide as well as being encoded by a gene from another organism. Preferred orthologs will be isolated from mammals, preferably primates, for the development of human therapeutic targets and agents. Such orthologs will be encoded by a nucleic acid sequence that will hybridize to a PCAST peptide encoding nucleic acid molecule under moderate to stringent conditions, as more fully described below, depending on the degree of relatedness of the two organisms yielding the proteins.

Non-naturally occurring variants of the PCAST peptides of the present invention can readily be generated using recombinant techniques. Such variants include, but are not limited to deletions, additions and substitutions in the amino acid sequence of the PCAST peptide. For example, one class of substitutions is conserved amino acid substitution. Such substitutions are those that substitute a given amino acid in a PCAST peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

Variant PCAST peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081-1085 (1989)). The latter procedure introduces single alanine mutations at every residue in the molecule. The resulting mutant molecules are then tested for biological activity such as PCAST activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899-904 (1992); de Vos et al. Science 255:306-312 (1992)).

The present invention further provides fragments of the PCASTs, in addition to proteins and peptides that comprise and consist of such fragments, particularly those comprising the residues identified in Table 1. As used herein, a fragment comprises at least 8, 10, 12, 14, 16, 18, 20 or more contiguous amino acid residues from a PCAST. Such fragments can be chosen based on the ability to retain one or more of the biological activities of the PCAST or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the PCAST, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in PCASTs are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (Meth. Enzymol. 182: 626-646 (1990)) and Rattan et al. (Ann. N.Y. Acad. Sci. 663:48-62 (1992)).

Accordingly, the PCASTs of the present invention also encompass derivatives or analogs in which a substituted amino acid residue is not one encoded by the genetic code, in which a substituent group is included, in which the mature PCAST is fused with another compound, such as a compound to increase the half-life of the PCAST (for example, polyethylene glycol), or in which the additional amino acids are fused to the mature PCAST, such as a leader or secretory sequence or a sequence for purification of the mature PCAST or a pro-protein sequence.

Protein/Peptide Uses

The proteins of the present invention can be used in substantial and specific assays related to the functional information provided in Table 1; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a PCAST-effector protein interaction or PCAST-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", $3^{rd}$, ed Cold Spring Harbor Laboratory Press, Sambrook, J., E. F. Fritsch and T. Maniatis eds., 2001, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, PCASTs isolated from humans and their human/mammalian orthologs serve as targets for identifying agents for use in mammalian therapeutic applications, e.g. a human drug, particularly in modulating a biological or pathological response in a cell or tissue that expresses the PCAST. Experimental data as provided in Table 1 indicate that the PCASTs of the present invention are expressed at differential level in various pancreatic cell lines, for example, SEQ ID NOS:1-23 are overexpressed in all tested cell lines. A large percentage of pharmaceutical agents are being developed that modulate the activity of PCAST proteins, particularly members of the PCAST subfamily (see Background of the Invention). The structural and functional information provided in the Background and Table 1 provide specific and substantial uses for the molecules of the present invention, particularly in combination with the expression information provided in Table 1. Experimental data as provided in Table 1 indicates expression in human pancreatic cell lines. Such uses can readily be determined using the information provided herein, that which is known in the art, and routine experimentation.

The proteins of the present invention (including variants and fragments that may have been disclosed prior to the present invention) are useful for biological assays related to PCASTs that are related to members of the PCAST subfamily. Such assays involve any of the known PCAST functions or activities or properties useful for diagnosis and treatment of PCAST-related conditions that are specific for the subfamily of PCASTs that the one of the present invention belongs to, particularly in cells and tissues that express the PCAST. Experimental data as provided in Table 1 indicate that the PCASTs of the present invention are expressed at differential level in various pancreatic cell lines, for example, SEQ ID NOS:1-23 are overexpressed in all tested cell lines.

The proteins of the present invention are also useful in drug screening assays, in cell-based or cell-free systems. Cell-based systems can be native, i.e., cells that normally express the PCAST, as a biopsy or expanded in cell culture. Experimental data as provided in Table 1 indicates expression in human pancreatic cell lines. In an alternate embodiment, cell-based assays involve recombinant host cells expressing the PCAST protein.

The polypeptides can be used to identify compounds or agents that modulate PCAST activity of the protein in its natural state or an altered form that causes a specific disease or pathology associated with the PCAST. Both the PCASTs of the present invention and appropriate variants and fragments can be used in high-throughput screens to assay candidate compounds for the ability to bind to the PCAST. These compounds can be further screened against a functional PCAST to determine the effect of the compound on the PCAST activity. Further, these compounds can be tested in animal or invertebrate systems to determine activity/effectiveness. Compounds can be identified that activate (agonist) or inactivate (antagonist) the PCAST to a desired degree.

Further, the proteins of the present invention can be used to screen a compound or an agent for the ability to stimulate or inhibit interaction between the PCAST protein and a molecule that normally interacts with the PCAST protein, e.g. a substrate or an extracellular binding ligand or a component of the signal pathway that the PCAST protein normally interacts (for example, a cytosolic signal protein or another PCAST). Such assays typically include the steps of combining the PCAST protein with a candidate compound under conditions that allow the PCAST protein, or fragment, to interact with the target molecule, and to detect the formation of a complex between the protein and the target or to detect the biochemical consequence of the interaction with the PCAST protein and the target, such as any of the associated effects of signal transduction such as protein phosphorylation, cAMP turnover, and adenylate cyclase activation, etc.

Candidate compounds or agents include, for example, 1) peptides such as soluble peptides, including Ig-tailed fusion peptides and members of random peptide libraries (see, e.g., Lam et al., Nature 354:82-84 (1991); Houghten et al., Nature 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767-778 (1993)); 3) antibodies (e.g., polyclonal, monoclonal, humanized, anti-idiotypic, chimeric, and single chain antibodies as well as Fab, F(ab')2, Fab expression library fragments, and epitope-binding fragments of antibodies); and 4) small organic and inorganic molecules (e.g., molecules obtained from combinatorial and natural product libraries).

One candidate compound or agent is a soluble fragment of the PCAST that competes for substrate binding. Other candidate compounds include mutant PCASTs or appropriate fragments containing mutations that affect PCAST function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) PCAST activity. The assays typically involve an assay of events in the signal transduction pathway that indicate PCAST activity. Thus, the phosphorylation of a substrate, activation of a protein, a change in the expression of genes that are up- or down-regulated in response to the PCAST protein dependent signal cascade can be assayed.

Any of the biological or biochemical functions mediated by the PCAST can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in Table 1. Specifically, a biological function of a cell or tissues that expresses the PCAST can be assayed. Experimental data as provided in Table 1 indicate that the PCASTs of the present invention are expressed at differential level in various pancreatic cell lines, for example, SEQ ID NOS:1-23 are overexpressed in all tested cell lines.

Binding and/or activating compounds can also be screened by using chimeric PCAST proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native PCAST. Accordingly, a different set of signal transduction components is available as an end-point assay for activation. This allows for assays to be performed in other than the specific host cell from which the PCAST is derived.

The proteins of the present invention are also useful in competition binding assays in methods designed to discover compounds that interact with the PCAST (e.g. binding partners and/or ligands). Thus, a compound is exposed to a PCAST polypeptide under conditions that allow the compound to bind or to otherwise interact with the polypeptide. Soluble PCAST polypeptide is also added to the mixture. If the test compound interacts with the soluble PCAST polypeptide, it decreases the amount of complex formed or activity from the PCAST. This type of assay is particularly useful in cases in which compounds are sought that interact with specific regions of the PCAST. Thus, the soluble polypeptide that competes with the target PCAST region is designed to contain peptide sequences corresponding to the region of interest.

To perform cell free drug screening assays, it is sometimes desirable to immobilize either the PCAST protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of PCAST-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a PCAST-binding protein and a candidate compound are incubated in the PCAST protein-presenting wells and the amount of complex trapped in the well can be quantitated. Methods for detecting such complexes, in addition to those described above for the GST-immobilized complexes, include immunodetection of complexes using antibodies reactive with the PCAST protein target molecule, or which are reactive with PCAST protein and compete with the target molecule, as well as PCAST-linked assays which rely on detecting an enzymatic activity associated with the target molecule.

The following technologies can be used to detect interactions between a protein and a compound without knowing the biological function of the protein. A short description of three methods is presented, including fluorescence correlation spectroscopy, surface-enhanced laser desorption/ionization, and biacore technologies.

Fluorescence Correlation Spectroscopy (FCS) theory was developed in 1972 but it is only in recent years that the technology to perform FCS became available (Madge et al. (1972) Phys. Rev. Lett., 29: 705-708; Maiti et al. (1997) Proc. Natl. Acad. Sci. USA, 94: 11753-11757). FCS measures the average diffusion rate of a fluorescent molecule within a small sample volume. The sample size can be as low as 10' fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analyzed is expressed as a recombinant protein with a sequence tag, such as a poly-histidine sequence, inserted at the N or C-terminus. The expression takes place in *E. coli*, yeast or insect cells. The protein is purified by chromatography. For example, the poly-histidine tag can be used to bind the expressed protein to a metal chelate column such as Ni2+ chelated on iminodiacetic acid agarose. The protein is then labeled with a fluorescent tag such as carboxytetramethyl-rhodamine or BODIPY.RTM. (Molecular Probes, Eugene, Oreg.). The protein is then exposed in solution to the potential ligand, and its diffusion rate is determined by FCS using instrumentation available from Carl Zeiss, Inc. (Thornwood, N.Y.). Ligand binding is determined by changes in the diffusion rate of the protein.

Surface-Enhanced Laser Desorption/Ionization (SELDI) was invented by Hutchens and Yip during the late 1980's (Hutchens and Yip (1993) Rapid Commun. Mass Spectrom. 7: 576-580). When coupled to a time-of-flight mass spectrometer (TOF), SELDI provides a mean to rapidly analyze molecules retained on a chip. It can be applied to ligand-protein interaction analysis by covalently binding the target protein on the chip and analyze by MS the small molecules that bind to this protein (Worrall et al. (1998) Anal. Biochem. 70: 750-756). In a typical experiment, the target to be analyzed is expressed as described for FCS. The purified protein is then used in the assay without further preparation. It is bound to the SELDI chip either by utilizing the poly-histidine tag or by other interaction such as ion exchange or hydrophobic interaction. The chip thus prepared is then exposed to the potential ligand via, for example, a delivery system capable to pipet the ligands in a sequential manner (autosampler). The chip is then submitted to washes of increasing stringency, for example a series of washes with buffer solutions containing an increasing ionic strength. After each wash, the bound material is analyzed by submitting the chip to SELDI-TOF. Ligands that specifically bind the target will be identified by the stringency of the wash needed to elute them.

Biacore relies on changes in the refractive index at the surface layer upon binding of a ligand to a protein immobilized on the layer. In this system, a collection of small ligands is injected sequentially in a 2-5 ul cell with the immobilized protein. Binding is detected by surface plasmon resonance (SPR) by recording laser light refracting from the surface. In general, the refractive index change for a given change of mass concentration at the surface layer, is practically the same for all proteins and peptides, allowing a single method to be applicable for any protein (Liedberg et al. (1983) Sensors Actuators 4: 299-304; Malmquist (1993) Nature, 361: 186-187). In a typical experiment, the target to be analyzed is expressed as described for FCS. The purified protein is then used in the assay without further preparation. It is bound to the Biacore chip either by utilizing the poly-histidine tag or by other interaction such as ion exchange or hydrophobic interaction. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

Agents that modulate one of the PCASTs of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of PCAST protein activity identified according to these drug screening assays can be used to treat a subject with a disorder mediated by the PCAST pathway, by treating cells or tissues that express the PCAST. Experimental data as provided in Table 1 indicates expression in human pancreatic cell lines. These methods of treatment include the steps of administering a modulator of PCAST activity in a pharmaceutical composition to a subject in need of such treatment, the modulator being identified as described herein.

In yet another aspect of the invention, the PCAST proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with the PCAST and are involved in PCAST activity. Such PCAST-binding proteins are also likely to be involved in the propagation of signals by the PCAST proteins or PCAST targets as, for example, downstream elements of a PCAST-mediated signaling pathway. Alternatively, such PCAST-binding proteins are likely to be PCAST inhibitors.

The two-hybrid system is based on the modular nature of most transcription factors, which consist of separable DNA-binding and activation domains. Briefly, the assay utilizes two different DNA constructs. In one construct, the gene that codes for a PCAST protein is fused to a gene encoding the DNA binding domain of a known transcription factor (e.g., GAL-4). In the other construct, a DNA sequence, from a library of DNA sequences that encode an unidentified protein ("prey" or "sample") is fused to a gene that codes for the activation domain of the known transcription factor. If the "bait" and the "prey" proteins are able to interact, in vivo, forming a PCAST-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PCAST protein.

This invention further pertains to novel agents identified by the above-described screening assays. Accordingly, it is within the scope of this invention to further use an agent identified as described herein in an appropriate animal model. For example, an agent identified as described herein (e.g., a PCAST-modulating agent, an antisense PCAST nucleic acid molecule, an PCAST-RNAi fragment, a PCAST-specific antibody, or a PCAST-binding partner) can be used in an animal or other model to determine the efficacy, toxicity, or side-effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The PCAST proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in Table 1 indicates expression in human pancreatic cell lines. The method involves contacting a biological sample with a compound capable of interacting with the PCAST protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered PCAST activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10-11):983-985 (1996)), and Linder, M. W. (Clin. Chem. 43(2):254-266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the PCAST protein in which one or more of the PCAST functions in one population are different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and PCAST activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in Table 1 indicates expression in human pancreatic cell lines. Accordingly, methods for treatment include the use of the PCAST protein or fragments.

Antibodies

The present invention provides antibodies specifically bind to PCAST proteins or fragments thereof, peptides, or antigenic portion thereof.

The invention also provides antibodies that selectively bind to one of the peptides of the present invention, a protein comprising such a peptide, as well as variants and fragments thereof as describe above.

The antibody of present invention selectively binds a target PCAST when it binds the target domain and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

The term "antibody" is used in the broadest sense, and specifically covers monoclonal antibodies (including full length monoclonal antibodies), polyclonal antibodies, multispecific antibodies (e.g., bispecific antibodies), humanized antibody and antibody fragments (e.g., Fab, F(ab').sub.2 and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules that lack antigen specificity.

As used herein, antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains. Chothia et al., J. Mol. Biol. 186, 651-63 (1985); Novotny and Haber, Proc. Natl. Acad. Sci. USA 82 4592-4596 (1985).

An "isolated" antibody is one which has been identified and separated and/or recovered from a component of the environment in which is produced. Contaminant components of its production environment are materials that would interfere with diagnostic or therapeutic uses for the antibody, and may include enzymes, hormones, and other proteinaceous or nonproteinaceous solutes. In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequentator; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

An "antigenic region" or "antigenic determinant" or an "epitope" includes any protein determinant capable of specific binding to an antibody. This is the site on an antigen to which each distinct antibody molecule binds. Epitopic determinants usually consist of active surface groupings of molecules such as amino acids or sugar side chains and usually have specific three-dimensional structural characteristics, as well as charge characteristics.

"Antibody specificity," is an antibody, which has a stronger binding affinity for an antigen from a first subject species than it has for a homologue of that antigen from a second subject species. Normally, the antibody "bind specifically" to a human antigen (i.e., has a binding affinity (Kd) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second subject species which is at least about 50 fold, or at least about 500 fold, or at least about 1000 fold, weaker than its binding affinity for the human antigen. The antibody can be of any of the various types of antibodies as defined above, but preferably is a humanized or human antibody (Queen et al., U.S. Pat. Nos. 5,530,101, 5,585,089; 5,693,762; and 6,180,370).

The present invention provides an "antibody variant," which refers to an amino acid sequence variant of an antibody wherein one or more of the amino acid residues have been modified. Such variants necessarily have less than 100% sequence identity or similarity with the amino acid sequence having at least 75% amino acid sequence identity or similarity with the amino acid sequence of either the heavy or light chain variable domain of the antibody, more preferably at least 80%, more preferably at least 85%, more preferably at least 90%, and most preferably at least 95%. Since the method of the invention applies equally to both polypeptides, antibodies and fragments thereof, these terms are sometimes employed interchangeably.

The term "variable" in the context of variable domain of antibodies refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementary determining regions (CDRs) also known as hypervariable regions both in the light chain and the heavy chain variable domains. There are at least two techniques for determining CDRs: (1) an approach based on cross-species sequence variability (i.e., Kabat et al., Sequences of Proteins of Immunological Interest (National Institute of Health, Bethesda, Md. 1987); and (2) an approach based on crystallographic studies of antigen-antibody complexes (Chothia, C. et al. (1989), Nature 342: 877). The more highly conserved portions of variable domains are called the framework (FR). The variable domains of native heavy and light chains each comprise four FR regions, largely adopting a .beta.-Sheet configuration, connected by three CDRs, which form loops connecting, and in some cases forming part of, the .beta.-sheet structure. The CDRs in each chain are held together in close proximity by the FR regions and, with the CDRs from the other chain, contribute to the formation of the antigen-binding site of antibodies (see Kabat et al.) The constant domains are not involved directly in binding an antibody to an antigen, but exhibit various effector functions, such as participation of the antibody in antibody-dependent cellular toxicity.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of crosslinking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

An "Fv" fragment is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment (also designated as F(ab)) also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

The present invention further provides monoclonal antibody, polyclonal antibody as well as humanized antibody. In general, to generate antibodies, an isolated peptide is used as an immunogen and is administered to a mammalian organism, such as a rat, rabbit or mouse. The full-length protein, an antigenic peptide fragment or a fusion protein of the PCAST protein can be used. Particularly important fragments are those covering functional domains, some but not all the examples of the domains are identified in Table 1. Many methods are known for generating and/or identifying antibodies to a given target peptide. Several such methods are described by Harlow, Antibodies, Cold Spring Harbor Press, (1989).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" antibody indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol. Biol. 222: 581-597 (1991). For detailed procedure for making a monoclonal antibody, see the Example below.

"Humanized" forms of non-human (e.g. murine or rabbit) antibodies are chimeric immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-327 (1988) and Presta, Curr. Op. Struct. Biol. 2, 593-596 (1992).

Polyclonal antibodies may be prepared by any known method or modifications of these methods including obtaining antibodies from patients. For example, a complex of an immunogen such as PCAST protein, peptides or fragments thereof and a carrier protein is prepared and an animal is immunized by the complex according to the same manner as that described with respect to the above monoclonal antibody preparation and the description in the Example. A serum or plasma containing the antibody against the protein is recovered from the immunized animal and the antibody is separated and purified. The gamma globulin fraction or the IgG antibodies can be obtained, for example, by use of saturated ammonium sulfate or DEAE Sephadex, or other techniques known to those skilled in the art.

The antibody titer in the antiserum can be measured according to the same manner as that described above with respect to the supernatant of the hybridoma culture. Separation and purification of the antibody can be carried out according to the same separation and purification method of antibody as that described with respect to the above monoclonal antibody and in the Example.

The protein used here in as the immunogen is not limited to any particular type of immunogen. In one aspect, antibodies are preferably prepared from regions or discrete fragments of the PCAST proteins. Antibodies can be prepared from any region of the peptide as described herein. In particular, they are selected from a group consisting of SEQ ID NOS:40-51 and fragments of SEQ ID NOS:1-23. An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness.

Antibodies may also be produced by inducing production in the lymphocyte population or by screening antibody libraries or panels of highly specific binding reagents as disclosed in Orlandi et al. (1989; Proc Natl Acad Sci 86:3833-3837) or Winter et al. (1991; Nature 349:293-299). A protein may be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art. Smith G. P., 1991, Curr. Opin. Biotechnol. 2: 668-673.

The antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibody can be also made recombinantly. When using recombinant techniques, the antibody variant can be produced intracellularly, in the periplasmic space, or directly secreted into the medium. If the antibody variant is produced intracellularly, as a first step, the particulate debris, either host cells or lysed fragments, is removed, for example, by centrifugation or ultrafiltration. Carter et al., Bio/Technology 10: 163-167 (1992) describe a procedure for isolating antibodies, which are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibodies or antigen binding fragments may also be produced by genetic engineering. The technology for expression of both heavy and light cain genes in *E. coli* is the subject the following PCT patent applications; publication number WO 901443, WO901443, and WO 9014424 and in Huse et al., 1989 Science 246:1275-1281. The general recombinant methods are well known in the art.

The antibody composition prepared from the cells can be purified using, for example, hydroxylapatite chromatography, gel elecrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human delta.1, .delta.2 or .delta.4 heavy chains (Lindmark et al., J. Immunol. Meth. 62: 1-13 (1983)). Protein G is recommended for all mouse isotypes and for human .delta.3 (Guss et al., *EMBO J.* 5: 1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABXTM resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE.TM. chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in Table 1 indicate that the PCASTs of the present invention are expressed at differential level in various pancreatic cell lines, for example, SEQ ID NOS:1-23 are overexpressed in all tested cell lines. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in Table 1 indicates expression in human pancreatic cell lines. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in Table 1 indicates expression in human pancreatic cell lines. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy. More detection and diagnosis methods are described in detail below.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in Table 1 indicates expression in human pancreatic cell lines. Thus, where a specific protein has been correlated with expression in a specific tissue, antibodies that are specific for this protein can be used to identify a tissue type.

The antibodies are also useful for inhibiting protein function, for example, blocking the binding of the PCAST peptide to a binding partner such as a substrate or another antibody binding to the PCAST. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. More therapeutics methods are described in detail below.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a PCAST peptide or protein of the present invention. Such nucleic acid molecules will consist of, consist essentially of, or comprise a nucleotide sequence that encodes one of the PCAST peptides of the present invention, an allelic variant thereof, or an ortholog or paralog thereof. The nucleic acid molecules and the fragments thereof of the present invention pertains, however, are not to be construed as encompassing fragments that may be disclosed publicly prior to the present invention.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

The present invention further provides nucleic acid molecules that comprise the nucleotide sequences shown in Table 1 (SEQ ID NOS:24-39), or any nucleic acid molecule that encodes a protein provided in Table 1 (SEQ ID NOS: 1-23). A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In Table 1, human transcript sequences are provided. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the PCAST peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the PCAST proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in Table 1. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60-70%, 70-80%, 80-90%, and more typically at least about 90-95% or more homologous to the nucleotide sequence shown in the Table 1 or a fragment of this sequence. Such nucleic acid molecules can readily be identified as being able to hybridize under moderate to stringent conditions, to the nucleotide sequence shown in Table 1 or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60-70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1-6.3.6. One example of stringent hybridization conditions are hybridization in 6× sodium chloride/sodium citrate (SSC) at about 45C, followed by one or more washes in 0.2×SSC, 0.1% SDS at 50-65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in Table 1 and to isolate cDNA and genomic clones that correspond to variants (alleles, orthologs, etc.) producing the same or related peptides shown in Table 1.

The probe can correspond to any sequence along the entire length of the nucleic acid molecules provided in Table 1. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in Table 1 indicate that the PCASTs of the present invention are expressed at differential level in various pancreatic cell lines, for example, SEQ ID NOS:1-23 are overexpressed in all tested cell lines. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in PCAST protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a PCAST protein, such as by measuring a level of a PCAST-encoding nucleic acid in a sample of cells from a subject e.g., mRNA or genomic DNA, or determining if a PCAST gene has been mutated. Experimental data as provided in Table 1 indicate that the PCASTs of the present invention are expressed at differential level in various pancreatic cell lines, for example, SEQ ID NOS:1-23 are overexpressed in all tested cell lines. More detection and diagnosis methods are described in detail below.

Nucleic acid expression assays are useful for drug screening to identify compounds that modulate PCAST nucleic acid expression.

The invention thus provides a method for identifying a compound that can be used to treat a disorder associated with nucleic acid expression of the PCAST gene, particularly biological and pathological processes that are mediated by the PCAST in cells and tissues that express it. Experimental data as provided in Table 1 indicates expression in human pancreatic cell lines. The method typically includes assaying the ability of the compound to modulate the expression of the PCAST nucleic acid and thus identifying a compound that can be used to treat a disorder characterized by undesired PCAST nucleic acid expression. The assays can be performed in cell-based and cell-free systems. Cell-based assays include cells naturally expressing the PCAST nucleic acid or recombinant cells genetically engineered to express specific nucleic acid sequences.

The assay for PCAST nucleic acid expression can involve direct assay of nucleic acid levels, such as mRNA levels, or on collateral compounds involved in the signal pathway. Further, the expression of genes that are up- or down-regulated in response to the PCAST protein signal pathway can also be assayed. In this embodiment the regulatory regions of these genes can be operably linked to a reporter gene such as luciferase.

Thus, modulators of PCAST gene expression can be identified in a method wherein a cell is contacted with a candidate compound or agent and the expression of mRNA determined. The level of expression of PCAST mRNA in the presence of the candidate compound or agent is compared to the level of expression of PCAST mRNA in the absence of the candidate compound or agent. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound or an agent identified through drug screening as a gene modulator to modulate PCAST nucleic acid expression in cells and tissues that express the PCAST. Experimental data as provided in Table 1 indicate that the PCASTs of the present invention are expressed at differential level in various pancreatic cell lines, for example, SEQ ID NOS:1-23 are overexpressed in all tested cell lines. Modulation includes both up-regulation (i.e. activation or agonization) or down-regulation (suppression or antagonization) or nucleic acid expression.

Alternatively, a modulator for nucleic acid expression can be a small molecule or drug identified using the screening assays described herein as long as the drug or small molecule inhibits the PCAST nucleic acid expression in the cells and tissues that express the protein. Experimental data as provided in Table 1 indicates expression in human pancreatic cell lines.

The nucleic acid molecules are also useful for monitoring the effectiveness of modulating compounds or agents on the expression or activity of the PCAST gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in PCAST nucleic acid expression, and particularly in qualitative changes that lead to pathology. The nucleic acid molecules can be used to detect mutations in PCAST genes and gene expression products such as mRNA. The nucleic acid molecules can be used as hybridization probes to detect naturally occurring genetic mutations in the PCAST gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the PCAST gene associated with a dysfunction provides a diagnostic tool for an active disease or susceptibility to disease when the disease results from overexpression, underexpression, or altered expression of a PCAST protein.

Individuals carrying mutations in the PCAST gene can be detected at the nucleic acid level by a variety of techniques. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077-1080 (1988); and Nakazawa et al., PNAS 91:360-364 (1994)), the latter of which can be particularly useful for detecting point mutations in the gene (see Abravaya et al., Nucleic Acids Res. 23:675-682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a PCAST gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant PCAST gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127-162 (1996); and Griffin et al., Appl. Biochem. Biotechnol. 38:147-159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286-295 (1992)), electrophoretic mobility of mutant and wild type nucleic acid is compared (Orita et al., PNAS 86:2766 (1989); Cotton et al., Mutat. Res. 285:125-144 (1993); and Hayashi et al., Genet. Anal. Tech. Appl. 9:73-79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the PCAST gene in an individual in order to select an appropriate compound or dosage regimen for treatment.

Thus, nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control PCAST gene expression in cells, tissues, and organisms. A DNA antisense nucleic acid molecule is designed to be complementary to a region of the gene involved in transcription, preventing transcription and hence production of PCAST protein. An antisense RNA or DNA nucleic acid molecule would hybridize to the mRNA and thus block translation of mRNA into PCAST protein.

The nucleic acid of the present invention may also be used to specifically suppress gene expression by methods such as RNA interference (RNAi), which may also include cosuppression and quelling. This and antisense RNA or DNA of gene suppression are well known in the art. A review of this technique is found in Science 288:1370-1372, 2000. RNAi also operates on a post-transcriptional level and is sequence specific, but suppresses gene expression far more efficiently than antisense RNA. RNAi fragments, particularly double-stranded (ds) RNAi, can be also used to generate loss-of-function phenotypes.

The present invention relates to isolated RNA molecules (double-stranded; single-stranded) of from about 21 to about 25 nucleotides which mediate RNAi. As used herein, about 21 to about 25 nt includes nucleotides 17, 18, 19, 20, 21, 22, 23, 24, 25, 26, 27, 28 and 29 nucleotides in length. The isolated RNAs of the present invention mediate degradation of mRNA, the transcriptional product of a gene. Such mRNA is also referred to herein as mRNA to be degraded. As used herein, the terms RNA, RNA molecule(s), RNA segment(s) and RNA fragment(s) are used interchangeably to refer to RNA that mediates RNA interference. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the 21-25 nt RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAs are referred to as analogs or analogs of naturally-occurring RNA. RNA of 21-25 nucleotides of the present invention need only be sufficiently similar to natural RNA that it has the ability to mediate RNAi. As used herein the phrase "mediates RNAi" refers to the ability to distinguish which RNAs are to be degraded by the RNAi machinery or process. RNA that mediates RNAi interacts with the RNAi machinery such that it directs the degradation of particular mRNAs. Such RNA may include RNAs of various structure, including short hairpin RNA.

In one embodiment, the present invention relates to RNA molecules of about 21 to about 25 nucleotides that direct cleavage of specific mRNA to which their sequence corresponds. It is not necessary that there be perfect correspondence of the sequences, but the correspondence must be sufficient to enable the RNA to direct RNAi cleavage of the target mRNA (Holen et al. (2005) Nucleic Acids Res. 33, 4704-4710). In a particular embodiment, the 21-25 nt RNA molecules of the present invention comprise a 3' hydroxyl group.

The present invention relates to 21-25 nt RNAs of specific genes, produced by chemical synthesis or recombinant DNA techniques, that mediate RNAi. As used herein, the term isolated RNA includes RNA obtained by any means, including processing or cleavage of dsRNA; production by chemical synthetic methods; and production by recombinant DNA techniques. The invention further relates to uses of the 21-25 nt RNAs, such as for therapeutic or prophylactic treatment and compositions comprising 21-25 nt RNAs that mediate RNAi, such as pharmaceutical compositions comprising 21-25 nt RNAs and an appropriate carrier.

The present invention also relates to a method of mediating RNA interference of genes of a patient. In one embodiment, RNA of about 21 to about 25 nt which targets the specific mRNA to be degraded is introduced into a patient's cells. The cells are maintained under conditions allowing degradation of the mRNA, resulting in RNA-mediated interference of the mRNA of the gene in the cells of the patient. Treatment of patients with cancer with the RNAi will inhibit the growth and spread of the cancer and reduce the tumor. Treatment of patients using RNAi can also be in combination with other anti-cancer compounds. The RNAi may be used in combination with other treatment modalities, such as chemotherapy, cryotherapy, hyperthermia, radiation therapy, and other similar treatments. In one embodiment, a chemotherapy agent was combined with the RNAi. In another embodiment, a chemotherapy named Gemzar was used.

Treatment of cancer or tumors in patients requires introduction of the RNA into the cancer or tumor cells. RNA may be directly introduced into the cell, or introduced extracellularly into a cavity, interstitial space, into the circulation of a patient, or introduced orally. Methods for oral introduction include direct mixing of the RNA with food, as well as engineered approaches in which a species that is used as food is engineered to express the RNA and then ingested. Physical methods of introducing nucleic acids, for example, injection directly into the cell or extracellular injection into the patient, may also be used. Vascular or extravascular circulation, the blood or lymph system, and the cerebrospinal fluid are sites where the RNA may be introduced. RNA may be introduced into an embryonic stem cell, or another multipotent cell derived from the patient. Physical methods of introducing nucleic acids include injection of a solution containing the RNA, bombardment by particles covered by the RNA, soaking cells or tissue in a solution of the RNA, or electroporation of cell membranes in the presence of the RNA. A viral construct packaged into a viral particle may be used to introduce an expression construct into the cell, with the construct expressing RNA. Other methods known in the art for introducing nucleic acids to cells may be used, such as lipid-mediated carrier transport, chemical-mediated transport, and the like. Thus the RNA may be introduced along with components that perform one or more of the following activities: enhance RNA uptake by the cell, promote annealing of the duplex strands, stabilize the annealed strands, or otherwise increase inhibition of the target gene. The RNAi may be used in combination with other treatment modalities, such as chemotherapy, cryotherapy, hyperthermia, radiation therapy, and the like.

The present invention may be used alone or as a component of a kit having at least one of the reagents necessary to carry out the in vitro or in vivo introduction of RNA to tissue or patients. Preferred components are the dsRNA and a vehicle that promotes introduction of the dsRNA. Such a kit may also include instructions to allow a user of the kit to practice the invention.

Alternatively, a class of antisense molecules can be used to inactivate mRNA in order to decrease expression of PCAST nucleic acid. Accordingly, these molecules can treat a disorder characterized by abnormal or undesired PCAST nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the PCAST protein, such as substrate binding.

The nucleic acid molecules also provide vectors for gene therapy in patients containing cells that are aberrant in PCAST gene expression. Thus, recombinant cells, which include the patient's cells that have been engineered ex vivo and returned to the patient, are introduced into an individual where the cells produce the desired PCAST protein to treat the individual.

The invention also encompasses kits for detecting the presence of a PCAST nucleic acid in a biological sample. Experimental data as provided in Table 1 indicate that the PCASTs of the present invention are expressed at differential level in various pancreatic cell lines, for example, SEQ ID NOS:1-23 are overexpressed in all tested cell fines. For example, the kit can comprise reagents such as a labeled or labelable nucleic acid or agent capable of detecting PCAST nucleic acid in a biological sample; means for determining the amount of PCAST nucleic acid in the sample; and means for comparing the amount of PCAST nucleic acid in the sample with a standard. The compound or agent can be packaged in a suitable container. The kit can further comprise instructions for using the kit to detect PCAST protein mRNA or DNA.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequences to which the nucleic acid molecules described herein can be operably linked include promoters for directing mRNA transcription. These include, but are not limited to, the left promoter from bacteriophage, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., Molecular Cloning: A Laboratory Manual. 3rd. ed., Cold Spring Harbor Laboratory Press, Cold Spring Harbor, N.Y., (2001).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 3r. ed., Cold Spring Harbor Laboratory Press, Cold Spring Harbor, N.Y., (2001).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein; increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)). Recombinant protein expression can be maximized in host bacteria by providing a genetic background wherein the host cell has an impaired capacity to proteolytically cleave the recombinant protein. (Gottesman, S., Gene Expression Technology: Methods in Enzymology 185, Academic Press, San Diego, Calif. (1990) 119-128). Alternatively, the sequence of the nucleic acid molecule of interest can be altered to provide preferential codon usage for a specific host cell, for example *E. coli*. (Wada et al., Nucleic Acids Res. 20:2111-2118 (1992)).

The nucleic acid molecules can also be expressed by expression vectors that are operative in yeast. Examples of vectors for expression in yeast e.g., *S. cerevisiae* include pYepSec1 (Baldari, et al., EMBO J. 6:229-234 (1987)), pMFa (Kurjan et al., Cell 30:933-943 (1982)), pJRY88 (Schultz et al., Gene 54:113-123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell. Biol. 3:2156-2165 (1983)) and the pVL series (Lucklow et al., Virology. 170:31-39 (1989)).

In certain embodiments of the invention, the nucleic acid molecules described herein are expressed in mammalian cells using mammalian expression vectors. Examples of mammalian expression vectors include pCDM8 (Seed, B. Nature 329:840 (1987)) and pMT2PC (Kaufman et al., EMBO J. 6:187-195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. Molecular Cloning: A Laboratory Manual. 3rd, ed., Cold Spring Harbor Laboratory, Cold Spring Harbor Laboratory Press, Cold Spring Harbor, N.Y., 2001.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (Molecular Cloning: A Laboratory Manual. 3rd, ed., Cold Spring Harbor Laboratory, Cold Spring Harbor Laboratory Press, Cold Spring Harbor, N.Y., 2001).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as PCASTs, appropriate secretion signals are incorporated into the vector. The signal sequence can be endogenous to the peptides or heterologous to these peptides.

Where the peptide is not secreted into the medium, which is typically the case with PCASTs, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a PCAST protein or peptide that can be further purified to produce desired amounts of PCAST protein or fragments. Thus, host cells containing expression vectors are useful for peptide production.

Host cells are also useful for conducting cell-based assays involving the PCAST protein or PCAST protein fragments, such as those described above as well as other formats known in the art. Thus, a recombinant host cell expressing a native PCAST protein is useful for assaying compounds that stimulate or inhibit PCAST protein function.

Host cells are also useful for identifying PCAST protein mutants in which these functions are affected. If the mutants naturally occur and give rise to a pathology, host cells containing the mutations are useful to assay compounds that have a desired effect on the mutant PCAST protein (for example, stimulating or inhibiting function) which may not be indicated by their effect on the native PCAST protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA, which is integrated into the genome of a cell from which a transgenic animal develops and which remains in the genome of the mature animal in one or more cell types or tissues of the transgenic animal. These animals are useful for studying the function of a PCAST protein and identifying and evaluating modulators of PCAST protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal.

Any of the PCAST protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the PCAST protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. PNAS 89:6232-6236 (1992). Another example of a recombinase system is the FLP recombinase system of S. cerevisiae (O'Gorman et al. Science 251:1351-1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. Nature 385:810-813 (1997) and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, PCAST protein activation, and signal transduction, may not be evident from in vitro cell-free or cell-based assays. Accordingly, it is useful to provide non-human transgenic animals to assay in vivo PCAST protein function, including substrate interaction, the effect of specific mutant PCAST proteins on PCAST protein function and substrate interaction, and the effect of chimeric PCAST proteins. It is also possible to assess the effect of null mutations, that is, mutations that substantially or completely eliminate one or more PCAST protein functions.

Detection and Diagnosis

The present invention provides a method for detecting PCAST nucleic acids, proteins, peptides and fragments thereof that are differentially expressed in pancreatic diseases in a test sample, preferably in a biological sample.

The present invention further provides a method for diagnosing the pancreatic diseases, by detecting the nucleic acids, proteins, peptides and fragments thereof. The further embodiment includes but is not limited to, monitoring the disease prognosis (reoccurrence), diagnosing disease stage, preventing the disease and treating the disease.

As used herein, a "biological sample" can be collected from tissues, blood, sera, cell lines or biological fluids such as, plasma, interstitial fluid, urine, cerebrospinal fluid, and the like, containing cells. In preferred embodiments, a biological sample comprises cells or tissues suspected of having diseases (e.g., cells obtained from a biopsy).

As used herein, a "differential level" is defined as the level of PCAST protein or nucleic acids in a test sample either above or below the level of the ones in control samples, wherein the level of control samples is obtained from a control cell line, a normal tissue or body fluids, or combination thereof, from a healthy subject. While the protein is overexpressed, the expression of PCAST is preferably greater than about 20%, or preferably greater than about 30%, and most preferably greater than about 50% or more of pancreatic disease sample, at a level that is at least two fold, and preferably at least five fold, greater than the level of expression in control samples, as determined using a representative assay provided herein. While the protein is underexpressed, the expression of PCAST is preferably less than about 20%, or preferably less than about 30%, and most preferably less than about 50% or more of the pancreatic disease sample, at a level that is at least 0.5 fold, and preferably at least 0.2 fold less than the level of the expression in control samples, as determined using a representative assay provided herein.

As used herein, a "subject" can be a mammalian subject or non mammalian subject, preferably, a mammalian subject. A mammalian subject can be human or non-human, preferably human. A healthy subject is defined as a subject without detectable pancreatic diseases or pancreatic associated diseases by using conventional diagnostic methods.

As used herein, the "diseases" include pancreatic diseases and pancreatic associated disease.

As used herein, "cancer" includes epithelial-cell related cancers, for example pancreatic, lung, colon, prostate, ovarian, breast, bladder renal, hepatocellular, pharyngeal and gastric cancers.

Nucleic Acid Detections

The present invention is not limited to the detection methods described above. Any suitable detection method that allows for the specific detection of pancreatic diseases cells, tissues or organs may be utilized. For example, in some embodiments, the expression of RNA corresponding to a PCAST gene is detected by hybridization to an antisense oligonucleotide (described below). In other embodiments, RNA expression is detected by hybridization assays such as Northern blots, RNase assays, reverse transcriptase PCR amplification, and the like. One preferred detection method is using RT PCR by using TaqMan technology (ABI, Foster City, Calif.).

In another embodiment, the present invention provides a method for diagnosing or detecting pancreatic diseases in a subject comprising: determining the level of one or more PCAST nucleic acid molecules or any fragment(s) thereof in a test sample from said subject, wherein said PCAST nucleic acid molecule(s) comprises a sequence selected from a group consisting of SEQ ID NOS:24-39 and a combination thereof; wherein a differential level of said PCAST nucleic acid molecule(s) relative to the level of said nucleic acid molecule(s) in a test sample from a healthy subject, or the level established for a healthy subject, is indicative of pancreatic diseases.

In another embodiment, the detecting or diagnosing method comprises determining level of differential expression of 2, 4, 8, 10, 20 or more nucleic acid molecules, preferably, the nucleic acid molecules comprise or consists of a sequence selected from the group consisting of SEQ ID NOS:24-39 and combination thereof.

In further embodiments of the present invention, the presence of particular sequences in the genome of a subject is detected. Such sequences include PCAST sequences associated with abnormal expression of PCAST (e.g., overexpression or expression at a physiological inappropriate time). These sequences include polymorphisms, including polymorphisms in the transcribed sequence (e.g., that effect PCAST processing and/or translation) and regulatory sequences such as promoters, enhances, repressors, and the like. These sequences may also include polymorphisms in genes or control sequences associated with factors that affect expression such as transcription factors, and the like. Any suitable method for detecting and/or identifying these sequences is within the scope of the present invention including, but not limited to, nucleic acid sequencing, hybridization assays (e.g., Southern blotting), single nucleotide polymorphism assays (See e.g., U.S. Pat. No. 5,994,069, herein incorporated by reference in its entirety), and the like.

Protein Detections

The present invention provides methods for diagnosing or detecting the differential presence of PCAST protein. In some embodiments (e.g., where PCASTs are overexpressed in diseased cells), PCAST proteins are detected directly. In other embodiments (e.g., where the presence of a PCASTs are underexpressed), PCAST to the disease antigens are detected non-existence.

The diagnostic methods of the present invention find utility in the diagnosis and characterization of diseases. For example, the presence of an antibody to a specific protein may be indicative of a cancer or disease. In addition, certain PCAST may be indicative of a specific stage or sub-type of the same cancer or disease.

The information obtained is also used to determine prognosis and appropriate course of treatment. For example, it is contemplated that individuals with a specific PCAST expression or stage of pancreatic diseases may respond differently to a given treatment that individuals lacking the PCAST expression. The information obtained from the diagnostic methods of the present invention thus provides for the personalization of diagnosis and treatment.

In one embodiment, the present invention provides a method for monitoring pancreatic diseases treatment in a subject comprising: determining the level of one or more PCAST proteins or any fragment(s) or peptide(s) thereof in a test sample from said subject, wherein said PCAST protein(s) comprises a sequence selected from a group consisting of SEQ ID NOS:1-23, SEQ ID NOS:40-51 and a combination thereof; wherein an level of said PCAST protein(s) similar to the level of said protein(s) in a test sample from a healthy subject, or the level established for a healthy subject, is indicative of successful treatment.

In another embodiment, the present invention provides a method for diagnosing recurrence of pancreatic diseases following successful treatment in a subject comprising: determining the level of one or more PCAST proteins or any fragment(s) or peptide(s) thereof in a test sample from said subject, wherein said PCAST protein(s) comprises a sequence selected from a group consisting of SEQ ID NOS:1-23, SEQ ID NOS:40-51 or a combination thereof; wherein a changed level of said PCAST protein(s) relative to the level of said protein(s) in a test sample from a healthy subject, or the level established for a healthy subject, is indicative of recurrence of pancreatic diseases.

In yet another embodiment, the presend invention provides a method for diagnosing or detecting pancreatic diseases in a subject comprising: determining the level of one or more PCAST proteins or any fragment(s) or peptides thereof in a test sample from said subject, wherein said PCAST protein(s) comprises a sequence selected from a group consisting of SEQ ID NOS:1-23, SEQ ID NOS:40-51 and a combination thereof; wherein a differential level of said PCAST protein(s) relative to the level of said protein(s) in a test sample from a healthy subject, or the level established for a healthy subject, is indicative of pancreatic diseases.

The detecting or diagnosing method comprises determining level of differential expression of 2, 4, 8, 10, 20 or more proteins, preferably, the proteins are selected from a group consisting of SEQ ID NOS:1-23 and combination thereof.

Further, the detecting or diagnosing method comprises determining level of differential expression of 5, 10, 15, 20, 40, 60, 80, 100 or more PCAST peptides, preferably the peptides are selected from the group consisting of SEQ ID NOS:40-51 and combination thereof.

These methods are also useful for diagnosing diseases that show differential protein expression. As describe earlier, normal, control or standard values or level established from a healthy subject for protein expression are established by combining body fluids or tissue, cell extracts taken from a normal healthy mammalian or human subject with specific antibodies to a protein under conditions for complex formation. Standard values for complex formation in normal and diseased tissues are established by various methods, often photometric means. Then complex formation as it is expressed in a subject sample is compared with the standard values. Deviation from the normal standard and toward the diseased standard provides parameters for disease diagnosis or prognosis while deviation away from the diseased and toward the normal standard may be used to evaluate treatment efficacy.

In yet another embodiment, the present invention provides a detection or diagionistic method of PCASTs by using LC/MS. The proteins from cells are prepared by methods known in the art (R. Aebersold Nature Biotechnology Volume 21 Number 6 Jun. 2003). The differential expression of proteins in disease and healthy samples are quantitated using Mass Spectrometry and ICAT (Isotope Coded Affinity Tag) labeling, which is known in the art. ICAT is an isotope label technique that allows for discrimination between two populations of proteins, such as a healthy and a disease sample. The LC/MS spectra are collected for the labeled samples. The raw scans from the LC/MS instrument are subjected to peak detection and noise reduction software. Filtered peak lists are then used to detect 'features' corresponding to specific peptides from the original sample(s). Features are characterized by their mass/charge, charge, retention time, isotope pattern and intensity.

The intensity of a peptide present in both healthy and disease samples can be used to calculate the differential expression, or relative abundance, of the peptide. The intensity of a peptide found exclusively in one sample can be used to calculate a theoretical expression ratio for that peptide (singleton). Expression ratios are calculated for each peptide of each replicate of the experiment (Table 1). Thus overexpression or under expression of PCAST protein or peptide are similar to the expression pattern in Table 1 in a test subject indicates the likelihood of having pancreatic diseases or diseases associated with pancreas.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art (Ausubel, supra, unit 10.1-10.6). A two-site, monoclonal-based immunoassay utilizing antibodies reactive to two non-interfering epitopes is preferred, but a competitive binding assay may be employed (Pound (1998) Immunochemical Protocols, Humana Press, Totowa N.J.). More immunological detections are described in section below.

Antibody Detections

Antibodies are useful to detect the presence of one of the proteins or fragments thereof, peptides of the present invention in cells or tissues to determine the pattern of expression of the protein among various tissues in an organism and over the course of normal development.

Further, as described above, the antibodies can be used to assess expression in disease states such as in active stages of the disease or in an individual with a predisposition toward disease related to the protein's function. The antibodies can also be used to assess normal and aberrant subcellular localization of cells in the various tissues in an organism.

Detection on a protein by an antibody can be facilitated by coupling (i.e., physically linking) the antibody to a detectable substance. Examples of detectable substances include various enzymes, prosthetic groups, fluorescent materials, luminescent materials, bioluminescent materials, and radioactive materials (see below). The antibodies may also be useful in diagnostic assays, e.g., for detecting expression of an antigen, for example PCAST protein, peptide or fragment thereof, in specific cells, tissues, blood, serum or body fluids.

For diagnostic applications, the antibody or its variant typically will be labeled with a detectable moiety. Numerous labels are available which can be generally grouped into the following categories:

(a) Radioisotopes, such as $^{36}S$, $^{14}C$, $^{125}I$, $^{3}H$, and $^{131}I$. The antibody variant can be labeled with the radioisotope using the techniques described in Current Protocols in Immunology, vol 1-2, Coligen et al., Ed., Wiley-Interscience, New York, Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques disclosed in Current Protocols in Immunology, supra, for example. Fluorescence can be quantified using a fluorimeter.

(c) Various enzyme-substrate labels are available and U.S. Pat. Nos. 4,275,149, 4,318,980 provides a review of some of these. The enzyme generally catalyzes a chemical alteration of the chromogenic substrate, which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digloxin) and one of the different types of labels mentioned above is conjugated with an anti-hapten antibody (e.g. anti-digloxin antibody). Thus, indirect conjugation of the label with the antibody can be achieved.

In another embodiment of the invention, the antibody need not be labeled, and the presence thereof can be detected using a labeled antibody, which binds to the antibody.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The biological samples can then be tested directly for the presence of PCAST by assays (e.g., ELISA or radioimmunoassay) and format (e.g., microwells, dipstick (e.g., as described in International Patent Publication WO 93/03367), etc). Alternatively, proteins in the sample can be size separated (e.g., by polyacrylamide gel electrophoresis (PAGE)), in the presence or absence of sodium dodecyl sulfate (SDS), and the presence of PCAST detected by immunoblotting (e.g., Western blotting). Immunoblotting techniques are generally more effective with antibodies generated against a peptide corresponding to an epitope of a protein, and hence, are particularly suited to the present invention.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay. In some embodiments, an automated detection assay is utilized. Methods for the automation of immunoassays are well known in the art (See e.g., U.S. Pat. Nos. 5,885,530, 4,981,785, 6,159,750, and 5,358,691, each of which is herein incorporated by reference). In some embodiments, the analysis and presentation of results is also automated. For example, in some embodiments, software that generates a prognosis based on the presence or absence of a series of antigens is utilized.

Competitive binding assays rely on the ability of a labeled standard to compete with the test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample, which remain unbound.

Sandwich assays involve the use of two antibodies, each capable of binding to a different immunogenic portion, or epitope, or the protein to be detected. In a sandwich assay, the test sample to be analyzed is bound by a first antibody, which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more PCAST targets and the affinity value (Kd) is less than $1 \times 10^8$ M.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art.

For immunohistochemistry, the disease tissue sample may be fresh or frozen or may be embedded in paraffin and fixed with a preservative such as formalin (see Example). The fixed or embedded section contains the sample are contacted with a labeled primary antibody and secondary antibody, wherein the antibody is used to detect the PCAST protein express in situ. The detailed procedure is shown in the Example.

Array:

Array technologies and quantitative PCR provide the means to explore the expression profiles of a large number of related or unrelated genes, and proteins. When an expression profile is examined, arrays provide a platform for examining which genes or proteins are tissue-specific, carrying out housekeeping functions, parts of a signaling cascade, or specifically related to a particular genetic predisposition, condition, disease, or disorder. The potential application of gene or protein expression profiling is particularly relevant to improving diagnosis, prognosis, and treatment of disease. For example, both the sequences and the amount of expression can be compared between tissues from subjects with different types of pancreatic diseases and cytologically normal healthy tissue.

"Array" refers to an ordered arrangement of at least two transcripts, proteins or peptides, or antibodies on a substrate. At least one of the transcripts, proteins, or antibodies represents a control or standard, and the other transcript, protein, or antibody is of diagnostic or therapeutic interest. The arrangement of at least two and up to about 40,000 transcripts, proteins, or antibodies on the substrate assures that the size and signal intensity of each labeled complex, formed between each transcript and at least one nucleic acid, each protein and at least one ligand or antibody, or each antibody and at least one protein to which the antibody specifically binds, is individually distinguishable.

An "expression profile" is a representation of gene expression in a sample. A nucleic acid expression profile is produced using sequencing, hybridization, or amplification technologies using transcripts from a sample. A protein expression profile, although time delayed, mirrors the nucleic acid expression profile and is produced using gel electrophoresis, mass spectrometry, or an array and labeling moieties or antibodies which specifically bind the protein. The nucleic acids, proteins, or antibodies specifically binding the protein may be used in solution or attached to a substrate, and their detection is based on methods well known in the art.

A substrate includes but not limits to, paper, nylon or other type of membrane, filter, chip, glass slide, or any other suitable solid support.

The invention also provides an array with a cDNA or transcript encoding PCAST proteins or peptides or fragments thereof, antibodies, which specifically bind PCAST proteins, peptides or fragments thereof. Preferably, two or more of the nucleic acid molecules (e.g., SEQ ID NOS:24-39), proteins (e.g., SEQ ID NOS:1-23) or peptides (e.g., SEQ ID NOS:40-51) are immobilized on a substrate.

The present invention also provides an antibody array. Antibody arrays have allowed the development of techniques for high-throughput screening of recombinant antibodies. Such methods use robots to pick and grid bacteria containing antibody genes, and a filter-based ELISA to screen and identify clones that express antibody fragments. Because liquid handling is eliminated and the clones are arrayed from master stocks, the same antibodies can be spotted multiple times and screened against multiple antigens simultaneously. For more information, see de Wildt et al. (2000) Nat Biotechnol 18:989-94.

The array is prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), U.S. Pat. No. 5,807,522, Brown et al., all of which are incorporated herein in their entirety by reference.

In one embodiment, a nucleic acid array or a microarray, preferably composed of a large number of unique, single-stranded nucleic acid sequences, usually either synthetic antisense oligonucleotides or fragments of cDNAs, fixed to a solid support. The oligonucleotides are preferably about 6-60 nucleotides in length, more preferably 15-30 nucleotides in length, and most preferably about 20-25 nucleotides in length.

In order to produce oligonucleotides to a known sequence for an array, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations, it may be appropriate to use pairs of oligonucleotides on an array. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process, wherein the substrate may be paper, nylon or other type of membrane, filter, chip, glass slide or any other suitable solid support as described above.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference.

A gene expression profile comprises the expression of a plurality of transcripts as measured by after hybridization with a sample. The transcripts of the invention may be used as elements on an array to produce a gene expression profile. In one embodiment, the array is used to diagnose or monitor the progression of disease. Researchers can assess and catalog the differences in gene expression between healthy and diseased tissues or cells.

For example, the transcript or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human or nonmammal, with a transcript under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

By analyzing changes in patterns of gene expression, disease can be diagnosed at earlier stages before the patient is symptomatic. The invention can be used to formulate a prognosis and to design a treatment regimen. The invention can also be used to monitor the efficacy of treatment. For treatments with known side effects, the array is employed to improve the treatment regimen. A dosage is established that causes a change in genetic expression patterns indicative of successful treatment. Expression patterns associated with the onset of undesirable side effects are avoided.

In another embodiment, animal models which mimic a human disease can be used to characterize expression profiles associated with a particular condition, disease, or disorder; or treatment of the condition, disease, or disorder. Novel treatment regimens may be tested in these animal models using arrays to establish and then follow expression profiles over time. In addition, arrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

Treatment

The following terms, as used in the present specification and claims, are intended to have the meaning as defined below, unless indicated otherwise.

"Treat," "treating" or "treatment" of a disease includes: (1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of an agent that, when administered to a subject for treating a disease, is sufficient to effect such treatment for the disease. The "therapeutically effective amount" will vary depending on the agent, the disease and its severity and the age, weight, etc., of the subject to be treated.

A "pancreatic disease" includes pancreatic cancer, pancreatic tumor (exocrine or endocrine), pancreatic cysts, acute pancreatitis, chronic pancreatitis, diabetes (type I and II) as well as pancreatic trauma, prefereably pancreatic cancer.

A "cancer" is epithelial-cell related cancers include but not limite to pancreatic, lung, colon, prostate, ovarian, breast, bladder renal, hepatocellular, pharyngeal and gastric cancers.

The present invention provides an application of treatment by using antibody, immunogenic peptides as well as other PCAST agonists or antagonists.

PCASTs are proteins differentially expressed in the pancreatic diseases cell lines or tissues. The proteins are secreted pancreatic proteins (see the list in Table 1). These proteins are associated with the diseases especially pancreatic diseases, particularly pancreatic cancer; thus, they serve as candidate targets for the treatment of the diseases.

In one embodiment, when decreased expression or activity of the protein is desired, an inhibitor, antagonist, antibody and the like or a pharmaceutical agent containing one or more of these molecules may be delivered. Such delivery may be effected by methods well known in the art and may include delivery by an antibody specifically targeted to the protein. Neutralizing antibodies, which inhibit dimer formation, are generally preferred for therapeutic use.

In another embodiment, when increased expression or activity of the protein is desired, the protein, an agonist, an enhancer and the like or a pharmaceutical agent containing one or more of these molecules may be delivered. Such delivery may be effected by methods well known in the art and may include delivery of a pharmaceutical agent by an antibody specifically targeted to the protein.

Any of the transcripts, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Antibody Therapy

The antibody of the present invention can be used for therapeutic reason. It is contemplated that the antibody of the present invention may be used to treat a mammal, preferably human with pancreatic diseases.

In general, the antibodies are also useful for inhibiting protein function, for example, blocking the binding of the PCAST protein or peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated within a cell or cell membrane. The function blocking assays are provided in detail in the Examples. The antibodies of present invention can also be used as means of enhancing the immune response. The antibodies can be administered in amounts similar to those used for other therapeutic administrations of antibody. For example, pooled gamma globulin is administered at a range of about 1 mg to about 100 mg per patient. Thus, antibodies reactive with the protein or peptides of PCAST can be passively administered alone or in conjunction with other anti-cancer therapies to a mammal afflicted-with pancreatic diseases or cancer. Examples of anti-cancer therapies include, but are not limited to, chemotherapy, radiation therapy, adoptive immunotherapy therapy with TIL (Tumor Infiltration Lymphocytes).

The selection of an antibody subclass for therapy will depend upon the nature of the disease tumor antigen. For example, an IgM may be preferred in situations where the antigen is highly specific for the diseased target and rarely occurs on normal cells. However, where the disease-associated antigen is also expressed in normal tissues, although at much lower levels, the IgG subclass may be preferred for the following reason: since the binding of at least two IgG molecules in close proximity is required to activate complement, less complement mediated damage may occur in the normal tissues which express smaller amounts of the antigen and, therefore, bind fewer IgG antibody molecules. Furthermore, IgG molecules by being smaller may be more able than IgM molecules to localize to the diseased tissue.

The mechanism for antibody therapy is that the therapeutic antibody recognizes a cell surface protein or a cytosolic protein or secreted protein that is overexpressed in diseased cells. By NK cell or complement activation, conjugation of the antibody with an immunotoxin or radiolabel, the interaction can abrogate ligand/receptor interaction or activation of apoptosis.

The potential mechanisms of antibody-mediated cytotoxicity of diseased cells are phagocyte (antibody dependent cellular cytotoxicity (ADCC)) (see Example), complement (Complement-mediated cytotoxicity (CMC)) (see Example), naked antibody (receptor cross-linking apoptosis and growth factor inhibition), or targeted payload labeled with radionuclide or immunotoxins or immunochemotherapeutics.

In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

The antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody variant is suitably administered by pulse infusion, particularly with declining doses of the antibody variant. Preferably the dosing is given by injections, most preferably intravenous or subcutaneous injections, depending in part on whether the administration is brief or chronic.

For the prevention or treatment of a disease, the appropriate dosage of the antibody will depend on the type of disease to be treated, the severity and the course of the disease, whether the antibody is administered for preventive or therapeutic purposes, previous therapy, the patient's clinical history and response to the antibody, and the discretion of the attending physician.

Depending on the type and severity of the disease, about 1 .mu.g/kg to 150 mg/kg (e.g., 0.1-20 mg/kg) of antibody is an initial candidate dosage for administration to the patient, whether, for example, by one or more separate administrations, or by continuous infusion. A typical daily dosage might range from about 1 .mu.g/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutically effective amount of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question.

Antibodies of the present invention may also be used as therapeutic reagents, to diminish or eliminate cancer or tumors. For example, the antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas exotoxin*, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be affected, for example, through amino groups, carboxyl groups, sulfhydryl groups or oxidized carbohydrate residues. There are numerous references describing such methodology, e.g. U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways as described above.

While it is possible for the immunogen to be administered in a pure or substantially pure form, it is preferable to present it as a pharmaceutical composition, formulation or preparation with a carrier.

The formulations of the present invention, both for veterinary and for human use, comprise an immunogen as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may be conveniently presented in unit dosage form and may be prepared by any method well-known in the pharmaceutical art.

Suitable pharmaceutical carriers include proteins such as albumins (e.g., U.S. Pat. No. 4,507,234, to Kato et al.), peptides and polysaccharides such as aminodextran (e.g., U.S. Pat. No. 4,699,784, to Shih et al.), or water. A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, metal oxide, radionuclide. For example, U.S. Pat. No. 4,673,562, to Davison et al. discloses representative chelating compounds and their synthesis.

All methods include the step of bringing into association the active ingredient with the carrier, which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions, which are preferably isotonic with the blood of the recipient. Such formulations may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids, which may be used either on their own or as admixtures. These stabilizers are preferably incorporated in an amount of 0.11-10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8. In formulating the antibody of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the PCAST antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The therapeutic antibody may be supplied in the form of a kit, alone, or in the form of a pharmaceutical composition as described above.

Other Immunotherapy

The PCAST proteins or peptides or fragments thereof of this invention are also intended for use in producing antiserum designed for pre- or post-disease prophylaxis. Here the protein, peptides or fragment thereof, is formulated with a suitable adjuvant and administered by injection to human volunteers, according to known methods for producing human antisera. Antibody response to the injected proteins is monitored, during a several-week period following immunization, by periodic serum sampling to detect the presence of antiserum antibodies, using an immunoassay as described herein.

The antiserum from immunized individuals may be administered as a prophylactic measure for individuals who are at risk of developing pancreatic diseases or cancer. The antiserum is also useful in treating an individual afflicted with pancreatic diseases or cancer for post-disease prophylaxis.

Alternatively, peptides derived form the PCAST protein sequence may be modified to increase their immunogenicity by enhancing binding of the peptide to the MHC molecules in which the peptide is presented. The peptide or modified peptide may be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites, D. P. and Terr A. I. (eds) Appleton and Lange, Norwalk Conn., San Mateo, Calif.).

An "immunogenic peptide" is a peptide, which comprises an allele-specific motif such that the peptide will bind the MHC allele (HLA in human) and be capable of inducing a CTL (cytoxic T-lymphocytes) response. Thus, immunogenic peptides are capable of binding to an appropriate class I or II MHC molecule and inducing a cytotoxic T cell or T helper cell response against the antigen from which the immunogenic peptide is derived.

Alternatively, amino acid sequence variants of the peptide can be prepared by mutations in the DNA, which encodes the peptide, or by peptide synthesis.

At the genetic level, these variants ordinarily are prepared by site-directed mutagenesis of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

T-lymphocytes recognize antigen in association with Class I or Class II MHC molecules in the form of a peptide fragment bound to an MHC molecule. The degree of peptide binding to a given MHC allele is based on amino acids at particular positions within the peptide (Parker et al. (1992) Journal of Immunology 149:3580; Kubo, et al. (1994) Journal of Immunology 52:3913-3924; Ruppert J. et al. (1993) Cell 74:929-937; Falk et al. (1991) Nature 351:290-296). The peptides of the present invention are useful as an epitope for immunogenic response (see more detailed description below).

In human, MHC is called HLA, wherein class I molecules are encoded by the HLA-A, B, and C loci. HLA-A and B antigens are expressed at the cell surface at approximately equal densities, whereas the expression of HLA-C is significantly lower (about 10-fold lower). Each of these loci has a number of alleles. MHC class II molecules are encoded by three pairs of MHC II alpha- and beta-chain genes, called HLA DR, -DP, and -DQ in human. In many haplotypes the HLA-DR cluster contains an extra beta-chain gene whose product can pair with the DR alpha chain. Each MHC class I and II molecule binds a different rage of peptides. The present of several loci means that any one individual is equipped to present a much broader ranger of different peptides than if only one MHC protein of each class were expressed at the cell surface. The peptide binding motifs of the present invention are designed to be specific for each allelic subtype.

The peptides of the present invention are used for treatment of the pancreatic diseases. Treatment involves administration of the protective composition after the appearance of the disease.

The present invention is also applied to prevent and suppress the disease. It is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

The peptides are used for treating T cell-mediated pathology. The term "T cell-mediated pathology" refers to any condition in which an inappropriate T cell response is a component of the pathology. The term is intended to encompass both T cell mediated pancreatic diseases and diseases resulting from unregulated clonal T cell replication.

Therefore, the present invention relates to peptides or modified peptides derived from the protein sequences of the PCAST proteins that differentially expressed in the pancreatic diseases. By way of example, modification may include substitution, deletion or addition of an amino acid in the given immunogenic peptide sequence or mutation of existing amino acids within the given immunogenic peptide sequence, or derivatization of existing amino acids within the given immunogenic peptide sequence. Any amino acid comprising the immunogenic peptide sequence may be modified in accordance with this invention. In one aspect, at least one amino acid is substituted or replaced within the given immunogenic peptide sequence. Any amino acid may be used to substitute or replace a given amino acid within the immunogenic peptide sequence. Modified peptides are intended to include any immunogenic peptide obtained from differentially expressed proteins, which has been modified and exhibits enhanced binding to the MHC molecule with which it associates when presented to the T-cell. These modified peptides may be synthetically or recombinantly produced by conventional methods.

In another embodiment, the peptides of the present invention comprise, or consisting sequences of about 5-8, 8-10, 10-15 or 15-30 amino acids which are immunogenic, that is, capable of inducing an immune response when injected into a subject.

The recombinant or natural protein, peptides, or fragment thereof of PCAST, or modified peptides, may be used as a vaccine either prophylactically or therapeutically. When provided prophylactically the vaccine is provided in advance of any evidence of pancreatic diseases, particularly, cancer. The prophylactic administration of the pancreatic diseases vaccine should serve to prevent or attenuate pancreatic diseases, preferably cancer, in a mammal.

Preparation of Vaccine is Using Recombinant Protein or Peptide Expression vectors comprising all or part of nucleic acid sequence of PCAST proteins encoding peptides. Examples of vectors that may be used in the aforementioned vaccines include, but are not limited to, defective retroviral vectors, adenoviral vectors vaccinia viral vectors, fowl pox viral vectors, or other viral vectors (Mulligan, R. C., (1993) Science 260:926-932). The viral vectors carrying all or part of nucleic sequence of SEQ ID NOS:24-39 can be introduced into a mammal either prior to any evidence of pancreatic diseases or to mediate regression of the disease in a mammal afflicted with pancreatic diseases. Examples of methods for administering the viral vector into the mammals include, but are not limited to, exposure of cells to the virus ex vivo, or injection of the retrovirus or a producer cell line of the virus into the affected tissue or intravenous administration of the virus. Alternatively the viral vector carrying all or part of the PCAST nucleic acid sequence that encode peptides may be administered locally by direct injection into the cancer lesion or topical application in a pharmaceutically acceptable carrier. The quantity of viral vector, carrying all or part of the PCAST nucleic acid sequence, to be administered is based on the titer of virus particles. A preferred range of the immunogen to be administered may be about 106 to about 1011 virus particles per mammal, preferably a human. After immunization the efficacy of the vaccine can be assessed by production of antibodies or immune cells that recognize the antigen, as assessed by specific lytic activity or specific cytokine production or by tumor regression. One skilled in the art would know the conventional methods to assess the aforementioned parameters. If the mammal to be immunized is already afflicted with cancer, the vaccine can be administered in conjunction with other therapeutic treatments. Examples of other therapeutic treatments includes, but are not limited to, adoptive T cell immunotherapy, coadministration of cytokines or other therapeutic drugs for cancer.

Alternatively all or parts thereof of a substantially or partially purified the PCAST protein or their peptides may be administered as a vaccine in a pharmaceutically acceptable carrier. Ranges of the protein that may be administered are about 0.001 to about 100 mg per patient, preferred doses are about 0.01 to about 100 mg per patient. In a preferred embodiment, the peptides or modified peptides thereof is administered therapeutically or prophylactically to a mammal in need of such treatment. The peptide may be synthetically or recombinantly produced. Immunization is repeated as necessary, until a sufficient titer of anti-immunogen antibody or immune cells has been obtained.

In yet another alternative embodiment a viral vector, such as a retroviral vector, can be introduced into mammalian cells. Examples of mammalian cells into which the retroviral vector can be introduced include, but are not limited to, primary mammalian cultures or continuous mammalian cultures, COS cells, NIH3T3, or 293 cells (ATTC #CRL 1573), dendritic cells. The means by which the vector carrying the gene may be introduced into a cell includes, but is not limited to, microinjection, electroporation, transfection or transfection using DEAE dextran, lipofection, calcium phosphate or other procedures known to one skilled in the art (Sambrook et al. (EDS) (2001) in "Molecular Cloning. A laboratory manual", Cold Spring Harbor Press Plainview, N.Y.).

The vaccine formulation of the present invention comprises an immunogen that induces an immune response directed against the cancer associated antigens such as the PCASTs, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, cancer patients can be tested. Conventional methods would be used to evaluate the immune response of the patient to determine the efficiency of the vaccine.

Measurement of candidate disease tumor antigen or vaccine expression in patients is the first step of the present invention. Subsequent steps will focus on measuring immune responses to these candidate antigens or vaccine. Sera from disease patients, particularly cancer patients, and healthy donors will be screened for antibodies to the candidate antigens as well as for levels of circulating tumor derived antigens. antigen. The vaccine formulations may be evaluated first in animal models, initially rodents.

In one embodiment mammals, preferably human, at high risk for pancreatic diseases, particularly cancer, are prophylactically treated with the vaccines of this invention. Examples of such mammals include, but are not limited to, humans with a family history of pancreatic diseases, humans with a history of pancreatic diseases, particular cancer, or humans afflicted with pancreatic cancer previously resected and therefore at risk for reoccurrence. When provided therapeutically, the vaccine is provided to enhance the patient's own immune response to the diseased antigen present on the pancreatic diseases or advanced stage of pancreatic diseases. The vaccine, which acts as an immunogen, may be a cell, cell lysate from cells transfected with a recombinant expression vector, cell lysates from cells transfected with a recombinant expression vector, or a culture supernatant containing the expressed protein. Alternatively, the immunogen is a partially or substantially purified recombinant protein, peptide or analog thereof or modified peptides or analogs thereof. The proteins or peptides may be conjugated with lipoprotein or administered in liposomal form or with adjuvant.

While it is possible for the immunogen to be administered in a pure or substantially pure form, it is preferable to present it as a pharmaceutical composition, formulation or preparation. The formulations of the present invention are described in the previous section.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen also may be coupled with lipoproteins or administered in liposomal form or with adjuvants. The immunogen can be administered by any route-appropriate for antibody production such as intravenous, intraperitoneal, intramuscular, subcutaneous, and the like. The immunogen may be administered once or at periodic intervals until a significant titer of anti-PCAST immune cells or anti-PCAST antibody is produced. The presence of anti-PCAST immune cells may be assessed by measuring the frequency of precursor CTL (cytoxic T-lymphocytes) against PCAST antigen prior to and after immunization by a CTL precursor analysis assay (Coulie, P. et al., (1992) International Journal Of Cancer 50:289-297). The antibody may be detected in the serum using the immunoassay described above.

The safety of the immunization procedures is determined by looking for the effect of immunization on the general health of the immunized animal (weight change, fever, appetite behavior etc.) and looking for pathological changes on autopsies. After initial testing in animals, pancreatic diseases patients can be tested. Conventional methods would be used to evaluate the immune response of the patient to determine the efficiency of the vaccine.

In yet another embodiment of this invention all, part, or parts of the PCAST proteins or peptides or fragments thereof, or modified peptides, may be exposed to dendritic cells cultured in vitro. The cultured dendritic cells provide a means of producing T-cell dependent antigens comprised of dendritic cell modified antigen or dendritic cells pulsed with antigen, in which the antigen is processed and expressed on the antigen activated dendritic cell. The PCAST antigen activated dendritic cells or processed dendritic cell antigens may be used as immunogens for vaccines or for the treatment of pancreatic diseases, particularly pancreatic cancer. The dendritic cells should be exposed to antigen for sufficient time to allow the antigens to be internalized and presented on the dendritic cells surface. The resulting dendritic cells or the dendritic cell process antigens can than be administered to an individual in need of therapy. Such methods are described in Steinman et al. (WO93/208185) and in Banchereau et al. (EPO Application 0563485A1).

In yet another aspect of this invention T-cells isolated from individuals can be exposed to the PCAST proteins, peptides or fragment thereof, or modified peptides in vitro and then administered to a patient in need of such treatment in a therapeutically effective amount. Examples of where T-lymphocytes can be isolated include but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami, Y. et al. (1989) J. Immunol. 142: 2453-3461). Lymphocytes are cultured in media such as RPMI or RPMI 1640 or AIM V for 1-10 weeks. Viability is assessed by trypan blue dye exclusion assay. Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A. et al. (1992) Human Gene Therapy, 3: 75-90; Rosenberg, S. A. et al. (1992) Human Gene Therapy, 3: 57-73).

The present invention is further described by the following example. The example is provided solely to illustrate the invention by reference to specific embodiments. This exemplification, while illustrating certain aspects of the invention, does not offer the limitations or circumscribe the scope of the disclosed invention.

All examples outlined here were carried out using standard techniques, which are well known and routine to those of skill in the art. Routine molecular biology techniques of the following example can be carried out as described in standard laboratory manuals, such as Sambrook et al., Molecular Cloning: A laboratory Manual, 3rd Ed.; Cold Spring Harbor Laboratory, Cold Spring Harbor, N.Y. (2001).

WORKING EXAMPLES

1. Pancreatic Cell Line Model System

Analysis of gene expression in various pancreatic cancer cell lines as well as pancreatic duct epithelial tissue has shown that the cell line Hs766T correlates well with normal tissue. For this reason, this cell line is reported in the literature as being a good surrogate for normal tissue in analyses of differential expression between pancreatic adenomcarcinoma (and derived tumor lines) and normal tissue (or surrogate, Hs766T). The model system employed here involves the use of Hs766T as a "normal" reference to which secreted expression in tumor-derived cell lines is compared. These differentials or candidates are then validated in tissues, pancreatic cancer and normal pancreas, to confirm that they are differentially expressed between these tissues as well as within the cell line model system. Details of the pancreatic tumor lines that were used for this study, as well as the pancreatic line Hs766T are provided below.

Cell Lines and Media:

| Cell line | ATCC Reference | Base medium | Glutamine | Non-essential amino acids | Sodium Carbonate | Sodium Pyruvate | Hepes | Fetal Bovine Serum |
|---|---|---|---|---|---|---|---|---|
| Panc-1 | CRL-1469 | DMEM | 2 mM | 1% (w/v) | 0.1% (w/v) | 1 mM | | 10% (v/v) |
| Hs766t | HTB-134 | DMEM | 2 mM | 1% (w/v) | 0.1% (w/v) | 1 mM | | 10% (v/v) |
| SU.86.86 | CRL-1837 | DMEM | 2 mM | 1% (w/v) | 0.1% (w/v) | 1 mM | | 10% (v/v) |
| AsPC1 | CRL-1682 | RPMI | 2 mM | 1% (w/v) | 0.1% (w/v) | 1 mM | 10 mM | 20% (v/v) |
| HPAF II | CRL-1997 | DMEM | 2 mM | 1% (w/v) | 0.1% (w/v) | 1 mM | | 10% (v/v) |
| HPAC | CRL-2119 | DMEM | 2 mM | 1% (w/v) | 0.1% (w/v) | 1 mM | | 10% (v/v) |
| Mia-Paca-2 | CRL-1420 | DMEM | 2 mM | 1% (w/v) | 0.1% (w/v) | 1 mM | | 10% (v/v) |
| Mpanc-96 | CRL-2380 | RPMI | 2 mM | 1% (w/v) | 0.1% (w/v) | 1 mM | 10 mM | 10% (v/v) |
| BxPC-3 | CRL-1687 | RPMI | 2 mM | 1% (w/v) | 0.1% (w/v) | 1 mM | 10 mM | 10% (v/v) |
| Capan-2 | HTB-80 | DMEM | 2 mM | 1% (w/v) | 0.1% (w/v) | 1 mM | | 10% (v/v) |

Pancreatic cancer cell line culture

Cells are grown under routine tissue culture conditions in 490 cm$^2$ roller bottles at an initial seeding density of approximately 15 million cells per roller bottle. When the cells reach ~70-80% confluence, the culturing media was removed, the cells were washed 3 times with D-PBS and once with CD293 protein-free media (Invitrogen cat# 11913-019), and the culturing media was replaced with CD293 for generating conditioned media. Cells were incubated for 72 hours in CD293 and the media was collected for secreted protein MS analysis (30-300 ml). Cell debris was removed from the conditioned media by centrifugation at 300 g for 5 minutes and filtering through a 0.2 micron filter prior to MS analysis.

To monitor cell proliferation and apoptosis, the remaining cells were incubated with 1:100 dilution of BrdU in culturing media for 2 hours (BrdU Flow Kit cat# 559619 BD Biosciences). Cells were washed 3 times with D-PBS and disassociated from the flask with versene. Cells were washed once with Flow Staining Buffer (0.5% BSA, 0.05% NaN$_3$ in D-PBS). Cells were incubated with 400 ul of Cytofix/Cytoperm Buffer (BrdU Flow Kit BD Biosciences)

for 15-30 minutes at 4° C. Cells were washed once with Flow Staining Buffer and resuspended in 400 ul Cytoperm Plus Buffer (BrdU Flow Kit BD Biosciences). Cells were incubated for 10 minutes at 4° C. and washed once with 1× Perm/Wash Buffer (BrdU Flow Kit BD Biosciences). Cells were incubated for 1 hour at 37° C. protected from light in DNAse solution (BrdU Flow Kit BD Biosciences). Cells were washed once with 1× Perm/Wash Buffer and incubated for 20 minutes at room temperature with anti-BrdU FITC conjugated antibody (BrdU Flow Kit BD Biosciences) and PE-conjugated active caspase 3 (BD Biosciences cat# 550821) and PE mouse IgG2B isotype control. Cells were washed once with 1× Perm/Wash Buffer and resuspended in DAPI for LSR flow cytometry analysis.

2. Cloning and Expression of Target Proteins cDNA Retrieval

Peptide sequences were searched by BlastP against the Celera Discovery System (CDS) and public database to identify the corresponding full-length open reading frames (ORFs). Each ORF sequence was then searched by BlastN against the Celera in-house human cDNA clone collection. For each sequence of interest, up to three clones are pulled and streaked onto LB/Ampicillin (10 ug/ml) plates. Plasmid DNA is isolated using Qiagen spin mini-prep kit and verified by restriction digest. Subsequently, the isolated plasmid DNA is sequence verified against the ORF reference sequence. Sequencing reactions are carried out using Applied Biosystems BigDye Terminator kit followed by ethanol precipitation. Sequence data is collected using the Applied Biosystems 3100 Genetic Analyzer and analyzed by alignment to the reference sequence using the Clone Manager alignment tool.

PCR

PCR primers are designed to amplify the full-length ORF as well as any regions of the ORF that are interest for expression (antigenic or hydrophilic regions as determined by the Clone Manager sequence analysis tool). Primers also contain 5' and 3' overhangs to facilitate cloning (see below). PCR reactions contain 2.5 units Platinum Taq DNA Polymerase High Fidelity (Invitrogen), 50 ng cDNA plasmid template, 1 uM forward and reverse primers, 800 uM dNTP cocktail (Applied Biosystems) and 2 mM MgSO4. After 20-30 cycles (94° C. for 30 seconds, 55° C. for 1 minutes and 73° C. for 2 minutes), product is verified and quantitated by agarose gel electrophoresis.

Construction of Entry Clones

PCR products are cloned into an entry vector for use with the Gateway recombination based cloning system (Invitrogen). These vectors included pDonr221, pDonr201, pEntr/D-TOPO or pEntr/SD/D-TOPO and are used as described in the cloning methods below.

TOPO Cloning Into pEntr/D-TOPO or pEntr/SD/D-TOPO

For cloning using this method, the forward PCR primer contain a 5' overhang containing the sequence "CACC". PCR products are generated as described above and cloned into the entry vector using the Invitrogen TOPO cloning kit. Reactions are typically carried out at room temperature for 10 minutes and subsequently transformed into TOP10 chemically competent cells (Invitrogen, CA). Candidate clones are picked, plasmid DNA is prepared using Qiagen spin mini-prep kit and screened using restriction digest. Inserts are subsequently sequence verified as described above.

Gateway Cloning into pDonr201 or pDonr221

For cloning using this method, PCR primers contain the following overhangs:

Forward 5' overhang:
5'-GGGGACAAGTTTGTACAAAAAAGCAGGCTTC-3'

Reverse 5' overhang:
5'-GGGGACCACTTTGTACAAGAAAGCTGGGT-3'

PCR products are generated as described above. ORFs are recombined into the entry vector using the Invitrogen Gateway BP Clonase enzyme mix. Reactions are typically carried out at 25° C. for 1 hour, treated with Proteinase K at 37° C. for 10 minutes and transformed into Library Efficiency DH5α chemically competent cells (Invitrogen, CA). Candidate clones are picked, plasmid DNA is prepared using Qiagen spin mini-prep kit and screened using restriction digest. Inserts are subsequently sequence verified as described above.

Construction of Expression Clones

ORFs are transferred from the entry construct into a series of expression vectors using the Gateway LR Clonase enzyme mix. Reactions are typically carried out for 1 hour at 25° C., treated with Proteinase K at 37° C. for 10 minutes and subsequently transformed into Library Efficiency DH5α chemically competent cells (Invitrogen). Candidate clones are picked, plasmid DNA is prepared using Qiagen spin mini-prep kit and screened using restriction digest. Expression vectors include but are not limited to pDest14, pDest15, pDest17, pDest8, pDest10 and pDest20. These vectors allow expression in systems such as E. coli and recombinant baculovirus. Other vectors not listed here allow expression in yeast, mammalian cells, or in vitro.

Expression of Recombinant Proteins in E. coli

Constructs are transformed into one or more of the following host strains: BL21 SI, BL21 AI, (Invitrogen); Origami B (DE3), Origami B (DE3) pLysS, Rosetta (DE3), Rosetta (DE3) pLysS, Rosetta-Gami (DE3), Rosetta-Gami (DE3) pLysS, or Rosetta-Gami B (DE3) pLysS (Novagen). The transformants are grown in LB with or without NaCl and with appropriate antibiotics, at temperatures in the range of 20-37° C., with aeration. Expression is induced with the addition of IPTG (0.03-0.3 mM) or NaCl (75-300 mM) when the cells are in mid-log growth. Growth is continued for one to 24 hours post-induction. Cells are harvested by centrifugation in a Sorvall RC-3C centrifuge in a H6000A rotor for 10 minutes at 3000 rpm, at 4° C. Cell pellets are stored at −80° C.

Expression of Recombinant Proteins Using Baculovirus

Recombinant proteins are expressed using baculovirus in Sf21 fall army worm ovarian cells. Recombinant baculoviruses are prepared using the Bac-to-Bac system (Invitrogen) per the manufacturer's instructions. Proteins are expressed on the large scale in Sf900II serum-free medium (Invitrogen) in a 10 L bioreactor tank (27° C., 130 rpm, 50% dissolved oxygen for 48 hours).

3. Recombinant Protein Purification

Recombinant proteins are purified from E. coli and/or insect cells using a variety of standard chromatography methods. Briefly, cells are lysed using sonication or detergents. The insoluble material is pelleted by centrifugation at 10,000Xg for 15 minutes. The supernatant is applied to an appropriate affinity column, e.g. His-tagged proteins are separated using a pre-packed chelating sepharose column (Pharmacia) or GST-tagged proteins are separated using a glutathione sepharose column (Pharmacia). After using the affinity column, proteins are further separated using various techniques, such as ion exchange chromatography (columns from Pharmacia) to separate on the basis of electrical charge or size exclusion chromatography (columns from Tosohaas) to separate on the basis of molecular weight, size and shape.

Expression and purification of the protein are also achieved using either a mammalian cell expression system or an insect cell expression system. The pUB6/V5-His vector system (Invitrogen, CA) is used to express GSCC in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6.times.His) sequence for rapid purification on PROBOND resin (Invitrogen, CA). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6×his which enables purification as described above. Purified protein is used in the following activity and to make antibodies

4. Chemical Synthesis of Peptides

Proteins or portions thereof may be produced not only by recombinant methods, but also by using chemical methods well known in the art. Solid phase peptide synthesis may be carried out in a batchwise or continuous flow process, which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-a-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivatized amino acids, and washing with dichloromethane and/or N,N-dimethylformamide. The peptide is cleaved between the peptide carboxy terminus and the linker group to yield a peptide acid, or amide. (Novabiochem 1997/98 Catalog and Peptide Synthesis Handbook, San Diego Calif. pp. S1-S20). Automated synthesis may also be carried out on machines such as the 431A peptide synthesizer (ABI). A protein or portion thereof may be purified by preparative high performance liquid chromatography and its composition confirmed by amino acid analysis or by sequencing (Creighton (1984) Proteins, Structures and Molecular Properties, W H Freeman, New York N.Y.).

5. Antibody Development

Polyclonal Antibody Preparations:

Polyclonal antibodies against recombinant proteins are raised in rabbits (Green Mountain Antibodies, Burlington, Vt.). Briefly, two New Zealand rabbits are immunized with 0.1 mg of antigen in complete Freund's adjuvant. Subsequent immunizations are carried out using 0.05 mg of antigen in incomplete Freund's adjuvant at days 14, 21 and 49. Bleeds are collected and screened for recognition of the antigen by solid phase ELISA and western blot analysis. The IgG fraction is separated by centrifugation at 20,000Xg for 20 minutes followed by a 50% ammonium sulfate cut. The pelleted protein is resuspended in 5 mM Tris and separated by ion exchange chromatography. Fractions are pooled based on IgG content. Antigen-specific antibody is affinity purified using Pierce AminoLink resin coupled to the appropriate antigen.

Isolation of Antibody Fragments Directed Against PCASTs from a Library of scFvs

Naturally occurring V-genes isolated from human PBLs are constructed into a library of antibody fragments which contain reactivities against PCAST to which the donor may or may not have been exposed (see e.g., U.S. Pat. No. 5,885,793 incorporated herein by reference in its entirety).

Rescue of the Library: A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 .mu.g/ml of ampicillin (2.times.TY-AMP-GLU) and grown to an O.D. of 0.8 with shaking. Five ml of this culture is used to innoculate 50 ml of 2.times.TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 .mu.g/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 .mu.g ampicillin/ml and 25 .mu.g kanamycin/ml (2×TY-AMP-KAN) and grown overnight, shaking at 37° C. Phagre particles are purified and concentrated from the culture medium by two PEG-precipitations ($3^{rd}$ edition of Sambrook et al. (2001)), resuspended in 2 ml PBS and passed through a 0.45 .mu.m filter (Minisart NML; Sartorius) to give a final concentration of approximately 1013 transducing units/ml (ampicillin-resistant clones).

Panning of the Library: Immunotubes (Nunc) are coated overnight in PBS with 4 ml of either 100 .mu.g/ml or 10 .mu.g/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phages are then used to infect 10 ml of mid-log *E. coli* TG1 by incubating eluted phage with bacteria for 30 minutes at 37° C. The *E. coli* are then plated on TYE plates containing 1% glucose and 100 .mu.g/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders: Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 .mu.g/ml of the polypeptide of the present invention in 50 mM bicarbonate pH 9.6. Clones positive in ELISA are further characterized by PCR fingerprinting (see, e.g., PCT publication WO 92/01047) and then by sequencing.

Monoclonal Antibody Generation i) Materials: 1) Complete Media No Sera (CMNS) for washing of the myeloma and spleen cells; Hybridoma medium CM-HAT {Cell Mab (BD), 10% FBS (or HS); 5% Origen HCF (hybridoma cloning factor) containing 4 mM L-glutamine and antibiotics} to be used for plating hybridomas after the fusion. 2) Hybridoma medium CM-HT (NO AMINOPTERIN) (Cell Mab (BD), 10% FBS 5% Origen HCF containing 4 mM L-glutamine and antibiotics) to be used for fusion maintenance are stored in the refrigerator at 4-6° C. The fusions are fed on days 4, 8, and 12, and subsequent passages. Inactivated and pre-filtered commercial Fetal Bovine serum (FBS) or Horse Serum (HS) are thawed and stored in the refrigerator at 4° C. and must be pretested for myeloma growth from single cells. 3) The L-glutamine (200 mM, 100× solution), which is stored at −20° C. freezer, is thawed and warmed until completely in solution. The L-glutamin is dispensed into media to supplement growth. L-glutamin is added to 2 mM for myelomas, and 4 mM for hybridoma media. Further the Penicillin, Streptomycin, Amphotericin (antibacterial-antifungal solution at −20° C.) is thawed and added to Cell Mab Media to 1%. 4) Myeloma growth media is Cell Mab Media (Cell Mab Media, Quantum Yield from BD is stored in the refrigerator at 4° C. in the dark) which are added L-glutamine to 2 mM and antibiotic/antimycotic solution to 1% and is called CMNS. 5) 1 bottle of PEG 1500 in Hepes (Roche, N.J.). 6) 8-Azaguanine is stored as the dried powder supplied by SIGMA at −700° C. until needed. Reconstitute 1 vial/500 ml of media and add entire contents to 500 ml media (eg. 2 vials/liter). 7) Myeloma Media is CM which has 10% FBS (or HS) and 8-Aza (1×) stored in the refrigerator at 4° C. 8) Clonal cell medium D (Stemcell, Vancouver) contains HAT and methyl cellulose for semi-solid direct cloning from the fusion. This comes in 90 ml bottles with a CoA and must be "melted at 37° C. in a waterbath in the morning of the day of the fusion. Loosen the cap and leave in $CO_2$ incubator to sufficiently gas the medium D and bring the pH down. 9) Hybridoma supplements HT [hypoxanthine, thymidine] are to be used in medium for the section of hybridomas and maintenance of hybridomas through the cloning stages respectively. 10) Origen HCF can be obtained directly from Igen and is a cell supernatant produced from a macrophage-like cell-line. It can be thawed and aliqouted to 15 ml tubes at 5 ml per tube and stored frozen at −20° C. Positive Hybridomas are fed HCF through the first subcloning and are gradually weaned. It is not necessary to continue to supplement unless you have a particularly difficult hybridoma clone. This and other additives have been shown to be more effective in promoting new hybridoma growth than conventional feeder layers.

ii) Procedure

To generate monoclonal antibodies, mice are immunized with 5-50 ug of antigen either intra-peritoneally (i.p.) or by intravenous injection in the tail vein (i.v.). Typically, the antigen used is a recombinant protein that is generated as described above. The primary immunization takes place 2 months prior to the harvesting of splenocytes from the mouse and the immunization is typically boosted by i.v. injection of 5-50 ug of antigen every two weeks. At least one week prior to expected fusion date, a fresh vial of myeloma cells is thawed and cultured. Several flasks at different densities are maintained in order that a culture at the optimum density is ensured at the time of fusion. The optimum density is determined to be $3-6 \times 10^5$ cells/ml. Two to five days before the scheduled fusion, a final immunization is administered of ~5 ug of antigen in PBS i.p. or i.v.

Myeloma cells are washed with 30 ml serum free media by centrifugation at 500 g at 4° C. for 5 minutes. Viable cell density is determined in resuspended cells using hemocytometry and vital stains. Cells resuspended in complete growth medium are stored at 37° C. during the preparation of splenocytes. Meanwhile, to test aminopterin sensitivity, $1 \times 10^6$ myeloma cells are transferred to a 15 ml conical tube and centrifuged at 500 g at 4° C. for 5 minutes. The resulting pellet is resuspended in 15 ml of HAT media and cells plated at 2 drops/well on a 96 well plate.

To prepare splenocytes from immunized mice, the animals are euthanized and submerged in 70% ETOH. Under sterile conditions, the spleen is surgically removed and placed in 10 ml of RPMI medium supplemented with 20% fetal calf serum in a Petri dish. Cells are extricated from the spleen by infusing the organ with medium >50 times using a 21 g syringe.

Cells are harvested and washed by centrifugation (at 500 g at 4° C. for 5 minutes) with 30 ml of medium. Cells are resuspended in 10 ml of medium and the density of viable cells determined by hemocytometry using vital stains. The splenocytes are mixed with myeloma cells at a ratio of 5:1 (spleen cells: myeloma cells). Both the myeloma and spleen cells are washed 2 more times with 30 ml of RPMI-CMNS. Spin at 800 rpm for 12 minutes.

Supernatant is removed and cells are resuspended in 5 ml of RPMI-CMNS and are pooled to fill volume to 30 ml and spin down as before. Then, the pellet is broken up by gently tapping on the flow hood surface and resuspended in 1 ml of BMB REG1500 (prewarmed to 37° C.) dropwise with 1 cc needle over 1 minute.

RPMI-CMNS to the PEG cells and RPMI-CMNS are added to slowly dilute out the PEG. Cells are centrifuged and diluted in 5 ml of Complete media and 95 ml of Clonacell Medium D (HAT) media (with 5 ml of HCF). The cells are plated out 10 ml per small petri plate.

Myeloma/HAT control. P is prepared as follows: dilute about 1000 P3X63 Ag8.653 myeloma cells into 1 ml of mediu D and transfer into a single well of a 24 well plate. Plates are placed in incubator, with two plates inside of a large petri plate, with an additional petri plate full of distilled water, for 10-18 days under 5% CO2 overlay at 37° C. Clones are picked from semisolid agarose into 96 well plates containing 150-200 ul of CM-HT. Supernatants are screened 4 days later in ELISA, and positive clones are moved up to 24 well plates. Heavy growth will require changing of the media at day 8 (+/150 ml). One should further decrease the HCF to 0.5% (gradually-2%, then 1%, then 0.5%) in the cloning plates.

For further references see Kohler G, and C. Milstein Continuous cultures of fused cells secreting antibody of predefined specificity. 1975. Nature 256: 495-497; Lane, R. D. A short duration polyethylene glycol fusion technique for increasing production of monoclonal antibody-secreting hybridomas. 1985. J. Immunol. Meth. 81:223-228; Harlow, E. and D. Lane. Antibodies: A laboratory manual. Cold Spring Harbour Laboratory Press. 1988; Kubitz, D. The Scripps Research Institute. La Jolla. Personal Communication; Zhong, G., Berry, J. D., and Choukri, S. (1996) Mapping epitopes of Chlamydia trachomatis neutralizing monoclonal antibodies using phage random peptide libraries. J. Indust. Microbiol. Biotech. 19, 71-76; Berry, J. D., Licea, A., Popkov, M., Cortez, X., Fuller, R., Elia, M., Kerwin, L., and C. F. Barbas III. (2003) Rapid monoclonal antibody generation via dendritic cell targeting in vivo. Hybridoma and Hybridomics 22 (1), 23-31.

6. Expression Validation mRNA Expression Validation by Taqman

Expression of mRNA is quantitated by RT-PCR using TaqMan® technology. The Taqman system couples a 5' fluorogenic nuclease assay with PCR for real time quantitation. A probe is used to monitor the formation of the amplification product.

Total RNA is isolated from cancer model cell lines using the RNEasy kit® (Qiagen) per manufacturer's instructions and included DNase treatment. Normal human tissue RNAs are acquired from commercial vendors (Ambion, Austin, Tex.; Stratagene, La Jolla, Calif.; BioChain Institute, Newington, N.H.) as are RNAs from matched disease/normal tissues.

Target transcript sequences are identified for the differentially expressed peptides by searching the BlastP database. TaqMan assays (PCR primer/probe set) specific for those transcripts are identified by searching the Celera Discovery System™ (CDS) database. The assays are designed to span exon-exon borders and do not amplify genomic DNA.

The TaqMan primers and probe sequences are as designed by Applied Biosystems (AB) as part of the Assays on Demand™ product line or by custom design through the AB Assays by Designs$^{SM}$ service.

RT-PCR is accomplished using AmpliTaqGold and MultiScribe reverse transcriptase in the One Step RT-PCR Master Mix reagent kit (AB) according to the manufacturer's instructions. Probe and primer concentrations are 250 nM and 900 nM, respectively, in a 15 µl reaction. For each experiment, a master mix of the above components is made and aliquoted into each optical reaction well. Eight nanograms of total RNA is the template. Each sample is assayed in triplicate. Quantitative RT-PCR is performed using the ABI Prism® 7900HT Sequence Detection System (SDS). Cycling parameters follow: 48° C. for 30 min. for one cycle; 95° C. for 10 min for one cycle; 95° C. for 15 sec, 60° C. for 1 min. for 40 cycles.

The SDS software calculates the threshold cycle ($C_T$) for each reaction, and $C_T$ values are used to quantitate the relative amount of starting template in the reaction. The $C_T$ values for each set of three reactions are averaged for all subsequent calculations.

Data are analyzed for fold difference in expression using an endogenous control for normalization and is expressed relative to a normal tissue or normal cell line reference. The choice of endogenous control is determined empirically by testing various candidates against the cell line and tissue RNA panels and selecting the one with the least variation in expression. Relative changes in expression are quantitated using the $2^{-\Delta\Delta C_T}$ Method. Livak, K. J. and Schmittgen, T. D. (2001) Methods 25: 402-408; User bulletin #2: ABI Prism 7700 Sequence Detection System.

Protein Expression Validation by Western

Western blot analysis of target proteins is carried out using whole cell extracts prepared from each of the pancreatic cell lines. To make cell extracts, the cells are resuspended in Lysis buffer (125 mM Tris, pH 7.5, 150 mM NaCl, 2% SDS, 5 mM EDTA, 0.5% NP-40) and passed through a 20-gauge needle. Lysates are centrifuged at 5,000Xg for 5 minutes at 4° C. The supernatants are collected and a protease inhibitor cocktail (Sigma) is added. The Pierce BCA assay is used to quantitate total protein. Samples are separated by SDS-PAGE and transferred to either a nitrocellulose or PVDF membrane. The Western Breeze kit from Invitrogen is used for western blot analysis. Primary antibodies are either purchased from commercially available sources or prepared as using one of the methods described in section 5. For this application, antibodies are typically diluted 1:500 to 1:10,000 in diluent buffer. Blots are developed using Pierce NBT.

Tissue Flow Cytometry Analysis

Post tissue processing, cells are sorted by flow cytometry known in the art to enrich for epithelial cells. Alternatively, cells isolated from pancreatic tissue are stained directly with EpCAM (for epithelial cells) and the specific antibody to PCAST. Cell numbers and viability are determined by PI exclusion (GUAVA) for cells isolated from both normal and tumor pancreatic tissue. A minimum of 0.5×106 cells are used for each analysis. Cells are washed once with Flow Staining Buffer (0.5% BSA, 0.05% NaN$_3$ in D-PBS). To the cells, 20 ul of each antibody for PCAST are added. An additional 5 ul of EpCAM antibody conjugated to APC are added when unsorted cells are used in the experiment. Cells are incubated with antibodies for 30 minutes at 4° C. Cells are washed once with Flow Staining Buffer and either analyzed immediately on the LSR flow cytometry apparatus or fixed in 1% formaldehyde and store at 4° C. until LSR analysis. The antibodies used to detect PCAST targets are all purchased by BD Biosciences and PE-conjugated. The isotype control antibody used for these experiments is PE-conjugated mouse IgG1k.

Tumors tissue from pancreatic cancer and from Xenograft mouse pancreatic tissues are obtained and detected via Flow Cytometry analysis. Tissue factor is shown to be overexpressed among the pancreatic tumor tissues. Xenograft mouse is obtained by using cultured human BXPC pancreatic cells (ATCC) that are injected subcutaneously in BALB nude mouse. The pancreatic tumors are obtained from the xenograft mouse for further FACS study.

7. Detection and Diagnosis of PCAST by Liquid Chromatography and Mass Spectrometry (LC/MS)

The proteins secreted from cells can be prepared by reduction, alkylation and cysteine-containing peptide enrichment of concentrated conditioned media.

The differential expression of proteins in disease and healthy samples are quantitated using Liquid Chromatography Mass Spectrometry. The LC/MS spectra from disease and healthy (control) samples are collected and processed using the following steps:

The raw scans from the LC/MS instrument are subjected to peak detection and noise reduction software. Filtered peak lists are then used to detect 'features' corresponding to specific peptides from the original sample(s). Features are characterized by their mass/charge, charge, retention time, isotope pattern and intensity.

Similar experiments are repeated in order to increase the confidence in detection of a peptide. These multiple acquisitions are computationally aggregated into one experiment. The intensity of a peptide present in both healthy and disease samples is used to calculate the differential expression, or relative abundance, of the peptide. The intensity of a peptide found exclusively in one sample is used to calculate a theoretical expression ratio for that peptide (singleton). Expression ratios are calculated for each peptide of each replicate of the experiment.

Statistical tests are performed to assess the robustness of the data and select statistically significant differentials. To assess general quality of the data, a) ensured that similar features are detected in all replicates of the experiment; b) number of matched ions between replicates; c) calculated the overall pair wise intensity correlations between LC/MS maps of process replicates to ensure that the expression ratios for peptides are reproducible across the multiple replicates; d) aggregated multiple experiments in order to compare the expression ratio of a peptide in multiple diseases or disease samples.

8. Expression Validation by IHC in Tissue Sections

Tissue Sections

Paraffin embedded, fixed tissue sections are obtained from a panel of normal tissues (Adrenal, Bladder, Lymphocytes, Bone Marrow, Breast, Cerebellum, Cerebral cortex, Colon, Endothelium, Eye, Fallopian tube, Small Intestine, Heart, Kidney [glomerulus, tubule], Liver, Lung, Testes and Thyroid) as well as 30 tumor samples with matched normal adjacent tissues from pancreas, lung, colon, prostate, ovarian and breast. In addition, other tissues are selected for testing such as bladder renal, hepatocellular, pharyngeal and gastric tumor tissues.

Esophageal Replicate sections are also obtained from numerous tumor types (Bladder Cancer, Lung Cancer, Breast Cancer, Melanoma, Colon Cancer, Non-Hodgkins Lymphoma, Endometrial Cancer, Ovarian Cancer, Head and Neck Cancer, Prostate Cancer, Leukemia [ALL and CML] and Rectal Cancer). Sections are stained with hemotoxylin and eosin and histologically examined to ensure adequate representation of cell types in each tissue section.

An identical set of tissues will be obtained from frozen sections and are used in those instances where it is not possible to generate antibodies that are suitable for fixed sections. Frozen tissues do not require an antigen retrieval step.

Paraffin Fixed Tissue Sections

Hemotoxylin and Eosin staining of paraffin embedded, fixed tissue sections. Sections are deparaffinized in 3 changes of xylene or xylene substitute for 2-5 minutes each. Sections are rinsed in 2 changes of absolute alcohol for 1-2 minutes each, in 95% alcohol for 1 minute, followed by 80% alcohol for 1 minute. Slides are washed well in running water and stained in Gill solution 3 hemotoxylin for 3 to 5 minutes. Following a vigorous wash in running water for 1 minute, sections are stained in Scott's solution for 2 minutes. Sections are washed for 1 min in running water then conterstained in Eosin solution for 2-3 minutes depending upon development of desired staining intensity. Following a brief wash in 95% alcohol, sections are dehydrated in three changes of absolute alcohol for 1 minute each and three changes of xylene or xylene substitute for 1-2 minutes each. Slides are coverslipped and stored for analysis.

Optimisation of Antibody Staining

For each antibody, a positive and negative control sample is generated using data from the ICAT analysis of the pancreatic cancer cell lines. Cell lines are selected that are known to express low levels of a particular target as determined from the ICAT data. This cell line is the reference normal control "Hs766T". Similarly, a pancreatic tumour line is selected that is determined to overexpress the target is selected.

Antigen Retrieval

Sections are deparaffinized and rehydrated by washing 3 times for 5 minutes in xylene; two times for 5 minutes in 100% ethanol; two times for 5 minutes in 95% ethanol; and once for 5 minutes in 80% ethanol. Sections are then placed in endogenous blocking solution (methanol+2% hydrogen peroxide) and incubated for 20 minutes at room temperature. Sections are rinsed twice for 5 minutes each in deionized water and twice for 5 minutes in phosphate buffered saline (PBS), pH 7.4. Alternatively, where necessary sections are deparrafinized by High Energy Antigen Retrieval as follows: sections are washed three times for 5 minutes in xylene; two times for 5 minutes in 100% ethanol; two times for 5 minutes in 95% ethanol; and once for 5 minutes in 80% ethanol. Sections are placed in a Coplin jar with dilute antigen retrieval solution (10 mM citrate acid, pH 6). The Coplin jar containing slides is placed in a vessel filled with water and microwaved on high for 2-3 minutes (700 watt oven). Following cooling for 2-3 minutes, steps 3 and 4 are repeated four times (depending on tissue), followed by cooling for 20 minutes at room temperature. Sections are then rinsed in deionized water, two times for 5 minutes, placed in modified endogenous oxidation blocking solution (PBS+2% hydrogen peroxide) and rinsed for 5 minutes in PBS.

Blocking and Staining

Sections are blocked with PBS/1% bovine serum albumin (PBA) for 1 hour at room temperature followed by incubation in normal serum diluted in PBA (2%) for 30 minutes at room temperature to reduce non-specific binding of antibody. Incubations are performed in a sealed humidity chamber to prevent air-drying of the tissue sections. (The choice of blocking serum is the same as the species of the biotinylated secondary antibody). Excess antibody is gently removed by shaking and sections covered with primary antibody diluted in PBA and incubated either at room temperature for 1 hour or overnight at 4° C. (Care is taken that the sections do not touch during incubation). Sections are rinsed twice for 5 minutes in PBS, shaking gently. Excess PBS is removed by gently shaking. The sections are covered with diluted biotinylated secondary antibody in PBA and incubated for 30 minutes to 1 hour at room temperature in the humidity chamber. If using a monoclonal primary antibody, addition of 2% rat serum is used to decrease the background on rat tissue sections. Following incubation, sections are rinsed twice for 5 minutes in PBS, shaking gently. Excess PBS is removed and sections incubated for 1 hour at room temperature in Vectastain ABC reagent (as per kit instructions). The lid of the humidity chamber is secured during all incunations to ensure a moist environment. Sections are rinsed twice for 5 minutes in PBS, shaking gently.

Develop and Counterstain

Sections are incubated for 2 minutes in peroxidase substrate solution that is made up immediately prior to use as follows:

10 mg diaminobenzidine (DAB) dissolved in 10 ml 50 mM sodium phosphate buffer, pH 7.4.

12.5 microliters 3% CoCl2/NiCl2 in deionized water 1.25 microliters hydrogen peroxide Slides are rinsed well three times for 10 min in deionized water and counterstained with 0.01% Light Green acidified with 0.01% acetic acid for 1-2 minutes depending on intensity of counterstain desired.

Slides are rinsed three times for 5 minutes with deionized water and dehydrated two times for 2 minutes in 95% ethanol; two times for 2 minutes in 100% ethanol; and two times for 2 minutes in xylene. Stained slides are mounted for visualization by microscopy.

9. IHC Staining of Frozen Tissue Sections

Fresh tissues are embedded carefully in OCT in plastic mold, without trapping air bubbles surrounding the tissue. Tissues are frozen by setting the mold on top of liquid nitrogen until 70-80% of the block turns white at which point the mold is placed on dry ice. The frozen blocks are stored at −80° C. Blocks are sectioned with a cryostat with care taken to avoid warming to greater than −10° C. Initially, the block is equilibrated in the cryostat for about 5 minutes and 6-10 mm sections are cut sequentially. Sections are allowed to dry for at least 30 minutes at room temperature. Following drying, tissues are stored at 4° C. for short term and −80° C. for longterm storage.

Sections are fixed by immersing in acetone jar for 1-2 minutes at room temperature, followed by drying at room temperature. Primary antibody is added (diluted in 0.05 M Tris-saline [0.05 M Tris, 0.15 M NaCl, pH 7.4], 2.5% serum) directly to the sections by covering the section dropwise to cover the tissue entirely. Binding is carried out by incubation a chamber for 1 hour at room temperature. Without letting the sections dry out, the secondary antibody (diluted in Tris-saline/2.5% serum) is added in a similar manner to the primary and incubated as before (at least 45 minutes). Following incubation, the sections are washed gently in Tris-saline for 3-5 minutes and then in Tris-saline/2.5% serum for another 3-5 minutes. If a biotinylated primary antibody is used, in place of the secondary antibody incubation, slides are covered with 100 ul of diluted alkaline phosphatase conjugated streptavidin, incubated for 30 minutes at room temperature and washed as above. Sections are incubated with alkaline phosphatse substrate (1 mg/ml Fast Violet; 0.2 mg/ml Napthol AS-MX phosphate in Tris-Saline pH 8.5) for 10-20 minutes until the desired positive staining is achieved at which point the reaction is stopped by washing twice with Tris-saline. Slides are counter-stained with Mayer's hematoxylin for 30 seconds and washed with tap water for 2-5 minutes. Sections are mounted with Mount coverslips and mounting media.

10. Assay for Antibody Dependent Cellular Cytotoxicity

Cultured tumor cells are labeled with 100 µCi $^{51}$Cr for 1 hour; Livingston, P. O., Zhang, S., Adluri, S., Yao, T.-J., Graeber, L., Ragupathi, G., Helling, F., & Fleischer, M. (1997). Cancer Immunol. Immunother. 43, 324-330. After being washed three times with culture medium, cells are resuspended at $10^5$/ml, and 100 µl/well are plated onto 96-well round-bottom plates. A range of antibody concentrations are applied to the wells, including an isotype control together with donor peripheral blood mononuclear cells that are plated at a 100:1 and 50:1 ratio. After an 18-h incubation at 37° C., supernatant (30 µl/well) is harvested and transferred onto Lumaplate 96 (Packard), dried, and read in a Packard Top-Count NXT γ counter. Each measurement is carried out in triplicate. Spontaneous release is determined by cpm of tumor cells incubated with medium and maximum release by cpm of tumor cells plus 1% Triton X-100 (Sigma). Specific lysis is defined as: % specific lysis= [(experimental release-spontaneous release)/(maximum release-spontaneous release)]×100. The percent ADCC is expressed as peak specific lysis postimmune subtracted by preimmune percent specific lysis. A doubling of the ADCC to >20% is considered significant.

11. Assay for Complement Dependent Cytotoxicity

Chromium release assays to assess complement-mediated cytotoxicity are performed for each patient at various time points; Dickler, M. N., Ragupathi, G., Liu, N. X., Musselli, C., Martino, D. J., Miller, V. A., Kris, M. G., Brezicka, F. T., Livingston, P. O. & Grant, S. C. (1999) Clin. Cancer Res. 5, 2773-2779. Cultured tumor cells are washed in FCS-free media two times, resuspended in 500 µl of media, and incubated with 100 µCi $^{51}$Cr per 10 million cells for 2 h at 37° C. The cells are then shaken every 15 min for 2 h, washed 3 times in media to achieve a concentration of approximately 20,000 cells/well, and then plated in round-bottom plates. The plates contain either 50 µl cells plus 50 µl monoclonal antibody, 50 µl cells plus serum (pre- and posttherapy), or 50 µl cells plus mouse serum as a control. The plates are incubated in a cold room on a shaker for 45 min. Human complement of a 1:5 dilution (resuspended in 1 ml of ice-cold water and diluted with 3% human serum albumin) is added to each well at a volume of 100 µl. Control wells include those for maximum release of isotope in 10% Triton X-100 (Sigma) and for spontaneous release in the absence of complement with medium alone. The plates are incubated for 2 h at 37° C., centrifuged for 3 min, and then 100 µl of supernatant is removed for radioactivity counting. The percentage of specific lysis is calculated as follows: % cytotoxicity=[(experimental release−spontaneous release)/ (maximum release−spontaneous release)]×100. A doubling of the CDC to >20% is considered significant.

12. In Vitro Assays in Cell Lines; RNAi

Lipofectamine is purchased from Invitrogen (Carlsbad, Calif.) and GeneSilencer from Gene Therapy Systems (San Diego, Calif.). Synthetic siRNA oligonucleotides are from Dharmacon (Lafayette, Colo.), Qiagen (Valencia, Calif.) or Ambion (Austin, Tex.) RNeasy 96 Kit is purchased from Qiagen (Valencia, Calif.). Apop-one homogeneous caspase-3/7 kit and CellTiter 96 AQueous One Solution Cell Proliferation Assay are both purchased from Promega (Madison, Wis.). Alamar Blue proliferation assay can be purchased from Biosource (Camarillo, Calif.). Function blocking antibodies are purchased from Chemicon (Temecula, Calif.), Biotrend (Cologne, Germany) or Alexis Corporation (San Diego, Calif.). Cell invasion assay kits from purchased from Chemicon (Temecula, Calif.). RiboGreen RNA Quantitation Kit is purchased from Molecular probes (Eugene, Oreg.).

RNAi

RNAi is performed by using Smartpools (Dharmacon), 4-for Silencing siRNA duplexes (Qiagen) or scrambled negative control siRNA (Ambion). Transient transfections are carried out in triplicate by using either Lipofectamine 2000 from Invitrogen (Carlsbad, Calif.) or by using GeneSilencer from Gene Therapy Systems (San Diego, Calif.) in methods described below. 1 to 4 days after transfections, total RNA is isolated by using the RNeasy 96 Kit (Qiagen) according to manufacturer's instructions and expression of mRNA is quantitated by using TaqMan technology. Protein expression levels are examined by flow cytometry and apoptosis and proliferation assays are performed daily using Apop-one homogeneous caspase-3/7 kit and CellTiter 96 AQueous One Solution Cell Proliferation Assay (see protocols below).

i) RNAi Transfections-Lipofectamine 2000

Transient transfections are carried out on sub-confluent pancreatic cancer cell lines as previously described. Elbashir, S. M. et al. (2001) Nature 411: 494-498; Caplen, N. J. et al. (2001) Proc Natl Acad Sci USA 98: 9742-9747; Sharp, P.A. (2001) Genes and Development 15: 485-490. Synthetic RNA to gene of interest or scrambled negative control siRNA is transfected using lipofectamine according to manufacturer's instructions. Cells are plated in 96 well plates in antibiotics free medium. The next day, the transfection reagent and siRNA are prepared for transfections as follows: Each 0.1-1 ul of lipofectamine 2000 and 10-150 mM siRNA are resuspended 25 ul serum-free media and incubated at room temperature for 5 minutes. After incubation, the diluted siRNA and the lipofectamine 2000 are combined and incubated for 20 minutes at room temperature. The cells are then washed and the combined siRNA-Lipofectamine 2000 reagent added. After further 4 hours incubation, 50 ul serum containing medium is added to each well. 1 and 4 days after transfection, expression of mRNA is quantitated by RT-PCR using TaqMan technology and protein expression levels are examined by flow cytometry. Apoptosis and proliferation assays are performed daily using Apop-one homogeneous caspase-3/7 kit and CellTiter 96 AQueous One Solution Cell Proliferation Assay (see protocols below).

ii) RNAi Transfections-GeneSilencer

Transient transfections are carried out on sub-confluent pancreatic cancer cell lines as previously described. Elbashir, S. M. et al. (2001) Nature 411: 494-498; Caplen, N. J. et al. (2001) Proc Natl Acad Sci USA 98: 9742-9747; Sharp, P.A. (2001) Genes and Development 15: 485-490. Synthetic RNA to gene of interest or scrambled negative control siRNA is transfected using Gene Silencer according to manufacturer's instructions. Cells are plated in 96 well plates in antibiotics free medium. The next day, the transfection reagent and the synthetic siRNA are prepared for transfections as follows: predetermined amount of Gene Silencer is diluted in serum-free media to a final volume of 20 ul per well. After resuspending 10-150 mM siRNA in 20 ul serum-free media, the reagents are combined and incubated at room temperature for 5-20 minutes. After incubation, the siRNA-Gene Silencer reagent is added to each well and incubated in a 37° C. incubator for 4 hours before an equal volume of serum containing media is added back to the cultured cells. The cells are then incubated for 1 to 4 days before mRNA, protein expression and effects on apoptosis and proliferation are examined.

Testing of Function Blocking Antibodies

Sub-confluent pancreatic cancer cell lines are serum-staved overnight. The next day, serum-containing media is added back to the cells in the presence of 5-50 ng/ml of function blocking antibodies. After 2 or 5 days incubation at 37° C. 5% $CO_2$, antibody binding is examined by flow cytometry and apoptosis and proliferation are examined by using protocols described below.

Apoptosis

Apoptosis assay is performed by using the Apop-one homogeneous caspase-3/7 kit from Promega. Briefly, the caspase-3/7 substrate is thawed to room temperature and diluted 1:100 with buffer. The diluted substrate is then added 1:1 to cells, control or blank. The plates are then placed on a plate shaker for 30 minutes to 18 hours at 300-500 rpm. The fluorescence of each well is then measured at using an excitation wavelength of 485+/−20 nm and an emission wavelength of 530+/−25 nm.

Proliferation—MTS

Proliferation assay is performed by using the CellTiter 96 AQueous One Solution Cell Proliferation Assay kit from Promega. 20 ul of CellTiter 96 AQueous One Solution is added to 100 ul of culture medium. The plates are then incubated for 1-4 hours at 37° C. in a humidified 5% $CO_2$ incubator. After incubation, the change in absorbance is read at 490 nm.

Proliferation-Alamar Blue

Proliferation assay is performed by using the Alamar Blue assay from Biosource. 10 ul of Alamar Blue reagent is added to 100 ul of cells in culture medium. The plates are then incubated for 1-4 hours at 37° C. in a humidified 5% $CO_2$ incubator. After incubation, the change in fluorescence is measured at using an excitation wavelength of 530 nm and an emission wavelength of 595 nm.

Cell Invasion

Cell invasion assay is performed by using the 96 well cell invasion assay kit available from Chemicon. After the cell invasion chamber plates are adjusted to room temperature, 100 ul serum-free media is added to the interior of the inserts. 1-2 hours later, cell suspensions of $1 \times 10^6$ cells/ml are prepared. Media is then carefully removed from the inserts and 100 ul of prepared cells are added into the insert +/−0 to 50 ng function blocking antibodies. The cells are pre-incubated for 15 minutes at 37° C. before 150 ul of media containing 10% FBS is added to the lower chamber. The cells are then incubated for 48 hours at 37° C. After incubation, the cells from the top side of the insert are discarded and the invasion chamber plates are then placed on a new 96-well feeder tray containing 150 ul of pre-warmed cell detachment solution in the wells. The plates are incubated for 30 minutes at 37° C. and are periodically shaken. Lysis buffer/dye solution (4 ul CyQuant Dye/300 ul 4× lysis buffer) is prepared and added to each well of dissociation buffer/cells on feeder tray. The plates are incubated for 15 minutes at room temperature before 150 ul is transferred to a new 96-well plate. Fluorescence of invading cells is then read at 480 excitation and 520 emission.

Receptor Internalization

For quantification of receptor internalization, ELISA assays are performed essentially as described by Daunt et al.

Daunt, D. A., Hurtz, C., Hein, L., Kallio, J., Feng, F., and Kobilka, B. K. (1997) Mol. Pharmacol. 51, 711-720. The cell lines are plated at $6 \times 10^5$ cells per in a 24-well tissue culture dishes that have previously been coated with 0.1 mg/ml poly-L-lysine. The next day, the cells are washed once with PBS and incubated in DMEM at 37° C. for several minutes. Agonist to the secreted target of interest is then added at a pre-determined concentration in prewarmed DMEM to the wells. The cells are then incubated for various times at 37° C. and reactions are stopped by removing the media and fixing the cells in 3.7% formaldehyde/TBS for 5 min at room temperature. The cells are then washed three times with TBS and nonspecific binding blocked with TBS containing 1% BSA for 45 min at room temperature. The first antibody is added at a pre-determined dilution in TBS/BSA for 1 h at room temperature. Three washes with TBS followed, and cells are briefly reblocked for 15 min at room temperature. Incubation with goat anti-mouse conjugated alkaline phosphatase (Bio-Rad) diluted 1:1000 in TBS/BSA is carried out for 1 h at room temperature. The cells are washed three times with TBS and a colorimetric alkaline phosphatase substrate is added. When the adequate color change is reached, 100-μl samples are taken for colorimetric readings.

mRNA Expression

Expression of mRNA is quantitated by RT-PCR using TaqMan® technology. Total RNA is isolated from cancer model cell lines using the RNEasy 96 kit (Qiagen) per manufacturer's instructions and included DNase treatment. Target transcript sequences are identified for the differentially expressed peptides by searching the BlastP database. TaqMan assays (PCR primer/probe set) specific for those transcripts are identified by searching the Celera Discovery System™ (CDS) database. The assays are designed to span exon-exon borders and do not amplify genomic DNA. The TaqMan primers and probe sequences are as designed by Applied Biosystems (AB) as part of the Assays on Demand™ product line or by custom design through the AB Assays by Design℠ service. RT-PCR is accomplished using AmpliTaqGold and MultiScribe reverse transcriptase in the One Step RT-PCR Master Mix reagent kit (AB) according to the manufacturers instructions. Probe and primer concentrations are 900 nM and 250 nM, respectively, in a 25 μl reaction. For each experiment, a master mix of the above components is made and aliquoted into each optical reaction well. 5 ul of total RNA is the template. Each sample is assayed in triplicate. Quantitative RT-PCR is performed using the ABI Prism® 7900HT Sequence Detection System (SDS). Cycling parameters follow: 48° for 30 min. for one cycle; 95° C. for 10 min for one cycle; 95° C. for 15 sec, 60° C. for 1 min. for 40 cycles.

The SDS software calculates the threshold cycle ($C_T$) for each reaction, and $C_T$ values are used to quantitate the relative amount of starting template in the reaction. The $C_T$ values for each set of three reactions are averaged for all subsequent calculations.

Total RNA is quantitated by using RiboGreen RNA Quantitation Kit according to manufacturer's instructions and the % mRNA expression is calculated using total RNA for normalization. % knockdown is then calculated relative to the no addition control.

13. In Vivo Studies by Using Antibodies

Treatment of Pancreatic Cancer Cells with Monoclonal Antibodies.

Pancreatic cancer cells are seeded at a density of $4 \times 10^4$ cells per well in 96-well microtiter plates and allowed to adhere for 2 hours. The cells are then treated with different concentrations of anti-PCAST monoclonal antibody (Mab) or irrelevant isotype matched (anti-rHuIFN-. gamma. Mab) at 0.05, 0.5 or 5.0 mug/ml. After a 72 hour incubation, the cell monolayers are stained with crystal violet dye for determination of relative percent viability (RPV) compared to control (untreated) cells. Each treatment group consists of replicates. Cell growth inhibition is monitored.

Treatment of NIH 3T3 Cells Overexpression PCAST Protein with Monoclonal Antibodies.

NIH 3T3 expressing PCAST protein are treated with different concentrations of anti-PCAST MAbs. Cell growth inhibition is monitored.

In Vivo Treatment of NIH 3T3 Cells Overexpressing PCAST with anti-PCAST Monoclonal Antibodies.

NIH 3T3 cells transfected with either a PCAST expression plasmid or the neo-DHFR vector are injected into nu/nu (athymic) mice subcutaneously at a dose of $10^6$ cells in 0.1 ml of phosphate-buffered saline. On days 0, 1, 5 and every 4 days thereafter, 100 mug (0.1 ml in PBS) of either an irrelevant or anti-PCAST monoclonal antibody of the IG2A subclass is injected intraperitoneally. Tumor occurrence and size are monitored for 1 month period of treatment.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

The invention claimed is:

1. A method of assessing pancreatic cancer in an individual, the method comprising detecting a KLK11 protein, set forth as an amino acid sequence comprising SEQ ID NO:10, in a sample from the individual, wherein the presence of the KLK11 protein is indicative of pancreatic cancer.

2. The method of claim 1, wherein the assessing comprises diagnosing pancreatic cancer.

3. The method of claim 1, wherein the assessing comprises determining an individual's risk of developing pancreatic cancer in the future.

4. The method of claim 1, wherein the assessing comprises prognosing the future course of pancreatic cancer in an individual who has pancreatic cancer.

5. The method of claim 1, wherein the detecting comprises determining the abundance level of the KLK11 protein.

6. The method of claim 5, wherein the method further comprises comparing the abundance level of the KLK11 protein to a reference level.

7. The method of claim 6, wherein the reference level is representative of the normal abundance level of KLK11 protein in an individual who does not have pancreatic cancer.

8. The method of claim 6, wherein a difference between the abundance level of the KLK11 protein and the reference level is indicative of pancreatic cancer.

9. The method of claim 7, wherein a difference between the abundance level of the KLK11 protein and the reference level is indicative of pancreatic cancer.

10. The method of claim 1, wherein the amino acid sequence of the KLK11 protein consists of SEQ ID NO:10.

11. The method of claim 1, wherein the KLK11 protein is detected by contacting the sample with an isolated antibody that selectively binds to the KLK11 protein and determining the extent of binding of the antibody to the KLK11 protein.

12. The method of claim 11, wherein the antibody is coupled to a detectable substance.

13. The method of claim 5, wherein the KLK11 protein is detected by contacting the sample with an isolated antibody that selectively binds to the KLK11 protein and determining the extent of binding of the antibody to the KLK11 protein.

14. The method of claim 13, wherein the antibody is coupled to a detectable substance.

15. The method of claim 1, wherein the detecting comprises determining the activity of the KLK11 protein.

* * * * *

SEQUENCE LISTING

```
<160> NUMBER OF SEQ ID NOS: 51

<210> SEQ ID NO 1
<211> LENGTH: 21
<212> TYPE: PRT
<213> ORGANISM: Homo sapiens

<400> SEQUENCE: 1
```

Tyr Leu Cys Ala Ser Arg Pro Asp Gly Ser Gly Asn Thr Ile Tyr
1               5                   10                  15

Phe Gly Glu Gly Ser
            20

<210> SEQ ID NO 2
<211> LENGTH: 346
<212> TYPE: PRT
<213> ORGANISM: Homo sapiens

<400> SEQUENCE: 2

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn

<210> SEQ ID NO 3
<211> LENGTH: 346
<212> TYPE: PRT
<213> ORGANISM: Homo sapiens

<400> SEQUENCE: 3

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 4
<211> LENGTH: 359

```
<212> TYPE: PRT
<213> ORGANISM: Homo sapiens

<400> SEQUENCE: 4

Met Ser Pro Arg Met Glu Cys Ser Asp Thr Phe Ser Lys Met Ala Met
1               5                   10                  15

Val Ser Glu Phe Leu Lys Gln Ala Trp Phe Ile Glu Asn Glu Glu Gln
            20                  25                  30

Glu Tyr Val Gln Thr Val Lys Ser Lys Gly Gly Pro Gly Ser Ala
        35                  40                  45

Val Ser Pro Tyr Pro Thr Phe Asn Pro Ser Ser Asp Val Ala Ala Leu
    50                  55                  60

His Lys Ala Ile Met Val Lys Gly Val Asp Glu Ala Thr Ile Ile Asp
65                  70                  75                  80

Ile Leu Thr Lys Arg Asn Asn Ala Gln Arg Gln Gln Ile Lys Ala Ala
                85                  90                  95

Tyr Leu Gln Glu Thr Gly Lys Pro Leu Asp Glu Thr Leu Lys Lys Ala
                100                 105                 110

Leu Thr Gly His Leu Glu Glu Val Val Leu Ala Leu Leu Lys Thr Pro
            115                 120                 125

Ala Gln Phe Asp Ala Asp Glu Leu Arg Ala Ala Met Lys Gly Leu Gly
        130                 135                 140

Thr Asp Glu Asp Thr Leu Ile Glu Ile Leu Ala Ser Arg Thr Asn Lys
145                 150                 155                 160

Glu Ile Arg Asp Ile Asn Arg Val Tyr Arg Glu Glu Leu Lys Arg Asp
                165                 170                 175

Leu Ala Lys Asp Ile Thr Ser Asp Thr Ser Gly Asp Phe Arg Asn Ala
                180                 185                 190

Leu Leu Ser Leu Ala Lys Gly Asp Arg Ser Glu Asp Phe Gly Val Asn
            195                 200                 205

Glu Asp Leu Ala Asp Ser Asp Ala Arg Ala Leu Tyr Glu Ala Gly Glu
            210                 215                 220

Arg Arg Lys Gly Thr Asp Val Asn Val Phe Asn Thr Ile Leu Thr Thr
225                 230                 235                 240

Arg Ser Tyr Pro Gln Leu Arg Arg Val Phe Gln Lys Tyr Thr Lys Tyr
                245                 250                 255

Ser Lys His Asp Met Asn Lys Val Leu Asp Leu Glu Leu Lys Gly Asp
                260                 265                 270

Ile Glu Lys Cys Leu Thr Ala Ile Val Lys Cys Ala Thr Ser Lys Pro
            275                 280                 285

Ala Phe Phe Ala Glu Lys Leu His Gln Ala Met Lys Gly Val Gly Thr
        290                 295                 300

Arg His Lys Ala Leu Ile Arg Ile Met Val Ser Arg Ser Glu Ile Asp
305                 310                 315                 320

Met Asn Asp Ile Lys Ala Phe Tyr Gln Lys Met Tyr Gly Ile Ser Leu
                325                 330                 335

Cys Gln Ala Ile Leu Asp Glu Thr Lys Gly Asp Tyr Glu Lys Ile Leu
            340                 345                 350

Val Ala Leu Cys Gly Gly Asn
            355

<210> SEQ ID NO 5
<211> LENGTH: 346
<212> TYPE: PRT
<213> ORGANISM: Homo sapiens
```

<400> SEQUENCE: 5

| Met | Ala | Met | Val | Ser | Glu | Phe | Leu | Lys | Gln | Ala | Trp | Phe | Ile | Glu | Asn |
| 1 | | | | 5 | | | | | 10 | | | | | 15 | |

| Glu | Glu | Gln | Glu | Tyr | Val | Gln | Thr | Val | Lys | Ser | Ser | Lys | Gly | Gly | Pro |
| | | | 20 | | | | | 25 | | | | | 30 | | |

| Gly | Ser | Ala | Val | Ser | Pro | Tyr | Pro | Thr | Phe | Asn | Pro | Ser | Ser | Asp | Val |
| | | 35 | | | | | 40 | | | | | 45 | | | |

| Ala | Ala | Leu | His | Lys | Ala | Ile | Met | Val | Lys | Gly | Val | Asp | Glu | Ala | Thr |
| | 50 | | | | | 55 | | | | | 60 | | | | |

| Ile | Ile | Asp | Ile | Leu | Thr | Lys | Arg | Asn | Asn | Ala | Gln | Arg | Gln | Gln | Ile |
| 65 | | | | | 70 | | | | | 75 | | | | | 80 |

| Lys | Ala | Ala | Tyr | Leu | Gln | Glu | Thr | Gly | Lys | Pro | Leu | Asp | Glu | Thr | Leu |
| | | | | 85 | | | | | 90 | | | | | 95 | |

| Lys | Lys | Ala | Leu | Thr | Gly | His | Leu | Glu | Glu | Val | Val | Leu | Ala | Leu | Leu |
| | | | 100 | | | | | 105 | | | | | 110 | | |

| Lys | Thr | Pro | Ala | Gln | Phe | Asp | Ala | Asp | Glu | Leu | Arg | Ala | Ala | Met | Lys |
| | | 115 | | | | | 120 | | | | | 125 | | | |

| Gly | Leu | Gly | Thr | Asp | Glu | Asp | Thr | Leu | Ile | Glu | Ile | Leu | Ala | Ser | Arg |
| | 130 | | | | | 135 | | | | | 140 | | | | |

| Thr | Asn | Lys | Glu | Ile | Arg | Asp | Ile | Asn | Arg | Val | Tyr | Arg | Glu | Glu | Leu |
| 145 | | | | | 150 | | | | | 155 | | | | | 160 |

| Lys | Arg | Asp | Leu | Ala | Lys | Asp | Ile | Thr | Ser | Asp | Thr | Ser | Gly | Asp | Phe |
| | | | | 165 | | | | | 170 | | | | | 175 | |

| Arg | Asn | Ala | Leu | Leu | Ser | Leu | Ala | Lys | Gly | Asp | Arg | Ser | Glu | Asp | Phe |
| | | | 180 | | | | | 185 | | | | | 190 | | |

| Gly | Val | Asn | Glu | Asp | Leu | Ala | Asp | Ser | Asp | Ala | Arg | Ala | Leu | Tyr | Glu |
| | | 195 | | | | | 200 | | | | | 205 | | | |

| Ala | Gly | Glu | Arg | Arg | Lys | Gly | Thr | Asp | Val | Asn | Val | Phe | Asn | Thr | Ile |
| | 210 | | | | | 215 | | | | | 220 | | | | |

| Leu | Thr | Thr | Arg | Ser | Tyr | Pro | Gln | Leu | Arg | Arg | Val | Phe | Gln | Lys | Tyr |
| 225 | | | | | 230 | | | | | 235 | | | | | 240 |

| Thr | Lys | Tyr | Ser | Lys | His | Asp | Met | Asn | Lys | Val | Leu | Asp | Leu | Glu | Leu |
| | | | | 245 | | | | | 250 | | | | | 255 | |

| Lys | Gly | Asp | Ile | Glu | Lys | Cys | Leu | Thr | Ala | Ile | Val | Lys | Cys | Ala | Thr |
| | | | 260 | | | | | 265 | | | | | 270 | | |

| Ser | Lys | Pro | Ala | Phe | Phe | Ala | Glu | Lys | Leu | His | Gln | Ala | Met | Lys | Gly |
| | | 275 | | | | | 280 | | | | | 285 | | | |

| Val | Gly | Thr | Arg | His | Lys | Ala | Leu | Ile | Arg | Ile | Met | Val | Ser | Arg | Ser |
| | 290 | | | | | 295 | | | | | 300 | | | | |

| Glu | Ile | Asp | Met | Asn | Asp | Ile | Lys | Ala | Phe | Tyr | Gln | Lys | Met | Tyr | Gly |
| 305 | | | | | 310 | | | | | 315 | | | | | 320 |

| Ile | Ser | Leu | Cys | Gln | Ala | Ile | Leu | Asp | Glu | Thr | Lys | Gly | Asp | Tyr | Glu |
| | | | | 325 | | | | | 330 | | | | | 335 | |

| Lys | Ile | Leu | Val | Ala | Leu | Cys | Gly | Gly | Asn |
| | | | 340 | | | | | 345 | |

<210> SEQ ID NO 6
<211> LENGTH: 346
<212> TYPE: PRT
<213> ORGANISM: Homo sapiens

<400> SEQUENCE: 6

| Met | Ala | Met | Val | Ser | Glu | Phe | Leu | Lys | Gln | Ala | Trp | Phe | Ile | Glu | Asn |
| 1 | | | | 5 | | | | | 10 | | | | | 15 | |

```
Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
            50                  55                  60

Ile Ile Asp Ile Leu Thr Lys Arg Asn Asn Ala Gln Arg Gln Gln Ile
 65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
            115                 120                 125

Gly Leu Gly Thr Asp Glu Asp Thr Leu Ile Glu Ile Leu Ala Ser Arg
            130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
            195                 200                 205

Ala Gly Glu Arg Arg Lys Gly Thr Asp Val Asn Val Phe Asn Thr Ile
            210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
            275                 280                 285

Val Gly Thr Arg His Lys Ala Leu Ile Arg Ile Met Val Ser Arg Ser
            290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 7
<211> LENGTH: 357
<212> TYPE: PRT
<213> ORGANISM: Homo sapiens

<400> SEQUENCE: 7

Met Asn Leu Ile Leu Arg Tyr Thr Phe Ser Lys Met Ala Met Val Ser
 1               5                  10                  15

Glu Phe Leu Lys Gln Ala Trp Phe Ile Glu Asn Glu Glu Gln Glu Tyr
            20                  25                  30

Val Gln Thr Val Lys Ser Ser Lys Gly Gly Pro Gly Ser Ala Val Ser
```

-continued

```
                35                  40                  45
Pro Tyr Pro Thr Phe Asn Pro Ser Ser Asp Val Ala Ala Leu His Lys
 50                  55                  60

Ala Ile Met Val Lys Gly Val Asp Glu Ala Thr Ile Ile Asp Ile Leu
 65                  70                  75                  80

Thr Lys Arg Asn Asn Ala Gln Arg Gln Gln Ile Lys Ala Ala Tyr Leu
                 85                  90                  95

Gln Glu Thr Gly Lys Pro Leu Asp Glu Thr Leu Lys Lys Ala Leu Thr
                100                 105                 110

Gly His Leu Glu Glu Val Val Leu Ala Leu Leu Lys Thr Pro Ala Gln
                115                 120                 125

Phe Asp Ala Asp Glu Leu Arg Ala Ala Met Lys Gly Leu Gly Thr Asp
130                 135                 140

Glu Asp Thr Leu Ile Glu Ile Leu Ala Ser Arg Thr Asn Lys Glu Ile
145                 150                 155                 160

Arg Asp Ile Asn Arg Val Tyr Arg Glu Glu Leu Lys Arg Asp Leu Ala
                165                 170                 175

Lys Asp Ile Thr Ser Asp Thr Ser Gly Asp Phe Arg Asn Ala Leu Leu
                180                 185                 190

Ser Leu Ala Lys Gly Asp Arg Ser Glu Asp Phe Gly Val Asn Glu Asp
                195                 200                 205

Leu Ala Asp Ser Asp Ala Arg Ala Leu Tyr Glu Ala Gly Glu Arg Arg
210                 215                 220

Lys Gly Thr Asp Val Asn Val Phe Asn Thr Ile Leu Thr Thr Arg Ser
225                 230                 235                 240

Tyr Pro Gln Leu Arg Arg Val Phe Gln Lys Tyr Thr Lys Tyr Ser Lys
                245                 250                 255

His Asp Met Asn Lys Val Leu Asp Leu Glu Leu Lys Gly Asp Ile Glu
                260                 265                 270

Lys Cys Leu Thr Ala Ile Val Lys Cys Ala Thr Ser Lys Pro Ala Phe
                275                 280                 285

Phe Ala Glu Lys Leu His Gln Ala Met Lys Gly Val Gly Thr Arg His
290                 295                 300

Lys Ala Leu Ile Arg Ile Met Val Ser Arg Ser Glu Ile Asp Met Asn
305                 310                 315                 320

Asp Ile Lys Ala Phe Tyr Gln Lys Met Tyr Gly Ile Ser Leu Cys Gln
                325                 330                 335

Ala Ile Leu Asp Glu Thr Lys Gly Asp Tyr Glu Lys Ile Leu Val Ala
                340                 345                 350

Leu Cys Gly Gly Asn
        355

<210> SEQ ID NO 8
<211> LENGTH: 345
<212> TYPE: PRT
<213> ORGANISM: Homo sapiens

<400> SEQUENCE: 8

Ala Met Val Ser Glu Phe Leu Lys Gln Ala Trp Phe Ile Glu Asn Glu
 1               5                  10                  15

Glu Gln Glu Tyr Val Gln Thr Val Lys Ser Ser Lys Gly Gly Pro Gly
                20                  25                  30

Ser Ala Val Ser Pro Tyr Pro Thr Phe Asn Pro Ser Ser Asp Val Ala
                35                  40                  45
```

Ala Leu His Lys Ala Ile Met Val Lys Gly Val Asp Glu Ala Thr Ile
 50                  55                  60

Ile Asp Ile Leu Thr Lys Arg Asn Asn Ala Gln Arg Gln Gln Ile Lys
 65                  70                  75                  80

Ala Ala Tyr Leu Gln Glu Thr Gly Lys Pro Leu Asp Glu Thr Leu Lys
                 85                  90                  95

Lys Ala Leu Thr Gly His Leu Glu Glu Val Val Leu Ala Leu Leu Lys
            100                 105                 110

Thr Pro Ala Gln Phe Asp Ala Asp Glu Leu Arg Ala Ala Met Lys Gly
        115                 120                 125

Leu Gly Thr Asp Glu Asp Thr Leu Ile Glu Ile Leu Ala Ser Arg Thr
130                 135                 140

Asn Lys Glu Ile Arg Asp Ile Asn Arg Val Tyr Arg Glu Glu Leu Lys
145                 150                 155                 160

Arg Asp Leu Ala Lys Asp Ile Thr Ser Asp Thr Ser Gly Asp Phe Arg
                165                 170                 175

Asn Ala Leu Leu Ser Leu Ala Lys Gly Asp Arg Ser Glu Asp Phe Gly
            180                 185                 190

Val Asn Glu Asp Leu Ala Asp Ser Asp Ala Arg Ala Leu Tyr Glu Ala
        195                 200                 205

Gly Glu Arg Arg Lys Gly Thr Asp Val Asn Val Phe Asn Thr Ile Leu
210                 215                 220

Thr Thr Arg Ser Tyr Pro Gln Leu Arg Arg Val Phe Gln Lys Tyr Thr
225                 230                 235                 240

Lys Tyr Ser Lys His Asp Met Asn Lys Val Leu Asp Leu Glu Leu Lys
                245                 250                 255

Gly Asp Ile Glu Lys Cys Leu Thr Ala Ile Val Lys Cys Ala Thr Ser
            260                 265                 270

Lys Pro Ala Phe Phe Ala Glu Lys Leu His Gln Ala Met Lys Gly Val
        275                 280                 285

Gly Thr Arg His Lys Ala Leu Ile Arg Ile Met Val Ser Arg Ser Glu
290                 295                 300

Ile Asp Met Asn Asp Ile Lys Ala Phe Tyr Gln Lys Met Tyr Gly Ile
305                 310                 315                 320

Ser Leu Cys Gln Ala Ile Leu Asp Glu Thr Lys Gly Asp Tyr Glu Lys
                325                 330                 335

Ile Leu Val Ala Leu Cys Gly Gly Asn
            340                 345

<210> SEQ ID NO 9
<211> LENGTH: 593
<212> TYPE: PRT
<213> ORGANISM: Homo sapiens

<400> SEQUENCE: 9

Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
                20                  25                  30

Asp Pro Gly Gly Ala Ser Tyr Ser Cys Cys Arg Pro Leu Leu Asp Lys
            35                  40                  45

Trp Pro Thr Thr Leu Ser Arg His Leu Gly Gly Pro Cys Gln Val Asp
        50                  55                  60

Ala His Cys Ser Ala Gly His Ser Cys Ile Phe Thr Val Ser Gly Thr
65                  70                  75                  80

-continued

```
Ser Ser Cys Cys Pro Phe Pro Glu Ala Val Ala Cys Gly Asp Gly His
                 85                  90                  95

His Cys Cys Pro Arg Gly Phe His Cys Ser Ala Asp Gly Arg Ser Cys
                100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
            245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
            325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
            405                 410                 415

Gln Arg Gly Ser Glu Ile Val Ala Gly Leu Glu Lys Met Pro Ala Arg
        420                 425                 430

Arg Ala Ser Leu Ser His Pro Arg Asp Ile Gly Cys Asp Gln His Thr
    435                 440                 445

Ser Cys Pro Val Gly Gly Thr Cys Cys Pro Ser Leu Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
            485                 490                 495
```

```
Lys Glu Val Val Ser Ala Gln Pro Ala Thr Phe Leu Ala Arg Ser Pro
                500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
        530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu

<210> SEQ ID NO 10
<211> LENGTH: 250
<212> TYPE: PRT
<213> ORGANISM: Homo sapiens

<400> SEQUENCE: 10

Met Arg Ile Leu Gln Leu Ile Leu Leu Ala Leu Ala Thr Gly Leu Val
1               5                   10                  15

Gly Gly Glu Thr Arg Ile Ile Lys Gly Phe Glu Cys Lys Pro His Ser
            20                  25                  30

Gln Pro Trp Gln Ala Ala Leu Phe Glu Lys Thr Arg Leu Leu Cys Gly
        35                  40                  45

Ala Thr Leu Ile Ala Pro Arg Trp Leu Leu Thr Ala Ala His Cys Leu
50                  55                  60

Lys Pro Arg Tyr Ile Val His Leu Gly Gln His Asn Leu Gln Lys Glu
65                  70                  75                  80

Glu Gly Cys Glu Gln Thr Arg Thr Ala Thr Glu Ser Phe Pro His Pro
                85                  90                  95

Gly Phe Asn Asn Ser Leu Pro Asn Lys Asp His Arg Asn Asp Ile Met
            100                 105                 110

Leu Val Lys Met Ala Ser Pro Val Ser Ile Thr Trp Ala Val Arg Pro
        115                 120                 125

Leu Thr Leu Ser Ser Arg Cys Val Thr Ala Gly Thr Ser Cys Leu Ile
130                 135                 140

Ser Gly Trp Gly Ser Thr Ser Ser Pro Gln Leu Arg Leu Pro His Thr
145                 150                 155                 160

Leu Arg Cys Ala Asn Ile Thr Ile Ile Glu His Gln Lys Cys Glu Asn
                165                 170                 175

Ala Tyr Pro Gly Asn Ile Thr Asp Thr Met Val Cys Ala Ser Val Gln
            180                 185                 190

Glu Gly Gly Lys Asp Ser Cys Gln Gly Asp Ser Gly Gly Pro Leu Val
        195                 200                 205

Cys Asn Gln Ser Leu Gln Gly Ile Ile Ser Trp Gly Gln Asp Pro Cys
210                 215                 220

Ala Ile Thr Arg Lys Pro Gly Val Tyr Thr Lys Val Cys Lys Tyr Val
225                 230                 235                 240

Asp Trp Ile Gln Glu Thr Met Lys Asn Asn
                245                 250

<210> SEQ ID NO 11
<211> LENGTH: 381
```

```
<212> TYPE: PRT
<213> ORGANISM: Homo sapiens

<400> SEQUENCE: 11

Met Ser Ser Arg Ile Ala Arg Ala Leu Ala Leu Val Val Thr Leu Leu
 1               5                  10                  15

His Leu Thr Arg Leu Ala Leu Ser Thr Cys Pro Ala Ala Cys His Cys
             20                  25                  30

Pro Leu Glu Ala Pro Lys Cys Ala Pro Gly Val Gly Leu Val Arg Asp
         35                  40                  45

Gly Cys Gly Cys Cys Lys Val Cys Ala Lys Gln Leu Asn Glu Asp Cys
 50                  55                  60

Ser Lys Thr Gln Pro Cys Asp His Thr Lys Gly Leu Glu Cys Asn Phe
 65                  70                  75                  80

Gly Ala Ser Ser Thr Ala Leu Lys Gly Ile Cys Arg Ala Gln Ser Glu
                 85                  90                  95

Gly Arg Pro Cys Glu Tyr Asn Ser Arg Ile Tyr Gln Asn Gly Glu Ser
            100                 105                 110

Phe Gln Pro Asn Cys Lys His Gln Cys Thr Cys Ile Asp Gly Ala Val
        115                 120                 125

Gly Cys Ile Pro Leu Cys Pro Gln Glu Leu Ser Leu Pro Asn Leu Gly
    130                 135                 140

Cys Pro Asn Pro Arg Leu Val Lys Val Thr Gly Gln Cys Cys Glu Glu
145                 150                 155                 160

Trp Val Cys Asp Glu Asp Ser Ile Lys Asp Pro Met Glu Asp Gln Asp
                165                 170                 175

Gly Leu Leu Gly Lys Glu Leu Gly Phe Asp Ala Ser Glu Val Glu Leu
            180                 185                 190

Thr Arg Asn Asn Glu Leu Ile Ala Val Gly Lys Gly Ser Ser Leu Lys
        195                 200                 205

Arg Leu Pro Val Phe Gly Met Glu Pro Arg Ile Leu Tyr Asn Pro Leu
    210                 215                 220

Gln Gly Gln Lys Cys Ile Val Gln Thr Thr Ser Trp Ser Gln Cys Ser
225                 230                 235                 240

Lys Thr Cys Gly Thr Gly Ile Ser Thr Arg Val Thr Asn Asp Asn Pro
                245                 250                 255

Glu Cys Arg Leu Val Lys Glu Thr Arg Ile Cys Glu Val Arg Pro Cys
            260                 265                 270

Gly Gln Pro Val Tyr Ser Ser Leu Lys Lys Gly Lys Lys Cys Ser Lys
        275                 280                 285

Thr Lys Lys Ser Pro Glu Pro Val Arg Phe Thr Tyr Ala Gly Cys Leu
    290                 295                 300

Ser Val Lys Lys Tyr Arg Pro Lys Tyr Cys Gly Ser Cys Val Asp Gly
305                 310                 315                 320

Arg Cys Cys Thr Pro Gln Leu Thr Arg Thr Val Lys Met Arg Phe Arg
                325                 330                 335

Cys Glu Asp Gly Glu Thr Phe Ser Lys Asn Val Met Met Ile Gln Ser
            340                 345                 350

Cys Lys Cys Asn Tyr Asn Cys Pro His Ala Asn Glu Ala Ala Phe Pro
        355                 360                 365

Phe Tyr Arg Leu Phe Asn Asp Ile His Lys Phe Arg Asp
    370                 375                 380

<210> SEQ ID NO 12
```

<211> LENGTH: 258
<212> TYPE: PRT
<213> ORGANISM: Homo sapiens

<400> SEQUENCE: 12

```
Met Leu Pro Leu Cys Leu Val Ala Ala Leu Leu Ala Ala Gly Pro
1               5                   10                  15

Gly Pro Ser Leu Gly Asp Glu Ala Ile His Cys Pro Pro Cys Ser Glu
            20                  25                  30

Glu Lys Leu Ala Arg Cys Arg Pro Val Gly Cys Glu Glu Leu Val
        35                  40                  45

Arg Glu Pro Gly Cys Gly Cys Cys Ala Thr Cys Ala Leu Gly Leu Gly
    50                  55                  60

Met Pro Cys Gly Val Tyr Thr Pro Arg Cys Gly Ser Gly Leu Arg Cys
65                  70                  75                  80

Tyr Pro Pro Arg Gly Val Glu Lys Pro Leu His Thr Leu Met His Gly
                85                  90                  95

Gln Gly Val Cys Met Glu Leu Ala Glu Ile Glu Ala Ile Gln Glu Ser
            100                 105                 110

Leu Gln Pro Ser Asp Lys Asp Glu Gly Asp His Pro Asn Asn Ser Phe
        115                 120                 125

Ser Pro Cys Ser Ala His Asp Arg Arg Cys Leu Gln Lys His Phe Ala
130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
    210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe
                245                 250                 255

Arg Glu
```

<210> SEQ ID NO 13
<211> LENGTH: 258
<212> TYPE: PRT
<213> ORGANISM: Homo sapiens

<400> SEQUENCE: 13

```
Met Leu Pro Leu Cys Leu Val Ala Ala Leu Leu Ala Ala Gly Pro
1               5                   10                  15

Gly Pro Ser Leu Gly Asp Glu Ala Ile His Cys Pro Pro Cys Ser Glu
            20                  25                  30

Glu Lys Leu Ala Arg Cys Arg Pro Val Gly Cys Glu Glu Leu Val
        35                  40                  45

Arg Glu Ala Gly Cys Gly Cys Cys Ala Thr Cys Ala Leu Gly Leu Gly
    50                  55                  60

Met Pro Cys Gly Val Tyr Thr Pro Arg Cys Gly Ser Gly Leu Arg Cys
65                  70                  75                  80
```

```
Tyr Pro Pro Arg Gly Val Glu Lys Pro Leu His Thr Leu Met His Gly
            85                  90                  95

Gln Gly Val Cys Met Glu Leu Ala Glu Ile Glu Ala Ile Gln Glu Ser
            100                 105                 110

Leu Gln Pro Ser Asp Lys Asp Glu Gly Asp His Pro Asn Asn Ser Phe
            115                 120                 125

Ser Pro Cys Ser Ala His Asp Arg Arg Cys Leu Gln Lys His Phe Ala
            130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
            165                 170                 175

Glu Leu His Arg Ala Leu Glu Arg Leu Ala Ala Ser Gln Ser Arg Thr
            180                 185                 190

His Glu Asp Leu Tyr Phe Ile Pro Ile Pro Asn Cys Asp Arg Asn Gly
            195                 200                 205

Asn Phe His Pro Lys Gln Cys His Pro Ala Leu Asp Gly Gln Arg Gly
            210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe
            245                 250                 255

Arg Glu

<210> SEQ ID NO 14
<211> LENGTH: 1390
<212> TYPE: PRT
<213> ORGANISM: Homo sapiens

<400> SEQUENCE: 14

Met Lys Ala Pro Ala Val Leu Ala Pro Gly Ile Leu Val Leu Leu Phe
 1               5                  10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
            50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
            85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
            130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
            165                 170                 175

Val Ser Ala Leu Gly Ala Lys Val Leu Ser Ser Val Lys Asp Arg Phe
            180                 185                 190
```

-continued

```
Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
```

-continued

```
            610                 615                 620
Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
                850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                915                 920                 925

Gln Asn Phe Thr Gly Leu Ile Ala Gly Val Val Ser Ile Ser Thr Ala
                930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser Val Asp Tyr Arg Ala Thr Phe Pro
                995                 1000                1005

Glu Asp Gln Phe Pro Asn Ser Ser Gln Asn Gly Ser Cys Arg Gln Val
                1010                1015                1020

Gln Tyr Pro Leu Thr Asp Met Ser Pro Ile Leu Thr Ser Gly Asp Ser
1025                1030                1035                1040
```

Asp Ile Ser Ser Pro Leu Leu Gln Asn Thr Val His Ile Asp Leu Ser
            1045                1050                1055

Ala Leu Asn Pro Glu Leu Val Gln Ala Val Gln His Val Val Ile Gly
            1060                1065                1070

Pro Ser Ser Leu Ile Val His Phe Asn Glu Val Ile Gly Arg Gly His
            1075                1080                1085

Phe Gly Cys Val Tyr His Gly Thr Leu Leu Asp Asn Asp Gly Lys Lys
            1090                1095                1100

Ile His Cys Ala Val Lys Ser Leu Asn Arg Ile Thr Asp Ile Gly Glu
1105                1110                1115                1120

Val Ser Gln Phe Leu Thr Glu Gly Ile Ile Met Lys Asp Phe Ser His
            1125                1130                1135

Pro Asn Val Leu Ser Leu Leu Gly Ile Cys Leu Arg Ser Glu Gly Ser
            1140                1145                1150

Pro Leu Val Val Leu Pro Tyr Met Lys His Gly Asp Leu Arg Asn Phe
            1155                1160                1165

Ile Arg Asn Glu Thr His Asn Pro Thr Val Lys Asp Leu Ile Gly Phe
            1170                1175                1180

Gly Leu Gln Val Ala Lys Gly Met Lys Tyr Leu Ala Ser Lys Lys Phe
1185                1190                1195                1200

Val His Arg Asp Leu Ala Ala Arg Asn Cys Met Leu Asp Glu Lys Phe
            1205                1210                1215

Thr Val Lys Val Ala Asp Phe Gly Leu Ala Arg Asp Met Tyr Asp Lys
            1220                1225                1230

Glu Tyr Tyr Ser Val His Asn Lys Thr Gly Ala Lys Leu Pro Val Lys
            1235                1240                1245

Trp Met Ala Leu Glu Ser Leu Gln Thr Gln Lys Phe Thr Thr Lys Ser
            1250                1255                1260

Asp Val Trp Ser Phe Gly Val Leu Leu Trp Glu Leu Met Thr Arg Gly
1265                1270                1275                1280

Ala Pro Pro Tyr Pro Asp Val Asn Thr Phe Asp Ile Thr Val Tyr Leu
            1285                1290                1295

Leu Gln Gly Arg Arg Leu Leu Gln Pro Glu Tyr Cys Pro Asp Pro Leu
            1300                1305                1310

Tyr Glu Val Met Leu Lys Cys Trp His Pro Lys Ala Glu Met Arg Pro
            1315                1320                1325

Ser Phe Ser Glu Leu Val Ser Arg Ile Ser Ala Ile Phe Ser Thr Phe
            1330                1335                1340

Ile Gly Glu His Tyr Val His Val Asn Ala Thr Tyr Val Asn Val Lys
1345                1350                1355                1360

Cys Val Ala Pro Tyr Pro Ser Leu Leu Ser Ser Glu Asp Asn Ala Asp
            1365                1370                1375

Asp Glu Val Asp Thr Arg Pro Ala Ser Phe Trp Glu Thr Ser
            1380                1385                1390

<210> SEQ ID NO 15
<211> LENGTH: 240
<212> TYPE: PRT
<213> ORGANISM: Homo sapiens

<400> SEQUENCE: 15

Met Thr Pro His Arg Leu Leu Pro Pro Leu Leu Leu Leu Ala Leu
 1               5                  10                  15

Leu Leu Ala Ala Ser Pro Gly Gly Ala Leu Ala Arg Cys Pro Gly Cys

-continued

```
                 20                  25                  30
Gly Gln Gly Val Gln Ala Gly Cys Pro Gly Gly Cys Val Glu Glu
             35                  40                  45
Asp Gly Gly Ser Pro Ala Glu Gly Cys Ala Glu Ala Glu Gly Cys Leu
         50                  55                  60
Arg Arg Glu Gly Gln Glu Cys Gly Val Tyr Thr Pro Asn Cys Ala Pro
 65                  70                  75                  80
Gly Leu Gln Cys His Pro Pro Lys Asp Asp Glu Ala Pro Leu Arg Ala
                 85                  90                  95
Leu Leu Leu Gly Arg Gly Arg Cys Leu Pro Ala Arg Ala Pro Ala Val
             100                 105                 110
Ala Glu Glu Asn Pro Lys Glu Ser Lys Pro Gln Ala Gly Thr Ala Arg
             115                 120                 125
Pro Gln Asp Val Asn Arg Arg Asp Gln Gln Arg Asn Pro Gly Thr Ser
             130                 135                 140
Thr Thr Pro Ser Gln Pro Asn Ser Ala Gly Val Gln Asp Thr Glu Met
145                 150                 155                 160
Gly Pro Cys Arg Arg His Leu Asp Ser Val Leu Gln Gln Leu Gln Thr
                 165                 170                 175
Glu Val Tyr Arg Gly Ala Gln Thr Leu Tyr Val Pro Asn Cys Asp His
             180                 185                 190
Arg Gly Phe Tyr Arg Lys Arg Gln Cys Arg Ser Ser Gln Gly Gln Arg
             195                 200                 205
Arg Gly Pro Cys Trp Cys Val Asp Arg Met Gly Lys Ser Leu Pro Gly
             210                 215                 220
Ser Pro Asp Gly Asn Gly Ser Ser Ser Cys Pro Thr Gly Ser Ser Gly
225                 230                 235                 240

<210> SEQ ID NO 16
<211> LENGTH: 266
<212> TYPE: PRT
<213> ORGANISM: Homo sapiens

<400> SEQUENCE: 16

Met Met Ala Leu Gly Ala Ala Gly Ala Thr Arg Val Phe Val Ala Met
 1               5                  10                  15
Val Ala Ala Ala Leu Gly Gly His Pro Leu Leu Gly Val Ser Ala Thr
                 20                  25                  30
Leu Asn Ser Val Leu Asn Ser Asn Ala Ile Lys Asn Leu Pro Pro Pro
             35                  40                  45
Leu Gly Gly Ala Ala Gly His Pro Gly Ser Ala Val Ser Ala Ala Pro
         50                  55                  60
Gly Ile Leu Tyr Pro Gly Gly Asn Lys Tyr Gln Thr Ile Asp Asn Tyr
 65                  70                  75                  80
Gln Pro Tyr Pro Cys Ala Glu Asp Glu Glu Cys Gly Thr Asp Glu Tyr
                 85                  90                  95
Cys Ala Ser Pro Thr Arg Gly Gly Asp Ala Gly Val Gln Ile Cys Leu
             100                 105                 110
Ala Cys Arg Lys Arg Arg Lys Arg Cys Met Arg His Ala Met Cys Cys
             115                 120                 125
Pro Gly Asn Tyr Cys Lys Asn Gly Ile Cys Val Ser Ser Asp Gln Asn
             130                 135                 140
His Phe Arg Gly Glu Ile Glu Glu Thr Ile Thr Glu Ser Phe Gly Asn
145                 150                 155                 160
```

-continued

```
Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265
```

<210> SEQ ID NO 17
<211> LENGTH: 266
<212> TYPE: PRT
<213> ORGANISM: Homo sapiens

<400> SEQUENCE: 17

```
Met Met Ala Leu Gly Ala Ala Gly Ala Thr Arg Val Phe Val Ala Met
 1               5                  10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
 65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265
```

<210> SEQ ID NO 18
<211> LENGTH: 1179
<212> TYPE: PRT
<213> ORGANISM: Homo sapiens

<400> SEQUENCE: 18

```
Met Ala Ala Cys Gly Arg Val Arg Arg Met Phe Arg Leu Ser Ala Ala
 1               5                  10                  15

Leu His Leu Leu Leu Phe Ala Ala Gly Ala Glu Lys Leu Pro Gly
             20                  25                  30

Gln Gly Val His Ser Gln Gly Gln Gly Pro Gly Ala Asn Phe Val Ser
             35                  40                  45

Phe Val Gly Gln Ala Gly Gly Gly Pro Ala Gly Gln Gln Leu Pro
 50                  55                  60

Gln Leu Pro Gln Ser Ser Gln Leu Gln Gln Gln Gln Gln Gln Gln Gln
65                  70                  75                  80

Gln Gln Gln Gln Pro Gln Pro Pro Gln Pro Pro Phe Pro Ala Gly Gly
                 85                  90                  95

Pro Pro Ala Arg Arg Gly Gly Ala Gly Ala Gly Gly Trp Lys Leu
                100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
                180                 185                 190

Glu Pro Val Gly Lys Gly Tyr Met Val Ser Cys Leu Val Asp His Arg
                195                 200                 205

Gly Asn Ile Thr Glu Tyr Gln Cys His Gln Tyr Ile Thr Lys Met Thr
            210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
                260                 265                 270

Gly Leu Val Lys Glu Ala Glu Glu Arg Glu Pro Lys Ile Gln Val Ser
            275                 280                 285

Glu Leu Cys Lys Lys Ala Ile Leu Arg Val Ala Glu Leu Ser Ser Asp
        290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Gly Gly Arg Val Tyr Lys
                325                 330                 335

Cys Leu Phe Asn His Lys Phe Glu Glu Ser Met Ser Glu Lys Cys Arg
                340                 345                 350

Glu Ala Leu Thr Thr Arg Gln Lys Leu Ile Ala Gln Asp Tyr Lys Val
            355                 360                 365

Ser Tyr Ser Leu Ala Lys Ser Cys Lys Ser Asp Leu Lys Lys Tyr Arg
```

-continued

```
                370                 375                 380
Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
                405                 410                 415

Ser Glu Cys Gln Gly Glu Met Leu Asp Tyr Arg Arg Met Leu Met Glu
            420                 425                 430

Asp Phe Ser Leu Ser Pro Glu Ile Ile Leu Ser Cys Arg Gly Glu Ile
                435                 440                 445

Glu His His Cys Ser Gly Leu His Arg Lys Gly Arg Thr Leu His Cys
            450                 455                 460

Leu Met Lys Val Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
                485                 490                 495

Tyr Arg Ile Asp Arg Ala Leu Asn Glu Ala Cys Glu Ser Val Ile Gln
                500                 505                 510

Thr Ala Cys Lys His Ile Arg Ser Gly Asp Pro Met Ile Leu Ser Cys
            515                 520                 525

Leu Met Glu His Leu Tyr Thr Glu Lys Met Val Glu Asp Cys Glu His
            530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
                565                 570                 575

Thr His Gly Trp Asn Glu Thr Ser Glu Phe Met Pro Gln Gly Ala Val
            580                 585                 590

Phe Ser Cys Leu Tyr Arg His Ala Tyr Arg Thr Glu Glu Gln Gly Arg
            595                 600                 605

Arg Leu Ser Arg Glu Cys Arg Ala Glu Val Gln Arg Ile Leu His Gln
            610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
                660                 665                 670

Asp Ile Val Gly Asn Leu Thr Glu Leu Glu Ser Glu Asp Ile Gln Ile
            675                 680                 685

Glu Ala Leu Leu Met Arg Ala Cys Glu Pro Ile Ile Gln Asn Phe Cys
690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
                725                 730                 735

Gly Val Thr His Phe Gln Leu Val Gln Met Lys Asp Phe Arg Phe Ser
            740                 745                 750

Tyr Lys Phe Lys Met Ala Cys Lys Glu Asp Val Leu Lys Leu Cys Pro
            755                 760                 765

Asn Ile Lys Lys Lys Val Asp Val Val Ile Cys Leu Ser Thr Thr Val
            770                 775                 780

Arg Asn Asp Thr Leu Gln Glu Ala Lys Glu His Arg Val Ser Leu Lys
785                 790                 795                 800
```

```
Cys Arg Arg Gln Leu Arg Val Glu Glu Leu Glu Met Thr Glu Asp Ile
                805                 810                 815

Arg Leu Glu Pro Asp Leu Tyr Glu Ala Cys Lys Ser Asp Ile Lys Asn
            820                 825                 830

Phe Cys Ser Ala Val Gln Tyr Gly Asn Ala Gln Ile Ile Glu Cys Leu
        835                 840                 845

Lys Glu Asn Lys Lys Gln Leu Ser Thr Arg Cys His Gln Lys Val Phe
    850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
                885                 890                 895

Ser Lys Thr Met Leu Gln Cys Leu Lys Gln Asn Lys Asn Ser Glu Leu
            900                 905                 910

Met Asp Pro Lys Cys Lys Gln Met Ile Thr Lys Arg Gln Ile Thr Gln
        915                 920                 925

Asn Thr Asp Tyr Arg Leu Asn Pro Met Leu Arg Lys Ala Cys Lys Ala
    930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
                965                 970                 975

Asp Gln Arg Leu Ser Ser Asp Cys Glu Asp Gln Ile Arg Ile Ile Ile
            980                 985                 990

Gln Glu Ser Ala Leu Asp Tyr Arg Leu Asp Pro Gln Leu Gln Leu His
        995                 1000                1005

Cys Ser Asp Glu Ile Ser Ser Leu Cys Ala Glu Glu Ala Ala Ala Gln
    1010                1015                1020

Glu Gln Thr Gly Gln Val Glu Glu Cys Leu Lys Val Asn Leu Leu Lys
1025                1030                1035                1040

Ile Lys Thr Glu Leu Cys Lys Lys Glu Val Leu Asn Met Leu Lys Glu
                1045                1050                1055

Ser Lys Ala Asp Ile Phe Val Asp Pro Val Leu His Thr Ala Cys Ala
            1060                1065                1070

Leu Asp Ile Lys His His Cys Ala Ala Ile Thr Pro Gly Arg Gly Arg
        1075                1080                1085

Gln Met Ser Cys Leu Met Glu Ala Leu Glu Asp Lys Arg Val Arg Leu
    1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
                1125                1130                1135

Gln Val Met Thr Ser Pro Ser Lys Asn Tyr Ile Leu Ser Val Ile Ser
            1140                1145                1150

Gly Ser Ile Cys Ile Leu Phe Leu Ile Gly Leu Met Cys Gly Arg Ile
        1155                1160                1165

Thr Lys Arg Val Thr Arg Glu Leu Lys Asp Arg
    1170                1175

<210> SEQ ID NO 19
<211> LENGTH: 1179
<212> TYPE: PRT
<213> ORGANISM: Homo sapiens
```

```
<400> SEQUENCE: 19

Met Ala Ala Cys Gly Arg Val Arg Arg Met Phe Arg Leu Ser Ala Ala
 1               5                  10                  15

Leu His Leu Leu Leu Leu Phe Ala Ala Gly Ala Glu Lys Leu Pro Gly
                20                  25                  30

His Gly Val His Ser Gln Gly Gln Gly Pro Gly Ala Asn Phe Val Ser
            35                  40                  45

Phe Val Gly Gln Ala Gly Gly Gly Pro Ala Gly Gln Gln Leu Pro
    50                  55                  60

Gln Leu Leu Gln Ser Ser Gln Leu Gln Gln Gln Gln Gln Gln Gln Gln
65                  70                  75                  80

Gln Gln Gln Gln Leu Gln Pro Pro Gln Pro Phe Pro Ala Gly Gly
                85                  90                  95

Pro Pro Ala Arg Arg Gly Gly Ala Gly Ala Gly Gly Gly Trp Lys Leu
                100                 105                 110

Ala Glu Glu Glu Ser Cys Arg Glu Asp Val Thr Arg Val Cys Pro Lys
                115                 120                 125

His Thr Trp Ser Asn Asn Leu Ala Val Leu Glu Cys Leu Gln Asp Val
            130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Cys Ala Asp
                180                 185                 190

Glu Pro Val Gly Lys Gly Tyr Met Val Ser Cys Leu Val Asp His Arg
                195                 200                 205

Gly Asn Ile Thr Glu Tyr Gln Cys His Gln Tyr Ile Thr Lys Met Thr
            210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
                260                 265                 270

Gly Leu Val Lys Glu Ala Glu Arg Glu Pro Lys Ile Gln Val Ser
            275                 280                 285

Glu Leu Cys Lys Lys Ala Ile Leu Arg Val Ala Glu Leu Ser Ser Asp
                290                 295                 300

Asp Phe His Leu Asp Arg His Leu Tyr Phe Ala Cys Arg Asp Arg
305                 310                 315                 320

Glu Arg Phe Cys Glu Asn Thr Gln Ala Gly Glu Gly Arg Val Tyr Lys
                325                 330                 335

Cys Leu Phe Asn His Lys Phe Glu Glu Ser Met Ser Glu Lys Cys Arg
                340                 345                 350

Glu Ala Leu Thr Thr Arg Gln Lys Leu Ile Ala Gln Asp Tyr Lys Val
            355                 360                 365

Ser Tyr Ser Leu Ala Lys Ser Cys Lys Ser Asp Leu Lys Lys Tyr Arg
    370                 375                 380

Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
                405                 410                 415
```

-continued

Ser Glu Cys Gln Gly Glu Met Leu Asp Tyr Arg Arg Met Leu Met Glu
                420                 425                 430

Asp Phe Ser Leu Ser Pro Glu Ile Ile Leu Ser Cys Arg Gly Glu Ile
            435                 440                 445

Glu His His Cys Ser Gly Leu His Arg Lys Gly Arg Thr Leu His Cys
        450                 455                 460

Leu Met Lys Val Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
                485                 490                 495

Tyr Arg Ile Asp Arg Ala Leu Asn Glu Ala Cys Glu Ser Val Ile Gln
            500                 505                 510

Thr Ala Cys Lys His Ile Arg Ser Gly Asp Pro Met Ile Leu Ser Cys
        515                 520                 525

Leu Met Glu His Leu Tyr Thr Glu Lys Met Val Glu Asp Cys Glu His
530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
                565                 570                 575

Thr His Gly Trp Asn Glu Thr Ser Glu Phe Met Pro Gln Gly Ala Val
            580                 585                 590

Phe Ser Cys Leu Tyr Arg His Ala Tyr Arg Thr Glu Glu Gln Gly Arg
        595                 600                 605

Arg Leu Ser Arg Glu Cys Arg Ala Glu Val Gln Arg Ile Leu His Gln
610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
            660                 665                 670

Asp Ile Val Gly Asn Leu Thr Glu Leu Glu Ser Glu Asp Ile Gln Ile
        675                 680                 685

Glu Ala Leu Leu Met Arg Ala Cys Glu Pro Ile Ile Gln Asn Phe Cys
690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
                725                 730                 735

Gly Val Thr His Phe Gln Leu Val Gln Met Lys Asp Phe Arg Phe Ser
            740                 745                 750

Tyr Lys Phe Lys Met Ala Cys Lys Glu Asp Val Leu Lys Leu Cys Pro
        755                 760                 765

Asn Ile Lys Lys Lys Val Asp Val Val Ile Cys Leu Ser Thr Thr Val
770                 775                 780

Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
                805                 810                 815

Arg Leu Glu Pro Asp Leu Tyr Glu Ala Cys Lys Ser Asp Ile Lys Asn
            820                 825                 830

-continued

Phe Cys Ser Ala Val Gln Tyr Gly Asn Ala Gln Ile Ile Glu Cys Leu
            835                 840                 845

Lys Glu Asn Lys Lys Gln Leu Ser Thr Arg Cys His Gln Lys Val Phe
        850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
            885                 890                 895

Ser Lys Thr Met Leu Gln Cys Leu Lys Gln Asn Lys Asn Ser Glu Leu
        900                 905                 910

Met Asp Pro Lys Cys Lys Gln Met Ile Thr Lys Arg Gln Ile Thr Gln
            915                 920                 925

Asn Thr Asp Tyr Arg Leu Asn Pro Met Leu Arg Lys Ala Cys Lys Ala
        930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
            965                 970                 975

Asp Gln Arg Leu Ser Ser Asp Cys Glu Asp Gln Ile Arg Ile Ile Ile
        980                 985                 990

Gln Glu Ser Ala Leu Asp Tyr Arg Leu Asp Pro Gln Leu Gln Leu His
    995                 1000                1005

Cys Ser Asp Glu Ile Ser Ser Leu Cys Ala Glu Glu Ala Ala Ala Gln
        1010                1015                1020

Glu Gln Thr Gly Gln Val Glu Glu Cys Leu Lys Val Asn Leu Leu Lys
1025                1030                1035                1040

Ile Lys Thr Glu Leu Cys Lys Lys Glu Val Leu Asn Met Leu Lys Glu
            1045                1050                1055

Ser Lys Ala Asp Ile Phe Val Asp Pro Val Leu His Thr Ala Cys Ala
        1060                1065                1070

Leu Asp Ile Lys His His Cys Ala Ala Ile Thr Pro Gly Arg Gly Arg
        1075                1080                1085

Gln Met Ser Cys Leu Met Glu Ala Leu Glu Asp Lys Arg Val Arg Leu
        1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
            1125                1130                1135

Gln Val Met Thr Ser Pro Ser Lys Asn Tyr Ile Leu Ser Val Ile Ser
        1140                1145                1150

Gly Ser Ile Cys Ile Leu Phe Leu Ile Gly Leu Met Cys Gly Arg Ile
        1155                1160                1165

Thr Lys Arg Val Thr Arg Glu Leu Lys Asp Arg
    1170                1175

<210> SEQ ID NO 20
<211> LENGTH: 1179
<212> TYPE: PRT
<213> ORGANISM: Homo sapiens

<400> SEQUENCE: 20

Met Ala Ala Cys Gly Arg Val Arg Arg Met Phe Arg Leu Ser Ala Ala
1               5                   10                  15

Leu His Leu Leu Leu Leu Phe Ala Ala Gly Ala Glu Lys Leu Pro Gly
            20                  25                  30

-continued

```
Gln Gly Val His Ser Gln Gly Gln Gly Pro Gly Ala Asn Phe Val Ser
         35                  40                  45
Phe Val Gly Gln Ala Gly Gly Gly Pro Ala Gly Gln Gln Leu Pro
 50                  55                  60
Gln Leu Pro Gln Ser Ser Gln Leu Gln Gln Gln Gln Gln Gln Gln
 65                  70                  75                  80
Gln Gln Gln Gln Pro Gln Pro Pro Gln Pro Phe Pro Ala Gly Gly
                 85                  90                  95
Pro Pro Ala Arg Arg Gly Gly Ala Gly Ala Gly Gly Trp Lys Leu
                100                 105                 110
Ala Glu Glu Glu Ser Cys Arg Glu Asp Val Thr Arg Val Cys Pro Lys
            115                 120                 125
His Thr Trp Ser Asn Asn Leu Ala Val Leu Glu Cys Leu Gln Asp Val
        130                 135                 140
Arg Glu Pro Glu Asn Glu Ile Ser Ser Asp Cys Asn His Leu Leu Trp
145                 150                 155                 160
Asn Tyr Lys Leu Asn Leu Thr Thr Asp Pro Lys Phe Glu Ser Val Ala
                165                 170                 175
Arg Glu Val Cys Lys Ser Thr Ile Thr Glu Ile Lys Glu Cys Ala Asp
                180                 185                 190
Glu Pro Val Gly Lys Gly Tyr Met Val Ser Cys Leu Val Asp His Arg
            195                 200                 205
Gly Asn Ile Thr Glu Tyr Gln Cys His Gln Tyr Ile Thr Lys Met Thr
        210                 215                 220
Ala Ile Ile Phe Ser Asp Tyr Arg Leu Ile Cys Gly Phe Met Asp Asp
225                 230                 235                 240
Cys Lys Asn Asp Ile Asn Ile Leu Lys Cys Gly Ser Ile Arg Leu Gly
                245                 250                 255
Glu Lys Asp Ala His Ser Gln Gly Glu Val Val Ser Cys Leu Glu Lys
            260                 265                 270
Gly Leu Val Lys Glu Ala Glu Arg Glu Pro Lys Ile Gln Val Ser
        275                 280                 285
Glu Leu Cys Lys Lys Ala Ile Leu Arg Val Ala Glu Leu Ser Ser Asp
290                 295                 300
Asp Phe His Leu Asp Arg His Leu Tyr Phe Ala Cys Arg Asp Asp Arg
305                 310                 315                 320
Glu Arg Phe Cys Glu Asn Thr Gln Ala Gly Glu Gly Arg Val Tyr Lys
                325                 330                 335
Cys Leu Phe Asn His Lys Phe Glu Glu Ser Met Ser Glu Lys Cys Arg
            340                 345                 350
Glu Ala Leu Thr Thr Arg Gln Lys Leu Ile Ala Gln Asp Tyr Lys Val
        355                 360                 365
Ser Tyr Ser Leu Ala Lys Ser Cys Lys Ser Asp Leu Lys Lys Tyr Arg
    370                 375                 380
Cys Asn Val Glu Asn Leu Pro Arg Ser Arg Glu Ala Arg Leu Ser Tyr
385                 390                 395                 400
Leu Leu Met Cys Leu Glu Ser Ala Val His Arg Gly Arg Gln Val Ser
                405                 410                 415
Ser Glu Cys Gln Gly Glu Met Leu Asp Tyr Arg Arg Met Leu Met Glu
            420                 425                 430
Asp Phe Ser Leu Ser Pro Glu Ile Ile Leu Ser Cys Arg Gly Glu Ile
        435                 440                 445
```

-continued

```
Glu His His Cys Ser Gly Leu His Arg Lys Gly Arg Thr Leu His Cys
    450                 455                 460
Leu Met Lys Val Val Arg Gly Glu Lys Gly Asn Leu Gly Met Asn Cys
465                 470                 475                 480
Gln Gln Ala Leu Gln Thr Leu Ile Gln Glu Thr Asp Pro Gly Ala Asp
                485                 490                 495
Tyr Arg Ile Asp Arg Ala Leu Asn Glu Ala Cys Glu Ser Val Ile Gln
                500                 505                 510
Thr Ala Cys Lys His Ile Arg Ser Gly Asp Pro Met Ile Leu Ser Cys
            515                 520                 525
Leu Met Glu His Leu Tyr Thr Glu Lys Met Val Glu Asp Cys Glu His
            530                 535                 540
Arg Leu Leu Glu Leu Gln Tyr Phe Ile Ser Arg Asp Trp Lys Leu Asp
545                 550                 555                 560
Pro Val Leu Tyr Arg Lys Cys Gln Gly Asp Ala Ser Arg Leu Cys His
                565                 570                 575
Thr His Gly Trp Asn Glu Thr Ser Glu Phe Met Pro Gln Gly Ala Val
                580                 585                 590
Phe Ser Cys Leu Tyr Arg His Ala Tyr Arg Thr Glu Glu Gln Gly Arg
            595                 600                 605
Arg Leu Ser Arg Glu Cys Arg Ala Glu Val Gln Arg Ile Leu His Gln
            610                 615                 620
Arg Ala Met Asp Val Lys Leu Asp Pro Ala Leu Gln Asp Lys Cys Leu
625                 630                 635                 640
Ile Asp Leu Gly Lys Trp Cys Ser Glu Lys Thr Glu Thr Gly Gln Glu
                645                 650                 655
Leu Glu Cys Leu Gln Asp His Leu Asp Asp Leu Val Val Glu Cys Arg
            660                 665                 670
Asp Ile Val Gly Asn Leu Thr Glu Leu Glu Ser Glu Asp Ile Gln Ile
            675                 680                 685
Glu Ala Leu Leu Met Arg Ala Cys Glu Pro Ile Ile Gln Asn Phe Cys
690                 695                 700
His Asp Val Ala Asp Asn Gln Ile Asp Ser Gly Asp Leu Met Glu Cys
705                 710                 715                 720
Leu Ile Gln Asn Lys His Gln Lys Asp Met Asn Glu Lys Cys Ala Ile
                725                 730                 735
Gly Val Thr His Phe Gln Leu Val Gln Met Lys Asp Phe Arg Phe Ser
                740                 745                 750
Tyr Lys Phe Lys Met Ala Cys Lys Glu Asp Val Leu Lys Leu Cys Pro
            755                 760                 765
Asn Ile Lys Lys Lys Val Asp Val Val Ile Cys Leu Ser Thr Thr Val
            770                 775                 780
Arg Asn Asp Thr Leu Gln Glu Ala Lys Glu His Arg Val Ser Leu Lys
785                 790                 795                 800
Cys Arg Arg Gln Leu Arg Val Glu Glu Leu Glu Met Thr Glu Asp Ile
                805                 810                 815
Arg Leu Glu Pro Asp Leu Tyr Glu Ala Cys Lys Ser Asp Ile Lys Asn
                820                 825                 830
Phe Cys Ser Ala Val Gln Tyr Gly Asn Ala Gln Ile Ile Glu Cys Leu
            835                 840                 845
Lys Glu Asn Lys Lys Gln Leu Ser Thr Arg Cys His Gln Lys Val Phe
850                 855                 860
Lys Leu Gln Glu Thr Glu Met Met Asp Pro Glu Leu Asp Tyr Thr Leu
```

-continued

```
            865                 870                 875                 880
Met Arg Val Cys Lys Gln Met Ile Lys Arg Phe Cys Pro Glu Ala Asp
                885                 890                 895

Ser Lys Thr Met Leu Gln Cys Leu Lys Gln Asn Lys Asn Ser Glu Leu
            900                 905                 910

Met Asp Pro Lys Cys Lys Gln Met Ile Thr Lys Arg Gln Ile Thr Gln
            915                 920                 925

Asn Thr Asp Tyr Arg Leu Asn Pro Met Leu Arg Lys Ala Cys Lys Ala
            930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
                965                 970                 975

Asp Gln Arg Leu Ser Ser Asp Cys Glu Asp Gln Ile Arg Ile Ile Ile
            980                 985                 990

Gln Glu Ser Ala Leu Asp Tyr Arg Leu Asp Pro Gln Leu Gln Leu His
            995                 1000                1005

Cys Ser Asp Glu Ile Ser Ser Leu Cys Ala Glu Glu Ala Ala Gln
        1010                1015                1020

Glu Gln Thr Gly Gln Val Glu Cys Leu Lys Val Asn Leu Leu Lys
1025                1030                1035                1040

Ile Lys Thr Glu Leu Cys Lys Lys Glu Val Leu Asn Met Leu Lys Glu
                1045                1050                1055

Ser Lys Ala Asp Ile Phe Val Asp Pro Val Leu His Thr Ala Cys Ala
            1060                1065                1070

Leu Asp Ile Lys His His Cys Ala Ala Ile Thr Pro Gly Arg Gly Arg
        1075                1080                1085

Gln Met Ser Cys Leu Met Glu Ala Leu Glu Asp Lys Arg Val Arg Leu
            1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
                1125                1130                1135

Gln Val Met Thr Ser Pro Ser Lys Asn Tyr Ile Leu Ser Val Ile Ser
            1140                1145                1150

Gly Ser Ile Cys Ile Leu Phe Leu Ile Gly Leu Met Cys Gly Arg Ile
        1155                1160                1165

Thr Lys Arg Val Thr Arg Glu Leu Lys Asp Arg
    1170                1175

<210> SEQ ID NO 21
<211> LENGTH: 97
<212> TYPE: PRT
<213> ORGANISM: Homo sapiens

<400> SEQUENCE: 21

Met Cys Ser Ser Leu Glu Gln Ala Leu Ala Val Leu Thr Thr Phe
1               5                   10                  15

His Lys Tyr Ser Cys Gln Glu Gly Asp Lys Phe Lys Leu Ser Lys Gly
            20                  25                  30

Glu Met Lys Glu Leu Leu His Lys Glu Leu Pro Ser Phe Val Gly Glu
        35                  40                  45

Lys Val Asp Glu Glu Gly Leu Lys Lys Leu Met Gly Ser Leu Asp Glu
    50                  55                  60
```

```
Asn Ser Asp Gln Gln Val Asp Phe Gln Glu Tyr Ala Val Phe Leu Ala
 65                  70                  75                  80

Leu Ile Thr Val Met Cys Asn Asp Phe Phe Gln Gly Cys Pro Asp Arg
                 85                  90                  95

Pro

<210> SEQ ID NO 22
<211> LENGTH: 98
<212> TYPE: PRT
<213> ORGANISM: Homo sapiens

<400> SEQUENCE: 22

Met Met Cys Ser Ser Leu Glu Gln Ala Leu Ala Val Leu Val Thr Thr
 1               5                  10                  15

Phe His Lys Tyr Ser Cys Gln Glu Gly Asp Lys Phe Lys Leu Ser Lys
                20                  25                  30

Gly Glu Met Lys Glu Leu Leu His Lys Glu Leu Pro Ser Phe Val Gly
             35                  40                  45

Glu Lys Val Asp Glu Glu Gly Leu Lys Lys Leu Met Gly Asn Leu Asp
 50                  55                  60

Glu Asn Ser Asp Gln Gln Val Asp Phe Gln Glu Tyr Ala Val Phe Leu
 65                  70                  75                  80

Ala Leu Ile Thr Val Met Cys Asn Asp Phe Phe Gln Gly Cys Pro Asp
                 85                  90                  95

Arg Pro

<210> SEQ ID NO 23
<211> LENGTH: 116
<212> TYPE: PRT
<213> ORGANISM: Homo sapiens

<400> SEQUENCE: 23

Met Gln Arg Leu Arg Trp Leu Arg Asp Trp Lys Ser Ser Gly Arg Gly
 1               5                  10                  15

Leu Thr Ala Ala Lys Glu Pro Gly Ala Arg Ser Ser Pro Leu Gln Ala
                20                  25                  30

Met Arg Ile Leu Gln Leu Ile Leu Leu Ala Leu Ala Thr Gly Leu Val
             35                  40                  45

Gly Gly Glu Thr Arg Ile Ile Lys Gly Phe Glu Cys Lys Pro His Ser
 50                  55                  60

Gln Pro Trp Gln Ala Ala Leu Phe Glu Lys Thr Arg Leu Leu Cys Gly
 65                  70                  75                  80

Ala Thr Leu Ile Ala Pro Arg Trp Leu Leu Thr Ala Ala His Cys Leu
                 85                  90                  95

Lys Pro Trp Pro Leu His Ser Ser Pro Gly Ala Ala Gln Pro Pro Glu
                100                 105                 110

Gly Gly Gly Leu
        115

<210> SEQ ID NO 24
<211> LENGTH: 63
<212> TYPE: DNA
<213> ORGANISM: Homo sapiens

<400> SEQUENCE: 24
tacctctgtg ccagcaggcc ggacgggagc tctggaaaca ccatatattt tggagaggga      60
agt                                                                    63
```

<210> SEQ ID NO 25
<211> LENGTH: 1669
<212> TYPE: DNA
<213> ORGANISM: Homo sapiens

<400> SEQUENCE: 25

| | | | | | |
|---|---|---|---|---|---|
| actttgttttt | tggacatagc | tgagccatgt | acttcaaaca | gaaggcagcc | aattactaac | 60 |
| ttctggttgc | taggtgtggc | ttcctttaaa | atcctataaa | atcagaagcc | caagtctcca | 120 |
| ctgccagtgt | gaaatcttca | gagaagaatt | tctctttagt | tctttgcaag | aaggtagaga | 180 |
| taaagggaag | gtgtgggaag | gacttgtgaa | atacatattc | gaggaaaaac | tatgcacaag | 240 |
| gccgtgcatt | taaaaataaa | ctccctaagg | ctggggtgaa | acctgctacg | gtctgcgcaa | 300 |
| gttgactgtt | aatgaatttg | attctcagac | acttttttcaa | aaatggcaat | ggtatcagaa | 360 |
| ttcctcaagc | aggcctggtt | tattgaaaat | gaagagcagg | aatatgttca | aactgtgaag | 420 |
| tcatccaaag | gtggtcccgg | atcagcggtg | agcccctatc | ctaccttcaa | tccatcctcg | 480 |
| gatgtcgctg | ccttgcataa | ggccataatg | gttaaaggtg | tggatgaagc | aaccatcatt | 540 |
| gacattctaa | ctaagcgaaa | caatgcacag | cgtcaacaga | tcaaagcagc | atatctccag | 600 |
| gaaacaggaa | agcccctgga | tgaaacactg | aagaaagccc | ttacaggtca | ccttgaggag | 660 |
| gttgttttag | ctctgctaaa | aactccagcg | caatttgatg | ctgatgaact | tcgtgctgcc | 720 |
| atgaagggcc | ttggaactga | tgaagatact | ctaattgaga | ttttggcatc | aagaactaac | 780 |
| aaagaaatca | gagacattaa | cagggtctac | agagaggaac | tgaagagaga | tctggccaaa | 840 |
| gacataacct | cagacacatc | tggagatttt | cggaacgctt | tgctttctct | tgctaagggt | 900 |
| gaccgatctg | aggactttgg | tgtgaatgaa | gacttggctg | attcagatgc | cagggccttg | 960 |
| tatgaagcag | gagaaaggag | aaaggggaca | gacgtaaacg | tgttcaatac | catccttacc | 1020 |
| accagaaagct | atccacaact | tcgcagagtg | tttcagaaat | acaccaagta | cagtaagcat | 1080 |
| gacatgaaca | agttctggaa | cctggagttg | aaaggtgaca | ttgagaaatg | cctcacagct | 1140 |
| atcgtgaagt | gcgccacaag | caaaccagct | ttctttgcag | agaagcttca | tcaagccatg | 1200 |
| aaaggtgttg | gaactcgcca | taaggcattg | atcaggatta | tggtttcccg | ttctgaaatt | 1260 |
| gacatgaatg | atatcaaagc | attctatcag | aagatgtatg | gtatctcccct | ttgccaagcc | 1320 |
| atcctggatg | aaaccaaagg | agattatgag | aaaatcctgg | tggctctttg | tggaggaaac | 1380 |
| taaacattcc | cttgatggtc | tcaagctatg | atcagaagac | tttaattata | tattttcatc | 1440 |
| ctataagctt | aaataggaaa | gtttcttcaa | caggattaca | gtgtagctac | ctacatgctg | 1500 |
| aaaaatatag | cctttaaatc | attttttatat | taaactctg | tataatagag | ataagtccat | 1560 |
| tttttaaaaa | tgttttcccc | aaaccataaa | accctataca | agttgttcta | gtaacaatac | 1620 |
| atgagaaaga | tgtctatgta | gctgaaaata | aaatgacgtc | acaagacaa | | 1669 |

<210> SEQ ID NO 26
<211> LENGTH: 1669
<212> TYPE: DNA
<213> ORGANISM: Homo sapiens

<400> SEQUENCE: 26

| | | | | | |
|---|---|---|---|---|---|
| actttgttttt | tggacatagc | tgagccatgt | acttcaaaca | gaaggcagcc | aattactaac | 60 |
| ttctggttgc | taggtgtggc | ttcctttaaa | atcctataaa | atcagaagcc | caagtctcca | 120 |
| ctgccagtgt | gaaatcttca | gagaagaatt | tctctttagt | tctttgcaag | aaggtagaga | 180 |

```
taaagggaag gtgtgggaag gacttgtgaa atacatattc gaggaaaaac tatgcacaag    240
gccgtgcatt taaaaataaa ctccctaagg ctggggtgaa acctgctacg gtctgcgcaa    300
gttgactgtt aatgaatttg attctcagac acttttccaa aaatggcaat ggtatcagaa    360
ttcctcaagc aggcctggtt tattgaaaat gaagagcagg aatatgttca aactgtgaag    420
tcatccaaag gtggtcccgg atcagcggtg agccctatc ctaccttcaa tccatcctcg    480
gatgtcgctg ccttgcataa ggccataatg gttaaaggtg tggatgaagc aaccatcatt    540
gacattctaa ctaagcgaaa caatgcacag cgtcaacaga tcaaagcagc atatctccag    600
gaaacaggaa agcccctgga tgaaacactg aagaaagccc ttacaggtca ccttgaggag    660
gttgttttag ctctgctaaa aactccagcg caatttgatg ctgatgaact tcgtgctgcc    720
atgaagggcc ttggaactga tgaagatact ctaattgaga ttttggcatc aagaactaac    780
aaagaaatca gagacattaa cagggtctac agagaggaac tgaagagaga tctggccaaa    840
gacataacct cagacacatc tggagatttt cggaacgctt tgctttctct tgctaagggt    900
gaccgatctg aggactttgg tgtgaatgaa gacttggctg attcagatgc cagggccttg    960
tatgaagcag gagaaaggag aaaggggaca gacgtaaacg tgttcaatac catccttacc   1020
accagaagct atccacaact tcgcagagtg tttcagaaat acaccaagta cagtaagcat   1080
gacatgaaca aagttctgga cctggagttg aaaggtgaca ttgagaaatg cctcacagct   1140
atcgtgaagt gcgccacaag caaaccagct ttctttgcag agaagcttca tcaagccatg   1200
aaaggtgttg gaactcgcca taggcattg atcaggatta tggtttcccg ttctgaaatt   1260
gacatgaatg atatcaaagc attctatcag aagatgtatg gtatctccct ttgccaagcc   1320
atcctggatg aaaccaaagg agattatgag aaaatcctgg tggctctttg tggaggaaac   1380
taaacattcc cttgatggtc tcaagctatg atcagaagac tttaattata tattttcatc   1440
ctataagctt aaataggaaa gtttcttcaa caggattaca gtgtagctac ctacatgctg   1500
aaaaatatag cctttaaatc atttttatat tataactctg tataatagag ataagtccat   1560
tttttaaaaa tgttttcccc aaaccataaa accctataca agttgttcta gtaacaatac   1620
atgagaaaga tgtctatgta gctgaaaata aaatgacgtc acaagacaa              1669
```

<210> SEQ ID NO 27
<211> LENGTH: 1560
<212> TYPE: DNA
<213> ORGANISM: Homo sapiens

<400> SEQUENCE: 27

```
actttgtttt tggacatagc tgagccatgt acttcaaaca gaaggcagcc aattactaac     60
ttctggttgc taggtgtggc ttcctttaaa atccatataaa atcagaagcc caagtctcca    120
ctgccagtgt gaaatcttca gagaagaatt tctctttagt tctttgcaag aaggtagaga   180
taaagagtct tgttatgtcg cccaggatgg agtgtagtga cacttttca aaaatggcaa    240 tggtatcaga attcctcaag caggcctggt ttattgaaaa tgaagagcag gaatatgttc    300
aaactgtgaa gtcatccaaa ggtggtcccg gatcagcggt gagcccctat cctaccttca    360
atccatcctc ggatgtcgct gccttgcata aggccataat ggttaaaggt gtggatgaag    420
caaccatcat tgacattcta actaagcgaa acaatgcaca gcgtcaacag atcaaagcag    480
catatctcca ggaaacagga agcccctgg atgaaacact gaagaaagcc cttacaggtc    540
accttgagga ggttgtttta gctctgctaa aaactccagc gcaatttgat gctgatgaac    600
ttcgtgctgc catgaagggc cttggaactg atgaagatac tctaattgag attttggcat    660
```

```
caagaactaa caaagaaatc agagacatta acagggtcta cagagaggaa ctgaagagag    720
atctggccaa agacataacc tcagacacat ctggagattt cggaacgct  ttgctttctc    780 ttgctaaggg tgaccgatct gaggactttg gtgtgaatga agacttggct gattcagatg    840
ccagggcctt gtatgaagca ggagaaagga gaaagggac  agacgtaaac gtgttcaata    900
ccatccttac caccagaagc tatccacaac ttcgcagagt gtttcagaaa tacaccaagt    960
acagtaagca tgacatgaac aaagttctgg acctggagtt gaaggtgac  attgagaaat   1020 gcctcacagc tatcgtgaag tgcgccacaa gcaaaccagc tttctttgca gagaagcttc   1080
atcaagccat gaaaggtgtt ggaactcgcc ataaggcatt gatcaggatt atggtttccc   1140
gttctgaaat tgcatgaat  gatatcaaag cattctatca agatgtat   ggtatctccc   1200 tttgccaagc catcctggat gaaccaaag  gagattatga gaaaatcctg gtggctcttt   1260
gtggaggaaa ctaaacattc ccttgatggt ctcaagctat gatcagaaga ctttaattat   1320
atattttcat cctataagct aaataggaa  agtttcttca acaggattac agtgtagcta   1380
cctacatgct gaaaaatata gcctttaaat cattttata  ttataactct gtataataga   1440
gataagtcca ttttttaaaa atgttttccc caaaccataa aaccctatac aagttgttct   1500
agtaacaata catgagaaag atgtctatgt agctgaaaat aaaatgacgt cacaagacaa   1560

<210> SEQ ID NO 28
<211> LENGTH: 4079
<212> TYPE: DNA
<213> ORGANISM: Homo sapiens

<400> SEQUENCE: 28
tggaaaacct aaaaagaagg gaaatacttt ctgggtagtg tcagatacat tatcctaggg     60
gaatgtcagt gaggccctcc aacagctatt ccacttgatt gttgcatgag ctaatggcca    120
taaaactcct tagaaaagca caaagcaaaa ctaaagaaga gtatttacta gtgttggata    180
tatttgtaaa agtgagatta caaatcatgt atctggctat tttttcttta aacatgttcc    240
ttcaagaatt tttctgttcg ttcatttaa  atatttatta aatgttctga tttcttatgt    300
tcactgctag ctaattaaca aggatggaat ttttcttgcc ttggttatat ctaaaagatt    360
gtaaaaactt tgagaaagca atgttgccct cttttccacag gagtattttg gtagctgtaa   420
gagaatgcac attgcaaatg actcaaatgt ggtaaaatgt tggtttcata attctgaaat    480
ggcctcttcc ccaaaagtga cagtaacacc ctagctccag gctcaaccac atccagcaca    540
tagccaacat ttaacagatg ttgacaaaat ggttaataat aatattatta aggaaccagc    600
cagagtttca tgcttattaa atactttttc aaccagaagg tctgcaaagg ttgatttctg    660
aatatgacgt tagctctctc tagacctatt aatttacgac atttcaaatc agaggtaaac    720
cagcagacct attattttc  aatgataaac tataaacagt tttttgaagt caactatttc    780
cttttccttt aaaattggac agaatttcat caggaagctc agaacaatcc aatttatata    840
atgccttcct tcattatgct aattttcttc atcttcatct acttgaagta atatttaaga    900
ttggcacttc agagctgtaa atggatctta gatgataatt acttcaacat tcttatttta    960
taaacgaaga ccctctggag aagctaaatg ttttttcttga ggtcagatcg ccagataatc   1020
aagaaccagt atacttcaat ttgtatttta tatcctatag ttgtgggtag aaaatgttca   1080
ttaaattagt gtagatatgt ttttaaaat  attagcaatg atacatgata ttcattcaat   1140
aatacttatt aacatcctaa attccaggca ttttgctagg gattggaagt acatacataa   1200
```

```
tgaatattat tatttgtatg ttagcacggg cctcatggcc tgctcctggg gaatataaac    1260
aagccaatgg aaagtgataa tacagaaagg tggggctggt gtaggggtga agtcaggatg    1320
ctttgggaga gcatggaagg tcaccgaatc cagtgctgag gaactaatga agggtttctg    1380
aagaacgtga tgagatcaat gctgatgagt cacttagaag tagcaattag ttaggcaaag    1440
ggaagtgaat gtggaggagg aacaagcatt ccaggcaaga agaacaccct atcgaaaagc    1500
ctggaagcaa acattagtg aggctacctt tcataaattg ctttctgtaa gtcatgccat    1560
tgtgtagtct taattgcttt ctctcaccag ggaaggtgtg ggaaggactt gtgaaataca    1620
tattcgagga aaaactatgc acaaggccgt gcatttaaaa ataaactccc taaggctggg    1680
gtgaaacctg ctacggtctg cgcaagttga ctgttaatga atttgattct caggtgtgag    1740
tgattaaaag aacactgatc atgtcatttt ctttttggtc actaattccc tccctccctt    1800
ctctttcttt tcttttttct tttcttttct ttttctttct ttcttcccga cagaagaaag    1860
actccatctc aaaaaaaaaa aaaaaaaaaa aagcaatcat taagcttttc atctagccat    1920
tacttttgta caggctctca ttaattccac atagatggtc taatggtcta ctaaatagta    1980
ttctaatcct ccatcttgtc tatctcttag ccattctcca tgataaagga tgaatggtct    2040
ttcggaaaca taaatgaaac catgctgctt taaaaaaaca aacaaacaaa aagaaaccca    2100
ttaatgtttt cccaaagctt tgtggacaca ttgaagcttc ttgttcagc ttctgccaac    2160 atttctcgct ccagcaaact ttcttctgct tcccaaatat gacaagcttc ttctttaact    2220
tttctgccag gttaatcttg actcatttca agagaggctt gggtcagcca gggcctactc    2280
taagaagttt cttagccct tatgttttcc tatggagagc acacactagc tttaagtcct    2340
gagggtactt aagatgatat ttcaatgttt ttgtactctt agtgcttggc atatggtggg    2400
tggtctacaa atttagaaca atgtagtgaa ccacaaactc ctctcttcag cctgtgtgct    2460
tacttgtagt agttgtctga tctctaaaat ttagaactga atatgccaag aaagagttca    2520
atttcagaga ggagggtatg gtttcatttt aagtataaaa gcttccttta aaaaaaatta    2580
cgtcttacat tttgttatgc tcctaagtgt aattgatcct ggaaagtaag cgcaaggcta    2640
ctctctaatg ctaactctta tgtatgtaag aggtgaggaa ggagaggttg tgtgtggtgc    2700
atttgttttg taaaagcatc taactgtttt ctttccagac acttttttcaa aaatggcaat    2760 ggtatcagaa ttcctcaagc aggcctggtt tattgaaaat gaagagcagg aatatgttca    2820
aactgtgaag tcatccaaag gtggtcccgg atcagcggtg agcccctatc ctaccttcaa    2880
tccatcctcg gatgtcgctg ccttgcataa ggccataatg gttaaaggtg tggatgaagc    2940
aaccatcatt gacattctaa ctaagcgaaa caatgcacag cgtcaacaga tcaaagcagc    3000
atatctccag gaaacaggaa agcccctgga tgaaacactg aagaaagccc ttacaggtca    3060
ccttgaggag gttgttttag ctctgctaaa aactccagcg caatttgatg ctgatgaact    3120
tcgtgctgcc atgaagggcc ttggaactga tgaagatact ctaattgaga ttttggcatc    3180
aagaactaac aaagaaatca gagacattaa cagggtctac agagaggaac tgaagagaga    3240
tctggccaaa gacataacct cagacacatc tggagatttt cggaacgctt tgctttctct    3300
tgctaagggt gaccgatctg aggactttgg tgtgaatgaa gacttggctg attcagatgc    3360
cagggccttg tatgaagcag gagaaaggag aaagggaca gacgtaaacg tgttcaatac    3420
catccttacc accagaagct atccacaact tcgcagagtg tttcagaaat acaccaagta    3480
cagtaagcat gacatgaaca aagttctgga cctggagttg aaaggtgaca ttgagaaatg    3540
cctcacagct atcgtgaagt gcgccacaag caaaccagct ttctttgcag agaagcttca    3600
```

| | |
|---|---|
| tcaagccatg aaaggtgttg gaactcgcca taaggcattg atcaggatta tggtttcccg | 3660 |
| ttctgaaatt gacatgaatg atatcaaagc attctatcag aagatgtatg gtatctccct | 3720 |
| ttgccaagcc atcctggatg aaaccaaagg agattatgag aaaatcctgg tggctctttg | 3780 |
| tggaggaaac taaacattcc cttgatggtc tcaagctatg atcagaagac tttaattata | 3840 |
| tattttcatc ctataagctt aaataggaaa gtttcttcaa caggattaca gtgtagctac | 3900 |
| ctacatgctg aaaaatatag cctttaaatc attttatat tataactctg tataatagag | 3960 |
| ataagtccat ttttaaaaa tgttttcccc aaaccataaa accctataca agttgttcta | 4020 |
| gtaacaatac atgagaaaga tgtctatgta gctgaaaata aaatgacgtc acaagacaa | 4079 |

<210> SEQ ID NO 29
<211> LENGTH: 1669
<212> TYPE: DNA
<213> ORGANISM: Homo sapiens

<400> SEQUENCE: 29

| | |
|---|---|
| actttgtttt tggacatagc tgagccatgt acttcaaaca gaaggcagcc aattactaac | 60 |
| ttctggttgc taggtgtggc ttcctttaaa atcctataaa atcagaagcc caagtctcca | 120 |
| ctgccagtgt gaaatcttca gagaagaatt tctctttagt tctttgcaag aaggtagaga | 180 |
| taaagggaag gtgtgggaag gacttgtgaa atacatattc gaggaaaaac tatgcacaag | 240 |
| gccgtgcatt taaaaataaa ctccctaagg ctggggtgaa acctgctacg gtctgcgcaa | 300 |
| gttgactgtt aatgaatttg attctcagac acttttcaa aaatggcaat ggtatcagaa | 360 |
| ttcctcaagc aggcctggtt tattgaaaat gaagagcagg aatatgttca aactgtgaag | 420 |
| tcatccaaag gtggtcccgg atcagcggtg agccctatc ctaccttcaa tccatcctcg | 480 |
| gatgtcgctg ccttgcataa ggccataatg gttaaggtg tggatgaagc aaccatcatt | 540 |
| gacattctaa ctaagcgaaa caatgcacag cgtcaacaga tcaaagcagc atatctccag | 600 |
| gaaacaggaa agcccctgga tgaaacactg aagaaagccc ttacaggtca ccttgaggag | 660 |
| gttgttttag ctctgctaaa aactccagcg caatttgatg ctgatgaact tcgtgctgcc | 720 |
| atgaagggcc ttgaactga tgaagatact ctaattgaga ttttggcatc aagaactaac | 780 |
| aaagaaatca gagacattaa cagggtctac agagaggaac tgaagagaga tctggccaaa | 840 |
| gacataaccct cagacacatc tggagatttt cggaacgctt tgctttctct tgctaagggt | 900 |
| gaccgatctg aggactttgg tgtgaatgaa gacttggctg attcagatgc cagggccttg | 960 |
| tatgaagcag gagaaaggag aaaggggaca gacgtaaacg tgttcaatac catccttacc | 1020 |
| accagaagct atccacaact tcgcagagtg tttcagaaat acaccaagta cagtaagcat | 1080 |
| gacatgaaca aagttctgga cctggagttg aaaggtgaca ttgagaaatg cctcacagct | 1140 |
| atcgtgaagt gcgccacaag caaaccagct ttctttgcag agaagcttca tcaagccatg | 1200 |
| aaaggtgttg gaactcgcca taaggcattg atcaggatta tggtttcccg ttctgaaatt | 1260 |
| gacatgaatg atatcaaagc attctatcag aagatgtatg gtatctccct ttgccaagcc | 1320 |
| atcctggatg aaaccaaagg agattatgag aaaatcctgg tggctctttg tggaggaaac | 1380 |
| taaacattcc cttgatggtc tcaagctatg atcagaagac tttaattata tattttcatc | 1440 |
| ctataagctt aaataggaaa gtttcttcaa caggattaca gtgtagctac ctacatgctg | 1500 |
| aaaaatatag cctttaaatc attttatat tataactctg tataatagag ataagtccat | 1560 |
| ttttaaaaa tgttttcccc aaaccataaa accctataca agttgttcta gtaacaatac | 1620 |

```
atgagaaaga tgtctatgta gctgaaaata aaatgacgtc acaagacaa          1669
```

<210> SEQ ID NO 30
<211> LENGTH: 1671
<212> TYPE: DNA
<213> ORGANISM: Homo sapiens

<400> SEQUENCE: 30

```
actttgtttt tggacatagc tgagccatgt acttcaaaca gaaggcagcc aattactaac    60
ttctggttgc taggtgtggc ttcctttaaa atcctataaa atcagaagcc caagtctcca   120
ctgccagtgt gaaatcttca gagaagaatt tctctttagt tctttgcaag aaggtagaga   180
taaagggaag gtgtgggaag gacttgtgaa atacatattc gaggaaaaac tatgcacaag   240
gccgtgcatt taaaaataaa ctccctaagg ctggggtgaa acctgctacg gtctgcgcaa   300
gttgactgtt aatgaatttg attctcaggt cacttttttc aaaaatggca atggtatcag   360
aattcctcaa gcaggcctgg tttattgaaa atgaagagca ggaatatgtt caaactgtga   420
agtcatccaa aggtggtccc ggatcagcgg tgagccccta tcctaccttc aatccatcct   480
cggatgtcgc tgccttgcat aaggccataa tggttaaagg tgtggatgaa gcaaccatca   540
ttgacattct aactaagcga acaatgcac agcgtcaaca gatcaaagca gcatatctcc    600
aggaaacagg aaagcccctg gatgaaacac tgaagaaagc ccttacaggt caccttgagg   660
aggttgtttt agctctgcta aaaactccag cgcaatttga tgctgatgaa cttcgtgctg   720
ccatgaaggg ccttggaact gatgaagata ctctaattga gattttggca tcaagaacta   780
acaaagaaat cagagacatt aacagggtct acagagagga actgaagaga gatctggcca   840
aagcataaac ctcagacaca tctggagatt ttcggaacgc tttgctttct cttgctaagg   900
gtgaccgatc tgaggacttt ggtgtgaatg aagacttggc tgattcagat gccagggcct   960
tgtatgaagc aggagaaagg agaaagggga cagacgtaaa cgtgttcaat accatcctta  1020
ccaccagaag ctatccacaa cttcgcagag tgtttcagaa atacaccaag tacagtaagc  1080
atgacatgaa caaagttctg gacctggagt tgaaaggtga cattgagaaa tgcctcacag  1140
ctatcgtgaa gtgcgccaca agcaaaccag ctttctttgc agagaagctt catcaagcca  1200
tgaaaggtgt tggaactcgc cataaggcat tgatcaggat tatggtttcc cgttctgaaa  1260
ttgacatgaa tgatatcaaa gcattctatc agaagatgta tggtatctcc ctttgccaag  1320
ccatcctgga tgaaaccaaa ggagattatg agaaaatcct ggtggctctt tgtgggaaa   1380
actaaacatt cccttgatgg tctcaagcta tgatcagaag actttaatta tatattttca  1440
tcctataagc ttaaatagga aagtttcttc aacaggatta cagtgtagct acctacatgc  1500
tgaaaaatat agccttaaa tcattttat attataactc tgtataatag agataagtcc     1560
attttttaaa aatgttttcc ccaaaccata aaccctata caagttgttc tagtaacaat   1620
acatgagaaa gatgtctatg tagctgaaaa taaaatgacg tcacaagaca a            1671
```

<210> SEQ ID NO 31
<211> LENGTH: 1204
<212> TYPE: DNA
<213> ORGANISM: Homo sapiens

<400> SEQUENCE: 31

```
gttccgcaga tgcagaggtt gaggtggctg cgggactgga agtcatcggg cagaggtctc    60
acagcagcca aggaacctgg ggcccgctcc tcccccctcc aggccatgag gattctgcag   120
ttaatcctgc ttgctctggc aacagggctt gtaggggag agaccaggat catcaagggg   180
```

```
ttcgagtgca agcctcactc ccagccctgg caggcagccc tgttcgagaa gacgcggcta      240
ctctgtgggg cgacgctcat cgcccccaga tggctcctga cagcagccca ctgcctcaag      300
ccccgctaca tagttcacct ggggcagcac aacctccaga aggaggaggg ctgtgagcag      360
acccggacag ccactgagtc cttcccccac cccggcttca acaacagcct ccccaacaaa      420
gaccaccgca atgacatcat gctggtgaag atggcatcgc cagtctccat cacctgggct      480
gtgcgacccc tcaccctctc ctcacgctgt gtcactgctg gcaccagctg cctcatttcc      540
ggctgggca gcacgtccag ccccagtta cgcctgcctc acaccttgcg atgcgccaac      600
atcaccatca ttgagcacca gaagtgtgag aacgcctacc ccggcaacat cacagacacc      660
atggtgtgtg ccagcgtgca ggaaggggc aaggactcct gccagggtga ctccgggggc      720
cctctggtct gtaaccagtc tcttcaaggc attatctcct ggggccagga tccgtgtgcg      780
atcacccgaa agcctggtgt ctacacgaaa gtctgcaaat atgtggactg gatccaggag      840
acgatgaaga acaattagac tggacccacc caccacagcc catcaccctc catttccact      900
tggtgtttgg ttcctgttca ctctgttaat aagaaaccct aagccaagac cctctacgaa      960
cattctttgg gcctcctgga ctacaggaga tgctgtcact taataatcaa cctggggttc     1020
gaaatcagtg agacctggat tcaaattctg ccttgaaata ttgtgactct gggaatgaca     1080
acacctggtt tgttctctgt tgtatcccca gccccaaaga cagctcctgg ccatatatca     1140
aggtttcaat aaatatttgc taaatgaaaa aaaaaaaaa aaaaaaaaa aaaaaaaaa      1200
aaaa                                                                  1204

<210> SEQ ID NO 32
<211> LENGTH: 2246
<212> TYPE: DNA
<213> ORGANISM: Homo sapiens

<400> SEQUENCE: 32
aaagtccggg ggagccggtc ccgggcagcc gctcagcccc ctgcccctcg ccgcccgccg       60
cctgcctggg ccgggccgag gatgcggcgc agcgcctcgg cggccaggct tgctcccctc      120
cggcacgcct gctaacttcc cccgctacgt ccccgttcgc ccgccgggcc gccccgtctc      180
cccgcgccct ccgggtcggg tcctccagga gcgccaggcg ctgccgccgt gtgccctccg      240
ccgctcgccc gcgcgcccgc gctccccgcc tgcgcccagc gccccgcgcc cgcgcccagt      300
cctcgggcgg tcatgctgcc cctctgcctc gtgccgccc tgctgctggc cgccgggccc      360
gggccgagcc tgggcgacga agccatccac tgcccgccct gctccgagga aagctggcg      420
cgctgccgcc ccccgtggg ctgcgaggag ctggtgcgag agccgggctg cggctgttgc      480
gccacttgcg ccctgggctt ggggatgccc tgcggggtgt acacccccg ttgcggctcg      540
ggcctgcgct gctaccccgcc ccgagggggtg gagaagcccc tgcacacact gatgcacggg      600
caaggcgtgt gcatggagct ggcggagatc gaggccatcc aggaaagcct gcagccctct      660
gacaaggacg agggtgacca ccccaacaac agcttcagcc cctgtagcgc ccatgaccgc      720
aggtgcctgc agaagcactt cgccaaaatt cgagaccgga gcaccagtgg gggcaagatg      780
aaggtcaatg gggcgccccg ggaggatgcc cggcctgtgc cccagggctc ctgccagagc      840
gagctgcacc gggcgctgga gcggctggcc gcttcacaga gccgcaccca cgaggacctc      900
tacatcatcc ccatccccaa ctgcgaccgc aacggcaact tccacccccaa gcagtgtcac      960
ccagctctgg atgggcagcg tggcaagtgc tggtgtgtgg accggaagac gggggtgaag     1020
```

| | |
|---|---|
| cttccggggg gcctggagcc aaagggggag ctggactgcc accagctggc tgacagcttt | 1080 |
| cgagagtgag gcctgccagc aggccaggga ctcagcgtcc cctgctactc ctgtgctctg | 1140 |
| gaggctgcag agctgaccca gagtggagtc tgagtctgag tcctgtctct gcctgcggcc | 1200 |
| cagaagtttc cctcaaatgc gcgtgtgcac gtgtgcgtgt gcgtgcgtgt gtgtgtgttt | 1260 |
| gtgagcatgg gtgtgccctt ggggtaagcc agagcctggg gtgttctctt tggtgttaca | 1320 |
| cagcccaaga ggactgagac tggcacttag cccaagaggt ctgagccctg gtgtgtttcc | 1380 |
| agatcgatcc tggattcact cactcactca ttccttcact catccagcca cctaaaaaca | 1440 |
| tttactgacc atgtactacg tgccagctct agttttcagc cttgggaggt tttattctga | 1500 |
| cttcctctga ttttggcatg tggagacact cctataagga gagttcaagc ctgtgggagt | 1560 |
| agaaaaatct cattcccaga gtcagaggag aagagacatg taccttgacc atcgtccttc | 1620 |
| ctctcaagct agccagaggg tgggagccta aggaagcgtg gggtagcaga tggagtaatg | 1680 |
| gtcacgaggt ccagacccac tcccaaagct cagacttgcc aggctccctt tctcttcttc | 1740 |
| cccaggtcct tcctttaggt ctggttgttg caccatctgc ttggttggct ggcagctgag | 1800 |
| agccctgctg tgggagagcg aagggggtca aggaagact tgaagcacag agggctaggg | 1860 |
| aggtggggta catttctctg agcagtcagg gtgggaagaa agaatgcaag agtggactga | 1920 |
| atgtgcctaa tggagaagac ccacgtgcta ggggatgagg ggcttcctgg gtcctgttcc | 1980 |
| ctaccccatt tgtggtcaca gccatgaagt caccgggatg aacctatcct tccagtggct | 2040 |
| cgctccctgt agctctgcct ccctctccat atctccttcc cctacacctc cctccccaca | 2100 |
| cctccctact cccctgggca tcttctggct tgactggatg gaaggagact taggaaccta | 2160 |
| ccagttggcc atgatgtctt ttcttctttt tcttttttt aacaaaacag aacaaaacca | 2220 |
| aaaaatgtcc agatgaaaaa aaaaaa | 2246 |

<210> SEQ ID NO 33
<211> LENGTH: 4576
<212> TYPE: DNA
<213> ORGANISM: Homo sapiens

<400> SEQUENCE: 33

| | |
|---|---|
| ggccctcgcc gcccgcggcg ccccgagcgc tttgtgagca gatgcggagc cgagtggagg | 60 |
| gcgcgagcca gatgcgggc gacagctgac ttgctgagag gaggcgggga ggcgcggagc | 120 |
| gcgcgtgtgg tccttgcgcc gctgacttct ccactggttc ctgggcaccg aaagataaac | 180 |
| ctctcataat gaaggccccc gctgtgcttg cacctggcat cctcgtgctc ctgtttacct | 240 |
| tggtgcagag gagcaatggg gagtgtaaag aggcactagc aaagtccgag atgaatgtga | 300 |
| atatgaagta tcagcttccc aacttcaccg cggaaacacc catccagaat gtcattctac | 360 |
| atgagcatca cattttcctt ggtgccacta actacattta tgttttaaat gaggaagacc | 420 |
| ttcagaaggt tgctgagtac aagactgggc ctgtgctgga cacccagat gtttcccat | 480 |
| gtcaggactg cagcagcaaa gccaatttat caggaggtgt tggaaagat aacatcaaca | 540 |
| tggctctagt tgtcgacacc tactatgatg atcaactcat tagctgtggc agcgtcaaca | 600 |
| gagggacctg ccagcgacat gtctttcccc acaatcatac tgctgacata cagtcggagg | 660 |
| ttcactgcat attctcccca cagatagaag agcccagcca gtgtcctgac tgtgtggtga | 720 |
| gcgcctggg agccaaagtc ctttcatctg taaggaccg gttcatcaac ttctttgtag | 780 |
| gcaataccat aaaattcttct tatttcccag atcatccatt gcattcgata tcagtgagaa | 840 |
| ggctaaagga aacgaaagat ggttttatgt ttttgacgga ccagtcctac attgatgttt | 900 |

-continued

```
tacctgagtt cagagattct taccccatta agtatgtcca tgcctttgaa agcaacaatt      960
ttatttactt cttgacggtc caaagggaaa ctctagatgc tcagactttt cacacaagaa     1020
taatcaggtt ctgttccata aactctggat tgcattccta catggaaatg cctctggagt     1080
gtattctcac agaaaagaga aaaagagat ccacaaagaa ggaagtgttt aatatacttc      1140
aggctgcgta tgtcagcaag cctggggccc agcttgctag acaaatagga gccagcctga    1200
atgatgacat tcttttcggg gtgttcgcac aaagcaagcc agattctgcc gaaccaatgg    1260
atcgatctgc catgtgtgca ttccctatca aatatgtcaa cgacttcttc aacaagatcg    1320
tcaacaaaaa caatgtgaga tgtctccagc atttttacgg acccaatcat gagcactgct    1380
ttaataggac acttctgaga aattcatcag gctgtgaagc gcgccgtgat gaatatcgaa    1440
cagagtttac cacagctttg cagcgcgttg acttattcat gggtcaattc agcgaagtcc    1500
tcttaacatc tatatccacc ttcattaaag gagacctcac catagctaat cttgggacat    1560
cagagggtcg cttcatgcag gttgtggttt ctcgatcagg accatcaacc cctcatgtga    1620
attttctcct ggactcccat ccagtgtctc cagaagtgat tgtggagcat acattaaacc    1680
aaaatggcta cacactggtt atcactggga agaagatcac gaagatccca ttgaatggct    1740
tgggctgcag acatttccag tcctgcagtc aatgcctctc tgccccaccc tttgttcagt    1800
gtggctggtg ccacgacaaa tgtgtgcgat cggaggaatg cctgagcggg acatggactc    1860
aacagatctg tctgcctgca atctacaagg ttttcccaaa tagtgcaccc cttgaaggag    1920
ggacaaggct gaccatatgt ggctgggact ttggatttcg gaggaataat aaatttgatt    1980
taaagaaaac tagagttctc cttggaaatg agagctgcac cttgacttta agtgagagca    2040
cgatgaatac attgaaatgc acagttggtc ctgccatgaa taagcatttc aatatgtcca    2100
taattatttc aaatggccac gggacaacac aatacagtac attctcctat gtggatcctg    2160
taataacaag tatttcgccg aaatacggtc ctatggctgg tggcacttta cttactttaa    2220
ctggaaatta cctaaacagt gggaattcta gacacatttc aattggtgga aaaacatgta    2280
cttttaaaag tgtgtcaaac agtattcttg aatgttatac cccagcccaa accatttcaa    2340
ctgagtttgc tgttaaattg aaaattgact tagccaaccg agagacaagc atcttcagtt    2400
accgtgaaga tcccattgtc tatgaaattc atccaaccaa atcttttatt agtggtggga    2460
gcacaataac aggtgttggg aaaaacctga attcagttag tgtcccgaga atggtcataa    2520
atgtgcatga agcaggaagg aactttacag tggcatgtca acatcgctct aattcagaga    2580
taatctgttg taccactcct tccctgcaac agctgaatct gcaactcccc ctgaaaacca    2640
aagccttttt catgttagat gggatccttt ccaaatactt tgatctcatt tatgtacata    2700
atcctgtgtt taagcctttt gaaaagccag tgatgatctc aatgggcaat gaaaatgtac    2760
tggaaattaa gggaaatgat attgaccctg aagcagttaa aggtgaagtg ttaaaagttg    2820
gaaataagag ctgtgagaat atacacttac attctgaagc cgttttatgc acggtcccca    2880
atgacctgct gaaattgaac agcgagctaa atatagagtg gaagcaagca atttcttcaa    2940
ccgtccttgg aaaagtaata gttcaaccag atcagaattt cacaggattg attgctggtg    3000
ttgtctcaat atcaacagca ctgttattac tacttgggtt tttcctgtgg ctgaaaagaa    3060
gaaagcaaat taaagatctg ggcagtgaat tagttcgcta cgatgcaaga gtacacactc    3120
ctcatttgga taggcttgta agtgcccgaa gtgtaagccc aactacagaa atggttttcaa    3180
atgaatctgt agactaccga gctactttc cagaagatca gtttcctaat tcatctcaga    3240
```

```
acggttcatg ccgacaagtg cagtatcctc tgacagacat gtcccccatc ctaactagtg    3300
gggactctga tatatccagt ccattactgc aaaatactgt ccacattgac ctcagtgctc    3360
taaatccaga gctggtccag gcagtgcagc atgtagtgat tgggcccagt agcctgattg    3420
tgcatttcaa tgaagtcata ggaagagggc attttggttg tgtatatcat gggactttgt    3480
tggacaatga tggcaagaaa attcactgtg ctgtgaaatc cttgaacaga atcactgaca    3540
taggagaagt ttcccaattt ctgaccgagg aatcatcat gaaagatttt agtcatccca     3600
atgtcctctc gctcctggga atctgcctgc gaagtgaagg gtctccgctg gtggtcctac    3660
catacatgaa acatggagat cttcgaaatt tcattcgaaa tgagactcat aatccaactg    3720
taaaagatct tattggcttt ggtcttcaag tagccaaagg catgaaatat cttgcaagca    3780
aaaagtttgt ccacagagac ttggctgcaa gaaactgtat gctggatgaa aaattcacag    3840
tcaaggttgc tgattttggt cttgccagag acatgtatga taaagaatac tatagtgtac    3900
acaacaaaac aggtgcaaag ctgccagtga agtggatggc tttggaaagt ctgcaaactc    3960
aaaagtttac caccaagtca gatgtgtggt cctttggcgt gctcctctgg gagctgatga    4020
caagaggagc cccaccttat cctgacgtaa acacctttga tataactgtt tacttgttgc    4080
aagggagaag actcctacaa cccgaatact gcccagaccc cttatatgaa gtaatgctaa    4140
aatgctggca ccctaaagcc gaaatgcgcc catccttttc tgaactggtg tcccggatat    4200
cagcaatctt ctctactttc attggggagc actatgtcca tgtgaacgct acttatgtga    4260
acgtaaaatg tgtcgctcca tatccttctc tgttgtcatc agaagataac gctgatgatg    4320
aggtggacac acgaccagcc tccttctggg agacatcata gtgctagtac tatgtcaaag    4380
caacagtcca cactttgtcc aatggttttt tcactgcctg acctttaaaa ggccatcgat    4440
attctttgct acttgtatat acattcttga gaacactgca atgtgaaaat cacgtttgct    4500
atttataaac ttgtccttag attaatgtgt ctggacagat tgtgggagta agtgattctt    4560
ctaagaatta gatact                                                   4576

<210> SEQ ID NO 34
<211> LENGTH: 720
<212> TYPE: DNA
<213> ORGANISM: Homo sapiens

<400> SEQUENCE: 34
atgacccccc acaggctgct gccaccgctg ctgctgctgc tagctctgct gctcgctgcc     60
agcccaggag gcgccttggc gcggtgccca ggctgcgggc aaggggtgca ggcgggttgt    120
ccagggggct gcgtggagga ggaggatggg gggtcgccag ccgagggctg cgcggaagct    180
gagggctgtc tcaggaggga ggggcaggag tgcgggtct acaccctaa ctgcgcccca     240 ggactgcagt gccatccgcc caaggacgac gaggcgcctt gcgggcgct gctgctcggc    300 cgaggccgct gccttccggc ccgcgcgcct gctgttgcag aggagaatcc taaggagagt    360
aaaccccaag caggcactgc ccgcccacag gatgtgaacc gcagagacca acagaggaat    420
ccaggcacct ctaccacgcc ctcccagccc aattctgcgg gtgtccaaga cactgagatg    480
ggcccatgcc gtagacatct ggactcagtg ctgcagcaac tccagactga ggtctaccga    540
ggggctcaaa cactctacgt gcccaattgt gaccatcgag gcttctaccg gaagcggcag    600
tgccgctcct cccaggggca gcgccgaggt ccctgctggt gtgtggatcg gatgggcaag    660
tccctgccag ggtctccaga tggcaatgga agctcctcct gccccactgg gagtagcggc    720
```

<210> SEQ ID NO 35
<211> LENGTH: 1933
<212> TYPE: DNA
<213> ORGANISM: Homo sapiens

<400> SEQUENCE: 35

| | | | | | |
|---|---|---|---|---|---|
| cggtataaag | gcagccgcgg | tggcggtggc | ggcgcagagc | tctgtgctcc | ctgcagtcag | 60 |
| gactctggga | ccgcagggg | ctcccggacc | ctgactctgc | agccgaaccg | gcacggtttc | 120 |
| gtggggaccc | aggcttgcaa | agtgacggtc | attttctctt | tctttctccc | tcttgagtcc | 180 |
| ttctgagatg | atggctctgg | gcgcagcggg | agctacccgg | gtctttgtcg | cgatggtagc | 240 |
| ggcggctctc | ggcggccacc | ctctgctggg | agtgagcgcc | accttgaact | cggttctcaa | 300 |
| ttccaacgct | atcaagaacc | tgccccacc | gctgggcggc | gctgcgggc | acccaggctc | 360 |
| tgcagtcagc | gccgcgccgg | gaatcctgta | cccggcggg | aataagtacc | agaccattga | 420 |
| caactaccag | ccgtacccgt | gcgcagagga | cgaggagtgc | ggcactgatg | agtactgcgc | 480 |
| tagtcccacc | cgcggagggg | acgcgggcgt | gcaaatctgt | ctcgcctgca | ggaagcgccg | 540 |
| aaaacgctgc | atgcgtcacg | ctatgtgctg | ccccgggaat | tactgcaaaa | atggaatatg | 600 |
| tgtgtcttct | gatcaaaatc | atttccgagg | agaaattgag | gaaaccatca | ctgaaagctt | 660 |
| tggtaatgat | catagcacct | tggatgggta | ttccagaaga | accaccttgt | cttcaaaaat | 720 |
| gtatcacacc | aaaggacaag | aaggttctgt | ttgtctccgg | tcatcagact | gtgcctcagg | 780 |
| attgtgttgt | gctagacact | tctggtccaa | gatctgtaaa | cctgtcctga | agaaggtca | 840 |
| agtgtgtacc | aagcatagga | gaaaaggctc | tcatggacta | gaaatattcc | agcgttgtta | 900 |
| ctgtggagaa | ggtctgtctt | gccggataca | gaaagatcac | catcaagcca | gtaattcttc | 960 |
| taggcttcac | acttgtcaga | gacactaaac | cagctatcca | aatgcagtga | actcctttta | 1020 |
| tataatagat | gctatgaaaa | cctttatga | ccttcatcaa | ctcaatccta | aggatataca | 1080 |
| agttctgtgg | tttcagttaa | gcattccaat | aacaccttcc | aaaaacctgg | agtgtaagag | 1140 |
| ctttgtttct | ttatggaact | cccctgtgat | tgcagtaaat | tactgtattg | taaattctca | 1200 |
| gtgtggcact | tacctgtaaa | tgcaatgaaa | cttttaatta | tttttctaaa | ggtgctgcac | 1260 |
| tgcctatttt | tcctcttgtt | atgtaaattt | ttgtacacat | tgattgttat | cttgactgac | 1320 |
| aaatattcta | tattgaactg | aagtaaatca | tttcagctta | tagttcttaa | aagcataacc | 1380 |
| ctttacccca | tttaattcta | gagtctagaa | cgcaaggatc | tcttggaatg | acaaatgata | 1440 |
| ggtacctaaa | atgtaacatg | aaaatactag | cttattttct | gaaatgtact | atcttaatgc | 1500 |
| ttaaattata | tttcccttta | ggctgtgata | gttttttgaaa | taaaatttaa | catttaatat | 1560 |
| catgaaatgt | tataagtaga | catacatttt | gggattgtga | tcttagaggt | ttgtgtgtgt | 1620 |
| gtacgtatgt | gtgtgttcta | caagaacgga | agtgtgatat | gtttaaagat | gatcagagaa | 1680 |
| aagacagtgt | ctaaatataa | gacaatattg | atcagctcta | gaataacttt | aaagaaagac | 1740 |
| gtgttctgca | ttgataaact | caaatgatca | tggcagaatg | agagtgaatc | ttacattact | 1800 |
| actttcaaaa | atagtttcca | ataaattaat | aatacctacc | taaatggtca | atattttcg | 1860 |
| gacaaggaag | aaaatcatcc | acaaaaataa | tactccaaag | tacttggtga | ttggcaggaa | 1920 |
| caggatgtgt | gcc | | | | | 1933 |

<210> SEQ ID NO 36
<211> LENGTH: 5191
<212> TYPE: DNA
<213> ORGANISM: Homo sapiens

<400> SEQUENCE: 36

```
ggcgagtgcg tcgagctcgc cgcggactca agatggcggc gtgtggacgt gtacggagga        60
tgttccgctt gtcggcggcg ctgcatctgc tgctgctatt cgcggccggg gccgagaaac       120
tccccggcca gggcgtccac agccagggcc agggtcccgg ggccaacttt gtgtccttcg       180
tagggcaggc cggaggcggc ggcccggcgg gtcagcagct gccccagctg cctcagtcat       240
cgcagcttca gcagcaacag cagcagcagc aacagcaaca gcagcctcag ccgccgcagc       300
cgcctttccc ggcgggtggg cctccggccc ggcggggagg agcgggggct ggtgggggct       360
ggaagctggc ggaggaagag tcctgcaggg aggacgtgac ccgcgtgtgc cctaagcaca       420
cctggagcaa caacctggcg gtgctcgagt gcctgcagga tgtgagggag cctgaaaatg       480
aaatttcttc agactgcaat catttgttgt ggaattataa gctgaaccta actacagatc       540
ccaaatttga atctgtggcc agagaggttt gcaaatctac tataacagag attaaagaat       600
gtgctgatga accggttgga aaaggttaca tggtttcctg cttggtggat caccgaggca       660
acatcactga gtatcagtgt caccagtaca ttaccaagat gacggccatc attttttagtg      720
attaccgttt aatctgtggc ttcatggatg actgcaaaaa tgacatcaac attctgaaat       780
gtggcagtat tcggcttgga gaaaaggatg cacattcaca aggtgaggtg gtatcatgct       840
tggagaaagg cctggtgaaa gaagcagaag aaagagaacc caagattcaa gtttctgaac       900
tctgcaagaa agccattctc cgggtggctg agctgtcatc ggatgacttt cacttagacc       960
ggcatttata ttttgcttgc cgagatgatc gggagcgttt ttgtgaaaat acacaagctg      1020
gtgagggcag agtgtataag tgcctcttta accataaatt tgaagaatcc atgagtgaaa      1080
agtgtcgaga agcacttaca acccgccaaa agctgattgc ccaggattat aaagtcagtt      1140
attcattggc caaatcctgt aaaagtgact tgaagaaata ccggtgcaat gtggaaaacc      1200
ttccgcgatc gcgtgaagcc aggctctcct acttgttaat gtgcctggag tcagctgtac      1260
acagagggcg acaagtcagc agtgagtgcc aggggagat gctggattac cgacgcatgt      1320
tgatggaaga cttttctctg agccctgaga tcatcctaag ctgtcggggg agattgaac       1380
accattgttc cggattacat cgaaaagggc ggaccctaca ctgtctgatg aaagtagttc      1440
gaggggagaa gggaaccctt ggaatgaact gccagcaggc gcttcaaaca ctgattcagg      1500
agactgaccc tggtgcagat taccgcattg atcgagcttt gaatgaagct tgtgaatctg      1560
taatccagac agcctgcaaa catataagat ctggagaccc aatgatcttg tcgtgcctga      1620
tggaacattt atacacagag aagatggtag aagactgtga acaccgtctc ttagagctgc      1680
agtatttcat ctcccgggat tggaagctgg accctgtcct gtaccgcaag tgccagggag      1740
acgcttctcg tctttgccac acccacggtt ggaatgagac cagtgaattt atgcctcagg      1800
gagctgtgtt ctcttgttta tacagacacg cctaccgcac tgaggaacag ggaaggaggc      1860
tctcacggga gtgccgagct gaagtccaaa ggatcctaca ccagcgtgcc atggatgtca      1920
agctggatcc tgccctccag gataagtgcc tgattgatct gggaaaatgg tgcagtgaga      1980
aaacagagac tggacaggag ctggagtgcc ttcaggacca tctggatgac ttggtggtgg      2040
agtgtagaga tatagttggc aacctcactg agttagaatc agaggatatt caaatagaag      2100
ccttgctgat gagagcctgt gagcccataa ttcagaactt ctgccacgat gtggcagata      2160
accagataga ctctggggac ctgatggagt gtctgataca gaacaaacac cagaaggaca      2220
tgaacgagaa gtgtgccatc ggagttaccc acttccagct ggtgcagatg aaggattttc      2280
ggttttctta caagtttaaa atggcctgca aggaggacgt gttgaagctt tgcccaaaca      2340
```

```
taaaaaagaa ggtggacgtg gtgatctgcc tgagcacgac cgtgcgcaat gacactctgc    2400
aggaagccaa ggagcacagg gtgtccctga agtgccgcag gcagctccgt gtggaggagc    2460
tggagatgac ggaggacatc cgcttggagc cagatctata cgaagcctgc aagagtgaca    2520
tcaaaaactt ctgttccgct gtgcaatatg gcaacgctca gattatcgaa tgtctgaaag    2580
aaaacaagaa gcagctaagc acccgctgcc accaaaaagt atttaagctg caggagacag    2640
agatgatgga cccagagcta gactacaccc tcatgagggt ctgcaagcag atgataaaga    2700
ggttctgtcc ggaagcagat tctaaaacca tgttgcagtg cttgaagcaa aataaaaaca    2760
gtgaattgat ggatcccaaa tgcaaacaga tgataaccaa gcgccagatc acccagaaca    2820
cagattaccg cttaaacccc atgttaagaa aagcctgtaa agctgacatt cctaaattct    2880
gtcacggtat cctgactaag gccaaggatg attcagaatt agaaggacaa gtcatctctt    2940
gcctgaagct gagatatgct gaccagcgcc tgtcttcaga ctgtgaagac cagatccgaa    3000
tcattatcca ggagtccgcc ctggactacc gcctggatcc tcagctccag ctgcactgct    3060
cagacgagat ctccagtcta tgtgctgaag aagcagcagc caagagcag acaggtcagg    3120 tggaggagtg cctcaaggtc aacctgctca agatcaaaac agaattgtgt aaaaaggaag    3180
tgctaaacat gctgaaggaa agcaaagcag acatctttgt tgacccggta cttcatactg    3240
cttgtgccct ggacattaaa caccactgcg cagccatcac ccctggccgc gggcgtcaaa    3300
tgtcctgtct catggaagca ctggaggata agcgggtgag gttacagccc gagtgcaaaa    3360
agcgcctcaa tgaccggatt gagatgtgga gttacgcaga aaaggtggcc ccagcagatg    3420
gcttctctga tcttgccatg caagtaatga cgtctccatc taagaactac attctctctg    3480
tgatcagtgg gagcatctgt atattgttcc tgattggcct gatgtgtgga cggatcacca    3540
agcgagtgac acgagagctc aaggacaggt agagccacct tgaccaccaa aggaactacc    3600
tatccagtgc ccagtttgta cagccctctt gtatagcatc cccactcacc tcgctcttct    3660
cagaagtgac accaaccccg tgttagagca ttagcagatg tccactgcgt tgtcccatcc    3720
agcctccact cgtgtccatg gtgtcctcct cctcctcacc gtgcagcagc agcagctggt    3780
cgctggggtt actgcctttg tttggcaaac ttgggtttac ctgcctgtag acaagtctct    3840
ctcataccaa cagaacttcc ggtacttcca gaaccaactc acctgacctg caactcaaag    3900
gcttttttaa gaaaccacc aaaaaaaaaa atttttttaa agaaaaaaat gtatatagta    3960
acgcatctcc tccaggcttg atttgggcaa tggggttatg tctttcatat gactgtgtaa    4020
aacaaagaca ggacttggag gggaagcaca ccacccagtg tgccatgact gaggtgtctc    4080
gttcatctct cagaagcacc ttggggcctc gccagggccg tggtcttcac cgaggcgtgg    4140
gtgggcagcc gttccccagg ctgtgtgggg tcctgctttc ttctgctgag acagtgacgc    4200
tttccagttt ccaccctaat cagccactgc tggtcacagc cccacagcca tgggtatttc    4260
tgtggtctcc tcgcttcatt gaagcaaagc atgagccttc ctagacaagg gcagctgggg    4320
aggggaaggg accggaagtt tgtgaagttg aacagtccat ccatctgcac tgagaggctg    4380
gatcctgagt cccggggcag caggatccca ggaaccttcc tcctccaggg cagcacagga    4440
ctcagccatg tctggaccgg ccctgctgag gctacagtca ctctgaagc tctgcgcttc    4500 atcaggaggc aggactgtgg cgggaggggt ccttgaagat gggtgtgggg agcagtgggt    4560
caggaagtgg gagccagagg tttgactcac tttgctttat ttttcaggct acaatacagg    4620
tcagagacaa tggcttataa aggtttagtg tggtctcagg atgtgacagg cagtccagcc    4680
```

-continued

```
tgacctttct gcacactcca gacaaacttc ccagacaagc tcctttgtgc ctctacgtgg    4740
agagggtgtg gaaagttatc acattaaaag atggaggatt tgctctgttt tttttctttc    4800
tgtccatttg ctgcgtgtac ccactctagt aggcattggc taaatgttgt attttggcga    4860
ttcatcaacc tttgcagaat atgggctttα tαgaagcaat attcttggcc atcccgcctc    4920
attcctccag tgtggagatg acaagtctgg gtgtgagagg gaggggtccg ggcatcatgg    4980
ttcagcgtgg cactcctttg gttgagtttg ggcatgaga tcacagtggc tgcacaagag    5040
agcagtgtgt acagtaggag agacatttat gtaatatata ttttattaac ctgttagatg    5100
tccacaaagt attataaatc acgtgcctaa aactgtccat gtagaccaag gcctgccctc    5160 ggcgccccc actcttgcct ctgctctgca c                                   5191
```

<210> SEQ ID NO 37
<211> LENGTH: 3901
<212> TYPE: DNA
<213> ORGANISM: Homo sapiens

<400> SEQUENCE: 37

```
aagatggcgg cgtgtggacg tgtacggagg atgttccgct tgtcggcggc gctgcatctg     60
ctgctgctat tcgcggccgg ggccgagaaa ctccccggcc atggcgtcca cagccagggc    120
cagggtcccg gggccaactt tgtgtccttc gtagggcagg ccggaggcgg cggcccggcg    180
ggtcagcagc tgccccagct gcttcagtca tcgcagcttc agcagcaaca gcagcagcag    240
caacagcaac agcagcttca gccgccgcag ccgccttttcc cggcgggtgg gcctccggcc    300
cggcggggag gagcgggggc tggtgggggc tggaagctgg cggaggaaga gtcctgcagg    360
gaggacgtga cccgcgtgtg ccctaagcac acctggagca acaacctggc ggtgctcgag    420
tgcctgcagg atgtgaggga gcctgaaaat gaaatttctt cagactgcaa tcatttgttg    480
tggaattata agctgaacct aactacagat cccaaatttg aatctgtggc cagagaggtt    540
tgcaaatcta ctataacaga gattaaagaa tgtgctgatg aaccggttgg aaaaggttac    600
atggtttcct gcttagtgga tcaccgaggc aacatcactg agtatcagtg tcaccagtac    660
attaccaaga tgacggccat cattttttagt gattaccgtt taatctgtgg cttcatggat    720
gactgcaaaa atgacatcaa cattctgaaa tgtggcagta ttcggcttgg agaaaaggat    780
gcacattcac aaggtgaggt ggtatcatgc ttggagaaag gcctggtgaa agaagcagaa    840
gaaagagaac ccaagattca agtttctgaa ctctgcaaga aagccattct ccgggtggct    900
gagctgtcat cggatgactt tcacttagac cggcatttat attttgcttg ccgagatgat    960
cgggagcgtt tttgtgaaaa tacacaagct ggtgagggca gagtgtataa gtgcctcttt   1020
aaccataaat ttgaagaatc catgagtgaa aagtgtcgag aagcacttac aaacccgcca   1080
aagctgattg cccaggatta taaagtcagt tattcattgg ccaaatcctg taaaagtgac   1140
ttgaagaaat accggtgcaa tgtggaaaac cttccgcgat cgcgtgaagc caggctctcc   1200
tacttgttaa tgtgcctgga gtcagctgta cacagagggc gacaagtcag cagtgagtgc   1260
caggggagga tgctggatta ccgacgcatg ttgatggaag acttttctct gagccctgag   1320
atcatcctaa gctgtcgggg ggagattgaa caccattgtt ccggattaca tcgaaaaggg   1380
cggaccctac actgtctgat gaaagtagtt cgaggggaga aggggaacct tggaatgaac   1440
tgccagcagg cgcttcaaac actgattcag gagactgacc ctggtgcaga ttaccgcatt   1500
gatcgagctt tgaatgaagc ttgtgaatct gtaatccaga cagcctgcaa acatataaga   1560
tctggagacc caatgatctt gtcgtgcctg atggaacatt tatacacaga agatggta    1620
```

```
gaagactgtg aacaccgtct cttagagctg cagtatttca tctcccggga ttggaagctg   1680
gaccctgtcc tgtaccgcaa gtgccaggga gacgcttctc gtctttgcca cacccacggt   1740
tggaatgaga ccagtgaatt tatgcctcag ggagctgtgt tctcttgttt atacagacac   1800
gcctaccgca ctgaggaaca gggaaggagg ctctcacggg agtgccgagc tgaagtccaa   1860
aggatcctac accagcgtgc catggatgtc aagctggatc ctgccctcca ggataagtgc   1920
ctgattgatc tgggaaaatg gtgcagtgag aaaacagaga ctggacagga gctggagtgc   1980
cttcaggacc atctggatga cttggtggtg gagtgtagag atatagttgg caacctcact   2040
gagttagaat cagaggatat tcaaatagaa gccttgctga tgagagcctg tgagcccata   2100
attcagaact tctgccacga tgtggcagat aaccagatag actctgggga cctgatggag   2160
tgtctgatac agaacaaaca ccagaaggac atgaacgaga agtgtgccat cggagttacc   2220
cacttccagc tggtgcagat gaaggatttt cggttttctt acaagtttaa aatggcctgc   2280
aaggaggacg tgttgaagct tgcccaaac ataaaaaga aggtggacgt ggtgatctgc   2340
ctgagcacga ccgtgcgcaa tgacactctg caggaagcca aggagcacag ggtgtccctg   2400
aagtgccgca ggcagctccg tgtggaggag ctggagatga cggaggacat ccgcttggag   2460
ccagatctat acgaagcctg caagagtgac atcaaaaact tctgttccgc tgtgcaatat   2520
ggcaacgctc agattatcga atgtctgaaa gaaaacaaga agcagctaag cacccgctgc   2580
caccaaaaag tatttaagct gcaggagaca gagatgatgg acccagagct agactacacc   2640
ctcatgaggg tctgcaagca gatgataaag aggttctgtc cggaagcaga ttctaaaacc   2700
atgttgcagt gcttgaagca aaataaaaac agtgaattga tggatcccaa atgcaaacag   2760
atgataacca agcgccagat cacccagaac acagattacc gcttaaaccc catgttaaga   2820
aaagcctgta agctgacat tcctaaattc tgtcacggta tcctgactaa ggccaaggat   2880
gattcagaat tagaaggaca agtcatctct tgcctgaagc tgagatatgc tgaccagcgc   2940
ctgtcttcag actgtgaaga ccagatccga atcattatcc aggagtccgc cctggactac   3000
cgcctggatc ctcagctcca gctgcactgc tcagacgaga tctccagtct atgtgctgaa   3060
gaagcagcag cccaagagca gacaggtcag gtggaggagt gcctcaaggt caacctgctc   3120
aagatcaaaa cagaattgtg taaaaaggaa gtgctaaaca tgctgaagga agcaaagca   3180
gacatctttg ttgacccggt acttcatact gcttgtgccc tggacattaa acaccactgc   3240
gcagccatca cccctggccg cgggcgtcaa atgtcctgtc tcatggaagc actgaggat   3300
aagcgggtga ggttacagcc cgagtgcaaa aagcgcctca atgaccggat tgagatgtgg   3360
agttacgcag caaaggtggc cccagcagat ggcttctctg atcttgccat gcaagtaatg   3420
acgtctccat ctaagaacta cattctctct gtgatcagtg ggagcatctg tatattgttc   3480
ctgattggcc tgatgtgtgg acggatcacc aagcgagtga cacgagagct caaggacagg   3540
tagagccacc ttgaccacca aaggaactac ctatccagtg cccagtttgt acagccctct   3600
tgtatagcat ccccactcac ctcgctcttc tcagaagtga caccaacccc gtgttagagc   3660
attagcagat gtccactgcg ttgtcccatc cagcctccac tcgtgtccat ggtgtcctcc   3720
tcctcctcac cgtgcagcag cagcagctgg tcgctggggt tactgccttt gtttggcaaa   3780
cttgggttta cctgcctgta gacaagtctc tctcatacca acagaacttc cggtacttcc   3840
agaaccaact cacctgacct gcaactcaaa ggcttttta agaaaaccac caaaaaaaaa   3900
a                                                                    3901
```

<210> SEQ ID NO 38
<211> LENGTH: 5191
<212> TYPE: DNA
<213> ORGANISM: Homo sapiens

<400> SEQUENCE: 38

```
ggcgagtgcg tcgagctcgc cgcggactca agatggcggc gtgtggacgt gtacggagga      60
tgttccgctt gtcggcggcg ctgcatctgc tgctgctatt cgcggccggg gccgagaaac     120
tccccggcca gggcgtccac agccagggcc agggtcccgg ggccaacttt gtgtccttcg     180
tagggcaggc cggaggcggc ggcccggcgg gtcagcagct gccccagctg cctcagtcat     240
cgcagcttca gcagcaacag cagcagcagc aacagcaaca gcagcctcag ccgccgcagc     300
cgcctttccc ggcgggtggg cctccggccc ggcggggagg agcgggggct ggtgggggct     360
ggaagctggc ggaggaagag tcctgcaggg aggacgtgac ccgcgtgtgc cctaagcaca     420
cctggagcaa caacctggcg gtgctcgagt gcctgcagga tgtgagggag cctgaaaatg     480
aaatttcttc agactgcaat catttgttgt ggaattataa gctgaaccta actacagatc     540
ccaaatttga atctgtggcc agagaggttt gcaaatctac tataacagag attaaagaat     600
gtgctgatga accggttgga aaaggttaca tggtttcctg cttggtggat caccgaggca     660
acatcactga gtatcagtgt caccagtaca ttaccaagat gacggccatc atttttagtg     720
attaccgttt aatctgtggc ttcatggatg actgcaaaaa tgacatcaac attctgaaat     780
gtggcagtat tcggcttgga gaaaaggatg cacattcaca aggtgaggtg gtatcatgct     840
tggagaaagg cctggtgaaa gaagcagaag aaagagaacc caagattcaa gtttctgaac     900
tctgcaagaa agccattctc cgggtggctg agctgtcatc ggatgacttt cacttagacc     960
ggcatttata ttttgcttgc cgagatgatc gggagcgttt ttgtgaaaat acacaagctg    1020
gtgagggcag agtgtataag tgcctcttta accataaatt tgaagaatcc atgagtgaaa    1080
agtgtcgaga agcacttaca acccgccaaa agctgattgc ccaggattat aaagtcagtt    1140
attcattggc caaatcctgt aaaagtgact gaagaaata ccggtgcaat gtggaaaacc    1200
ttccgcgatc gcgtgaagcc aggctctcct acttgttaat gtgcctggag tcagctgtac    1260
acagagggcg acaagtcagc agtgagtgcc aggggagat gctggattac cgacgcatgt    1320
tgatggaaga cttttctctg agccctgaga tcatcctaag ctgtcggggg gagattgaac    1380
accattgttc cggattacat cgaaaagggc ggaccctaca ctgtctgatg aaagtagttc    1440
gagggagaa ggggaacctt ggaatgaact gccagcaggc gcttcaaaca ctgattcagg    1500
agactgaccc tggtgcagat taccgcattg atcgagcttt gaatgaagct tgtgaatctg    1560
taatccagac agcctgcaaa catataagat ctggagaccc aatgatcttg tcgtgcctga    1620
tggaacattt atacacagag aagatggtag aagactgtga acaccgtctc ttagagctgc    1680
agtatttcat ctcccgggat tggaagctgg accctgtcct gtaccgcaag tgccaggcag    1740
acgcttctcg tctttgccac acccacggtt ggaatgagac cagtgaattt atgcctcagg    1800
gagctgtgtt ctcttgttta tacagacacg cctaccgcac tgaggaacag ggaaggaggc    1860
tctcacggga gtgccgagct gaagtccaaa ggatcctaca ccagcgtgcc atggatgtca    1920
agctggatcc tgccctccag gataagtgcc tgattgatct gggaaaatgg tgcagtgaga    1980
aaacagagac tggacaggag ctggagtgcc tcaggacca tctggatgac ttggtggtgg    2040
agtgtagaga tatagttggc aacctcactg agttagaatc agaggatatt caaatagaag    2100
ccttgctgat gagagcctgt gagcccataa ttcagaactt ctgccacgat gtggcagata    2160
```

```
accagataga ctctggggac ctgatggagt gtctgataca gaacaaacac cagaaggaca    2220
tgaacgagaa gtgtgccatc ggagttaccc acttccagct ggtgcagatg aaggattttc    2280
ggttttctta caagtttaaa atggcctgca aggaggacgt gttgaagctt tgcccaaaca    2340
taaaaaagaa ggtggacgtg gtgatctgcc tgagcacgac cgtgcgcaat gacactctgc    2400
aggaagccaa ggagcacagg gtgtccctga agtgccgcag gcagctccgt gtggaggagc    2460
tggagatgac ggaggacatc cgcttggagc cagatctata cgaagcctgc aagagtgaca    2520
tcaaaaactt ctgttccgct gtgcaatatg gcaacgctca gattatcgaa tgtctgaaag    2580
aaaacaagaa gcagctaagc acccgctgcc accaaaaagt atttaagctg caggagacag    2640
agatgatgga cccagagcta gactacaccc tcatgagggt ctgcaagcag atgataaaga    2700
ggttctgtcc ggaagcagat tctaaaacca tgttgcagtg cttgaagcaa aataaaaaca    2760
gtgaattgat ggatcccaaa tgcaaacaga tgataaccaa cgccagatc acccagaaca    2820
cagattaccg cttaaacccc atgttaagaa aagcctgtaa agctgacatt cctaaattct    2880
gtcacggtat cctgactaag gccaaggatg attcagaatt agaaggacaa gtcatctctt    2940
gcctgaagct gagatatgct gaccagcgcc tgtcttcaga ctgtgaagac cagatccgaa    3000
tcattatcca ggagtccgcc ctggactacc gcctggatcc tcagctccag ctgcactgct    3060
cagacgagat ctccagtcta tgtgctgaag aagcagcagc ccaagagcag acaggtcagg    3120
tggaggagtg cctcaaggtc aacctgctca agatcaaaac agaattgtgt aaaaaggaag    3180
tgctaaacat gctgaaggaa agcaaagcag acatctttgt tgacccggta cttcatactg    3240
cttgtgccct ggacattaaa caccactgcg cagccatcac ccctggccgc gggcgtcaaa    3300
tgtcctgtct catggaagca ctggaggata gcgggtgag gttacagccc gagtgcaaaa    3360
agcgcctcaa tgaccggatt gagatgtgga gttacgcagc aaaggtggcc ccagcagatg    3420
gcttctctga tcttgccatg caagtaatga cgtctccatc taagaactac attctctctg    3480
tgatcagtgg gagcatctgt atattgttcc tgattggcct gatgtgtgga cggatcacca    3540
agcgagtgac acgagagctc aaggacaggt agagccacct tgaccaccaa aggaactacc    3600
tatccagtgc ccagtttgta cagccctctt gtatagcatc cccactcacc tcgctcttct    3660
cagaagtgac accaaccccg tgttagagca ttagcagatg tccactgcgt tgtcccatcc    3720
agcctccact cgtgtccatg gtgtcctcct cctcctcacc gtgcagcagc agcagctggt    3780
cgctggggtt actgcctttg tttggcaaac ttgggtttac ctgcctgtag acaagtctct    3840
ctcataccaa cagaacttcc ggtacttcca gaaccaactc acctgacctg caactcaaag    3900
gcttttttaa gaaaaccacc aaaaaaaaaa attttttttaa agaaaaaaat gtatatagta    3960
acgcatctcc tccaggcttg atttgggcaa tggggttatg tctttcatat gactgtgtaa    4020
aacaaagaca ggacttggag gggaagcaca ccacccagtg tgccatgact gaggtgtctc    4080
gttcatctct cagaagcacc ttggggcctc gccagggccg tggtcttcac cgaggcgtgg    4140
gtgggcagcc gttccccagg ctgtgtgggg tcctgctttc ttctgctgag acagtgacgc    4200
tttccagttt ccaccctaat cagccactgc tggtcacagc cccacagcca tgggtatttc    4260
tgtggtctcc tcgcttcatt gaagcaaagc atgagcctc ctagacaagg gcagctgggg    4320
aggggaaggg accggaagtt tgtgaagttg aacagtccat ccatctgcac tgagaggctg    4380
gatcctgagt cccggggcag caggatccca ggaaccttcc tcctccaggg cagcacagga    4440
ctcagccatg tctggaccgg ccctgctgag gctacagtca ctctgaaagc tctgcgcttc    4500
```

```
atcaggaggc aggactgtgg cgggaggggt ccttgaagat gggtgtgggg agcagtgggt      4560
caggaagtgg gagccagagg tttgactcac tttgctttat ttttcaggct acaatacagg      4620
tcagagacaa tggcttataa aggtttagtg tggtctcagg atgtgacagg cagtccagcc      4680
tgacctttct gcacactcca gacaaacttc ccagacaagc tcctttgtgc ctctacgtgg      4740
agagggtgtg gaaagttatc acattaaaag atggaggatt tgctctgttt ttttctttc       4800 tgtccatttg ctgcgtgtac ccactctagt aggcattggc taaatgttgt attttggcga      4860
ttcatcaacc tttgcagaat atgggcttta tagaagcaat attcttggcc atcccgcctc      4920
attcctccag tgtggagatg acaagtctgg gtgtgagagg gaggggtccg ggcatcatgg      4980
ttcagcgtgg cactcctttg gttgagtttg gggcatgaga tcacagtggc tgcacaagag      5040
agcagtgtgt acagtaggag agacatttat gtaatatata ttttattaac ctgttagatg      5100
tccacaaagt attataaatc acgtgcctaa aactgtccat gtagaccaag gcctgccctc      5160
ggcgcccccc actcttgcct ctgctctgca c                                     5191

<210> SEQ ID NO 39
<211> LENGTH: 989
<212> TYPE: DNA
<213> ORGANISM: Homo sapiens

<400> SEQUENCE: 39
gcgcagatgc catcaaaatg ggactctggt caccctgtca tttcccttct ggcagacact        60
aaaatgggga gccctgccct cagtggggtg tcccaagtgc catcagagga ggcttggtga       120
ctcccagaca aagggaagc tttagcgtct gccctcaggg tgaggtggag gtatcgcctc        180
cggcctcagg gaaccacagt ctgaggggga gatgcagccc ctgccttccc attcagagag       240
gggttttgtg aggtggcttg ggggcatagg gcagaagtgg atcctacagg ctgagctaag       300
gccccaagag cctcagcagt gtacccatca cctggcacct ctgcagccac agatccatga       360
tgtgcagttc cctggagcag gcgctggctg tgctggtcac taccttccac aagtactcct       420
gccaagaggg cgacaagttc aagctgagta aagggggaaat gaaggaactt ctgcacaagg       480
agctgcccag ctttgtgggg gagaaagtgg atgaggaggg gctgaagaag ctgatgggca       540
acctggatga aacagtgac cagcaggtgg acttccagga gtatgctgtt ttcctggcgc        600
tcatcactgt catgtgcaat gacttcttcc agggctgccc agaccgaccc tgaagcagaa       660
ctcttgactc cctgccatgg atctcttggg cccaggactc tcgatgcctt tgagttttgt      720
attcaataaa cttttttttgt ctgttgataa tattttaatt gctcagtgac gttccataac     780
ccgtctggct cagctggagt gctgggagat gagggcctcc tggatcctgc tcccttctgg      840
gctctgactc tcctggaaat ctctccaagg ccagagctat gctttaggtc tcaatttggg      900
aatttcaaac accagcaaaa aattggaaat cgagataggt tgctgacttt tattttgtca      960
aataaagata ttaaaaaagg caaatacca                                         989

<210> SEQ ID NO 40
<211> LENGTH: 12
<212> TYPE: PRT
<213> ORGANISM: Homo sapiens

<400> SEQUENCE: 40

Cys Ala Thr Ser Lys Pro Ala Phe Phe Ala Glu Lys
1               5                   10

<210> SEQ ID NO 41
```

-continued

```
<211> LENGTH: 21
<212> TYPE: PRT
<213> ORGANISM: Homo sapiens

<400> SEQUENCE: 41

Tyr Leu Cys Ala Ser Arg Pro Asp Gly Ser Ser Gly Asn Thr Ile Tyr
1               5                   10                  15

Phe Gly Glu Gly Ser
            20

<210> SEQ ID NO 42
<211> LENGTH: 12
<212> TYPE: PRT
<213> ORGANISM: Homo sapiens

<400> SEQUENCE: 42

Cys Ile Thr Pro Thr Gly Thr His Pro Leu Ala Lys
1               5                   10

<210> SEQ ID NO 43
<211> LENGTH: 10
<212> TYPE: PRT
<213> ORGANISM: Homo sapiens

<400> SEQUENCE: 43

Phe Thr Tyr Ala Gly Cys Leu Ser Val Lys
1               5                   10

<210> SEQ ID NO 44
<211> LENGTH: 12
<212> TYPE: PRT
<213> ORGANISM: Homo sapiens

<400> SEQUENCE: 44

Trp Leu Leu Thr Ala Ala His Cys Leu Lys Pro Arg
1               5                   10

<210> SEQ ID NO 45
<211> LENGTH: 14
<212> TYPE: PRT
<213> ORGANISM: Homo sapiens

<400> SEQUENCE: 45

Gly Glu Leu Asp Cys His Gln Leu Ala Asp Ser Phe Arg Glu
1               5                   10

<210> SEQ ID NO 46
<211> LENGTH: 22
<212> TYPE: PRT
<213> ORGANISM: Homo sapiens

<400> SEQUENCE: 46

Ser Cys Glu Asn Ile His Leu His Ser Glu Ala Val Leu Cys Thr Val
1               5                   10                  15

Pro Asn Asp Leu Leu Lys
            20

<210> SEQ ID NO 47
<211> LENGTH: 13
<212> TYPE: PRT
<213> ORGANISM: Homo sapiens

<400> SEQUENCE: 47

Gly Ala Gln Thr Leu Tyr Val Pro Asn Cys Asp His Arg
```

-continued

```
<210> SEQ ID NO 48
<211> LENGTH: 13
<212> TYPE: PRT
<213> ORGANISM: Homo sapiens

<400> SEQUENCE: 48

Asn Gly Ile Cys Val Ser Ser Asp Gln Asn His Phe Arg
1               5                   10

<210> SEQ ID NO 49
<211> LENGTH: 9
<212> TYPE: PRT
<213> ORGANISM: Homo sapiens

<400> SEQUENCE: 49

Glu Cys Ala Asp Glu Pro Val Gly Lys
1               5

<210> SEQ ID NO 50
<211> LENGTH: 11
<212> TYPE: PRT
<213> ORGANISM: Homo sapiens

<400> SEQUENCE: 50

Leu Leu Cys Gly Ala Thr Leu Ile Ala Pro Arg
1               5                   10

<210> SEQ ID NO 51
<211> LENGTH: 10
<212> TYPE: PRT
<213> ORGANISM: Homo sapiens

<400> SEQUENCE: 51

Tyr Ser Cys Gln Glu Gly Asp Lys Phe Lys
1               5                   10
```